(12) United States Patent
Stoner et al.

(10) Patent No.: US 11,802,296 B2
(45) Date of Patent: *Oct. 31, 2023

(54) METHODS AND SYSTEMS FOR GUIDE RNA DESIGN AND USE

(71) Applicant: Synthego Corporation, Redwood City, CA (US)

(72) Inventors: Richard Stoner, San Jose, CA (US); Travis Maures, Pacifica, CA (US); David Conant, San Francisco, CA (US)

(73) Assignee: Synthego Corporation, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,790

(22) Filed: Apr. 25, 2022

(65) Prior Publication Data

US 2022/0325300 A1 Oct. 13, 2022

Related U.S. Application Data

(63) Continuation of application No. 16/418,893, filed on May 21, 2019, now Pat. No. 11,345,932, which is a continuation of application No. PCT/US2019/032735, filed on May 16, 2019.

(60) Provisional application No. 62/672,437, filed on May 16, 2018.

(51) Int. Cl.
*C12N 15/90* (2006.01)
*C12N 9/22* (2006.01)
*C12N 15/10* (2006.01)
*C12N 15/113* (2010.01)
*C12N 15/11* (2006.01)

(52) U.S. Cl.
CPC ............. *C12N 15/902* (2013.01); *C12N 9/22* (2013.01); *C12N 15/102* (2013.01); *C12N 15/11* (2013.01); *C12N 15/113* (2013.01); *C12N 2310/20* (2017.05); *C12N 2310/315* (2013.01); *C12N 2310/321* (2013.01); *C12N 2800/80* (2013.01)

(58) Field of Classification Search
CPC .................................................. C12N 15/902
See application file for complete search history.

(56) References Cited

U.S. PATENT DOCUMENTS

| | | | |
|---|---|---|---|
| 5,849,902 A | 12/1998 | Arrow et al. |
| 7,601,492 B2 | 10/2009 | Fu et al. |
| 7,897,737 B2 | 3/2011 | Wu et al. |
| 8,603,996 B2 | 12/2013 | Galloway et al. |
| 8,673,568 B2 | 3/2014 | Weill et al. |
| 8,697,359 B1 | 4/2014 | Zhang |
| 8,771,945 B1 | 7/2014 | Zhang |
| 8,906,616 B2 | 12/2014 | Zhang et al. |
| 9,567,604 B2 | 2/2017 | Joung et al. |
| 9,650,617 B2 | 5/2017 | May et al. |
| 9,663,782 B2 | 5/2017 | Yu et al. |
| 9,738,908 B2 | 8/2017 | Wu |
| 9,771,600 B2 | 9/2017 | Donohoue et al. |
| 9,816,093 B1 | 11/2017 | Donohoue et al. |
| 9,855,297 B2 | 1/2018 | Duchateau et al. |
| 10,000,772 B2 | 6/2018 | Dou et al. |
| 10,106,820 B2 | 10/2018 | Auerbach et al. |
| 10,119,133 B2 | 11/2018 | Joung et al. |
| 10,308,961 B2 | 6/2019 | Doudna et al. |
| 10,329,574 B2 | 6/2019 | Deschamps et al. |
| 10,337,001 B2 | 7/2019 | Ryan et al. |
| 10,337,029 B2 | 7/2019 | Doudna et al. |
| 10,351,878 B2 | 7/2019 | Doudna et al. |
| 10,354,746 B2 | 7/2019 | Cradick et al. |
| 10,358,658 B2 | 7/2019 | Doudna et al. |
| 10,358,659 B2 | 7/2019 | Doudna et al. |
| 10,362,771 B2 | 7/2019 | Mashimo et al. |
| 11,345,932 B2 | 5/2022 | Stoner et al. |
| 2006/0074824 A1 | 4/2006 | Li |
| 2008/0227742 A1 | 9/2008 | Dmochowski et al. |
| 2010/0022761 A1 | 1/2010 | Chen et al. |
| 2010/0216804 A1 | 8/2010 | Zale et al. |
| 2010/0303850 A1 | 12/2010 | Lipford et al. |
| 2011/0020388 A1 | 1/2011 | Zepp et al. |
| 2011/0027217 A1 | 2/2011 | Zepp et al. |
| 2011/0217377 A1 | 9/2011 | Zale et al. |
| 2012/0142051 A1 | 6/2012 | Ogawa et al. |
| 2012/0171229 A1 | 7/2012 | Zepp et al. |
| 2012/0178702 A1 | 7/2012 | Huang et al. |
| 2014/0068797 A1 | 3/2014 | Doudna et al. |
| 2014/0199767 A1 | 7/2014 | Barrangou et al. |
| 2014/0235508 A1 | 8/2014 | Nemoto et al. |
| 2014/0357530 A1 | 12/2014 | Zhang et al. |

(Continued)

FOREIGN PATENT DOCUMENTS

| CN | 106520824 | 3/2017 |
|---|---|---|
| CN | 106637421 A | 5/2017 |

(Continued)

OTHER PUBLICATIONS

Weyel et al. A Two-Photon-Photocleavable Linker for Triggering Light-Induced Strand Breaks in Oligonucleotides. ACS Chem Biol 12:2183-2190 (Jul. 5, 2017).

(Continued)

*Primary Examiner* — Anoop K Singh
*Assistant Examiner* — David A Montanari
(74) *Attorney, Agent, or Firm* — Quarles & Brady, LLP

(57) ABSTRACT

The present disclosure provides a method for designing a set of guide RNAs for hybridizing a genomic region of interest. The present disclosure further provides methods of editing at least one genomic region of interest with at least one set of guide RNAs.

19 Claims, 33 Drawing Sheets

Specification includes a Sequence Listing.

(56) References Cited

U.S. PATENT DOCUMENTS

| | | |
|---|---|---|
| 2015/0024499 A1 | 1/2015 | Brouns et al. |
| 2015/0031133 A1 | 1/2015 | Church et al. |
| 2015/0071899 A1 | 3/2015 | Liu et al. |
| 2015/0191744 A1 | 7/2015 | Wolfe et al. |
| 2015/0232883 A1 | 8/2015 | Dahlman et al. |
| 2015/0291966 A1 | 10/2015 | Zhang et al. |
| 2016/0017396 A1 | 1/2016 | Cann et al. |
| 2016/0024523 A1 | 1/2016 | Joung et al. |
| 2016/0076093 A1 | 3/2016 | Shendure et al. |
| 2016/0108470 A1 | 4/2016 | May et al. |
| 2016/0138008 A1 | 5/2016 | Doudna et al. |
| 2016/0151491 A1 | 6/2016 | Rabinovich et al. |
| 2016/0168592 A1 | 6/2016 | Church et al. |
| 2016/0168594 A1 | 6/2016 | Zhang et al. |
| 2016/0175462 A1 | 6/2016 | Zhang et al. |
| 2016/0201072 A1 | 7/2016 | Cigan et al. |
| 2016/0206566 A1 | 7/2016 | Lu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0237439 A1 | 8/2016 | Liang |
| 2016/0251648 A1 | 9/2016 | Wang et al. |
| 2016/0257973 A1 | 9/2016 | Cameron et al. |
| 2016/0264981 A1 | 9/2016 | Yang et al. |
| 2016/0272965 A1 | 9/2016 | Zhang et al. |
| 2016/0289659 A1 | 10/2016 | Doudna et al. |
| 2016/0304907 A1 | 10/2016 | Mali et al. |
| 2016/0346361 A1 | 12/2016 | Quake et al. |
| 2016/0350476 A1 | 12/2016 | Quake et al. |
| 2016/0355795 A1 | 12/2016 | Ran et al. |
| 2016/0355796 A1 | 12/2016 | Davidson et al. |
| 2016/0362667 A1 | 12/2016 | Donohoue et al. |
| 2016/0362705 A1 | 12/2016 | Abraham et al. |
| 2017/0009256 A1 | 1/2017 | Buerckstuemmer |
| 2017/0020922 A1 | 1/2017 | Wagner et al. |
| 2017/0044537 A1 | 2/2017 | Collingwood et al. |
| 2017/0051276 A1 | 2/2017 | May et al. |
| 2017/0051310 A1 | 2/2017 | Doudna et al. |
| 2017/0058272 A1 | 3/2017 | Carter et al. |
| 2017/0058298 A1 | 3/2017 | Kennedy et al. |
| 2017/0067021 A1 | 3/2017 | Moriarity et al. |
| 2017/0114334 A1 | 4/2017 | May et al. |
| 2017/0137845 A1 | 5/2017 | Tan et al. |
| 2017/0145425 A1 | 5/2017 | Kim et al. |
| 2017/0152506 A1 | 6/2017 | Wagner et al. |
| 2017/0165332 A1 | 6/2017 | Wagner et al. |
| 2017/0166893 A1 | 6/2017 | Doudna et al. |
| 2017/0166903 A1 | 6/2017 | Zhang et al. |
| 2017/0198302 A1 | 7/2017 | Feng et al. |
| 2017/0266320 A1 | 9/2017 | Wagers et al. |
| 2017/0306306 A1 | 10/2017 | Potter et al. |
| 2017/0314015 A1 | 11/2017 | Friedland et al. |
| 2017/0335331 A1 | 11/2017 | Zhao et al. |
| 2017/0349914 A1 | 12/2017 | Cox et al. |
| 2017/0355985 A1 | 12/2017 | Dellinger et al. |
| 2018/0020646 A1 | 1/2018 | Ueda et al. |
| 2018/0100147 A1 | 4/2018 | Yates et al. |
| 2018/0112213 A1 | 4/2018 | Welstead et al. |
| 2018/0119122 A1 | 5/2018 | Zhang et al. |
| 2018/0119140 A1 | 5/2018 | Porteus et al. |
| 2018/0119174 A1 | 5/2018 | Scharenberg et al. |
| 2018/0142236 A1 | 5/2018 | He et al. |
| 2018/0142262 A1 | 5/2018 | Webber et al. |
| 2018/0179521 A1 | 6/2018 | Rahdar et al. |
| 2018/0187195 A1 | 7/2018 | Siksnys et al. |
| 2018/0195089 A1 | 7/2018 | Ravinder et al. |
| 2018/0208931 A1 | 7/2018 | Doudna et al. |
| 2018/0216135 A1 | 8/2018 | Tsai et al. |
| 2018/0258411 A1 | 9/2018 | Kadiyala et al. |
| 2018/0282763 A1 | 10/2018 | Cigan et al. |
| 2018/0298392 A1 | 10/2018 | Cotta-Ramusino |
| 2018/0305718 A1 | 10/2018 | Nelson et al. |
| 2018/0312828 A1 | 11/2018 | Liu et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0320197 A1 | 11/2018 | Gersbach et al. |
| 2018/0334665 A1 | 11/2018 | Yu et al. |
| 2019/0002990 A1 | 1/2019 | Scully et al. |
| 2019/0010495 A1 | 1/2019 | Boitano et al. |
| 2019/0010519 A1 | 1/2019 | Corn et al. |
| 2019/0020646 A1 | 1/2019 | Magyar et al. |
| 2019/0032052 A1 | 1/2019 | Zhang et al. |
| 2019/0032053 A1 | 1/2019 | Ji et al. |
| 2019/0032092 A1 | 1/2019 | Gong et al. |
| 2019/0085329 A1 | 3/2019 | Šikšnys et al. |
| 2019/0106708 A1 | 4/2019 | Fahrenkrug et al. |
| 2019/0106710 A1 | 4/2019 | Zhang et al. |
| 2019/0112619 A1 | 4/2019 | Frendewey et al. |
| 2019/0119678 A1 | 4/2019 | Grimm et al. |
| 2019/0136229 A1 | 6/2019 | Josephs et al. |
| 2019/0169642 A1 | 6/2019 | Doudna et al. |
| 2019/0169646 A1 | 6/2019 | Doudna et al. |
| 2019/0169653 A1 | 6/2019 | Aida et al. |
| 2019/0194632 A1 | 6/2019 | Thorn et al. |
| 2019/0218547 A1 | 7/2019 | Lee et al. |
| 2019/0249200 A1 | 8/2019 | Seebeck et al. |
| 2019/0382797 A1 | 12/2019 | Stoner et al. |
| 2020/0270680 A1 | 8/2020 | Hsiau |
| 2020/0392473 A1 | 12/2020 | Zhang et al. |

FOREIGN PATENT DOCUMENTS

| | | |
|---|---|---|
| EP | 2764103 A2 | 8/2014 |
| EP | 2800811 A1 | 11/2014 |
| EP | 2771468 B1 | 2/2015 |
| EP | 2931897 B1 | 11/2015 |
| EP | 2940140 A1 | 11/2015 |
| EP | 2877571 B1 | 3/2016 |
| EP | 3031921 A1 | 6/2016 |
| EP | 3079726 A2 | 10/2016 |
| EP | 3239298 | 1/2017 |
| EP | 3178935 A1 | 6/2017 |
| EP | 3004337 B1 | 8/2017 |
| EP | 3199632 A1 | 8/2017 |
| EP | 2931892 B1 | 11/2017 |
| EP | 3279321 A1 | 2/2018 |
| EP | 3066201 B1 | 3/2018 |
| EP | 3360964 A1 | 8/2018 |
| EP | 2898075 B1 | 9/2018 |
| EP | 3372679 A1 | 9/2018 |
| EP | 3030650 B1 | 10/2018 |
| EP | 3022304 B1 | 12/2018 |
| EP | 3426776 A1 | 1/2019 |
| EP | 3426784 A1 | 1/2019 |
| EP | 3434776 A1 | 1/2019 |
| EP | 3221457 B1 | 3/2019 |
| JP | 4243680 B2 | 3/2009 |
| WO | WO9813526 A1 | 4/1998 |
| WO | WO2008103276 A2 | 8/2008 |
| WO | WO2010005740 A2 | 1/2010 |
| WO | WO2010030763 A2 | 1/2010 |
| WO | WO2010075072 A2 | 3/2010 |
| WO | WO2010138192 A2 | 12/2010 |
| WO | WO2010138193 A2 | 12/2010 |
| WO | WO2010138194 A2 | 12/2010 |
| WO | WO2011084518 A2 | 7/2011 |
| WO | WO2011127255 A1 | 10/2011 |
| WO | WO2012092552 A1 | 7/2012 |
| WO | WO2012099755 A1 | 7/2012 |
| WO | WO2014093595 A1 | 6/2014 |
| WO | WO2014204723 A1 | 12/2014 |
| WO | WO2015121454 A1 | 8/2015 |
| WO | WO2015195621 A1 | 12/2015 |
| WO | WO2015200555 A2 | 12/2015 |
| WO | WO2016033246 A1 | 3/2016 |
| WO | WO2016049251 A1 | 3/2016 |
| WO | WO2016057961 A1 | 4/2016 |
| WO | WO2016065364 A1 | 4/2016 |
| WO | WO2016022363 A3 | 5/2016 |
| WO | WO2016069282 A1 | 5/2016 |
| WO | WO2016069283 A1 | 5/2016 |
| WO | WO2016094867 A1 | 6/2016 |
| WO | WO2016094874 A1 | 6/2016 |

(56) References Cited

FOREIGN PATENT DOCUMENTS

| | | |
|---|---|---|
| WO | WO2016094880 A1 | 6/2016 |
| WO | WO2016183402 A2 | 8/2016 |
| WO | WO2016196273 A1 | 10/2016 |
| WO | WO2016196283 A1 | 11/2016 |
| WO | WO2017044419 A1 | 12/2016 |
| WO | WO2017049266 A2 | 12/2016 |
| WO | WO2017053729 A1 | 3/2017 |
| WO | WO2017053879 A1 | 3/2017 |
| WO | WO2017068377 A1 | 3/2017 |
| WO | WO2017068377 A1 | 4/2017 |
| WO | WO2017079400 A1 | 5/2017 |
| WO | WO2017081097 A1 | 5/2017 |
| WO | WO2017083766 A1 | 6/2017 |
| WO | WO2017093370 A1 | 6/2017 |
| WO | WO2017093969 A1 | 6/2017 |
| WO | WO2017096041 A1 | 6/2017 |
| WO | WO2017100343 A1 | 6/2017 |
| WO | WO2017106569 A1 | 6/2017 |
| WO | WO2017115268 A1 | 7/2017 |
| WO | WO2017120410 A1 | 7/2017 |
| WO | WO2017120996 A1 | 7/2017 |
| WO | WO2017120998 A1 | 7/2017 |
| WO | WO2017155407 A1 | 9/2017 |
| WO | WO2017155408 | 9/2017 |
| WO | 2016104716 A1 | 10/2017 |
| WO | WO2017178590 A1 | 10/2017 |
| WO | WO2017184799 | 10/2017 |
| WO | WO2017189336 A1 | 11/2017 |
| WO | WO2017193107 A2 | 11/2017 |
| WO | WO2017197238 A1 | 11/2017 |
| WO | WO2017201476 A1 | 11/2017 |
| WO | WO2017217768 A1 | 12/2017 |
| WO | WO2018005873 A1 | 1/2018 |
| WO | WO2018009534 A1 | 1/2018 |
| WO | WO2018014384 A1 | 1/2018 |
| WO | WO2018031950 A1 | 2/2018 |
| WO | WO2018067826 A1 | 4/2018 |
| WO | WO2018067991 A1 | 4/2018 |
| WO | WO2018068257 A1 | 4/2018 |
| WO | WO2018083071 A1 | 5/2018 |
| WO | WO2018096356 A1 | 5/2018 |
| WO | WO018130830 A1 | 7/2018 |
| WO | WO2018126176 A1 | 7/2018 |
| WO | WO2018174097 A1 | 9/2018 |
| WO | WO2018205926 A1 | 11/2018 |
| WO | WO2018209320 A1 | 11/2018 |
| WO | WO2018226575 A1 | 12/2018 |
| WO | WO2018232356 A1 | 12/2018 |
| WO | WO2018233596 A1 | 12/2018 |
| WO | WO2019010384 A1 | 1/2019 |
| WO | WO2019014489 A1 | 1/2019 |
| WO | WO2019027728 A1 | 2/2019 |
| WO | WO2019040645 A1 | 2/2019 |
| WO | WO2019055495 A1 | 3/2019 |
| WO | WO2019058253 A1 | 3/2019 |
| WO | WO2019099943 A1 | 5/2019 |
| WO | WO2019092507 A3 | 6/2019 |
| WO | WO2019106522 A1 | 6/2019 |
| WO | WO2019118948 A2 | 6/2019 |
| WO | WO2019118949 A1 | 6/2019 |
| WO | WO2019126774 A1 | 6/2019 |
| WO | WO2019133714 A1 | 7/2019 |
| WO | WO2019147275 A1 | 8/2019 |
| WO | WO2019204668 A1 | 10/2019 |
| WO | WO2019222545 A1 | 11/2019 |
| WO | WO2019232494 A2 | 12/2019 |
| WO | WO2020093025 A1 | 5/2020 |
| WO | WO2020154714 | 7/2020 |
| WO | WO2020154714 | 9/2020 |
| WO | WO202101613 | 1/2021 |

OTHER PUBLICATIONS

Wheeler et al. Stabilized Plasmid-Lipid Particles: Construction and Characterization. Gene Therapy 6:271-281 (1999).

Wright et al. Rational design of a split-Cas9 enzyme complex. PNAS USA 112(10):2984-9 (Feb. 23, 2015).

Xu et al. Evolution and characterization of a benzylguanine-binding RNA aptamer. Chem Commun (Camb) 52(3):549-552 (Jan. 11, 2016). DOI: 10.1039/c5cc07605f.

Zaug et al. Sequence-specific endoribonuclease activity of the Tetrahymena ribozyme: enhanced cleavage of certain oligonucleotide substrates that form mismatched ribozyme-substrate complexes. Biochemistry 27(25):8924-8931 (1988).

Zetsche et al. Cpf1 is a single RNA-guided endonuclease of a class 2 CRISPR-Cas system. Cell 163:759-771 (2015).

Zetsche et al. Multiplex gene editing by CRISPR-Cpf1 using a single crRNA array. Nature Biotechnology 35:31-34 (2017). Published online Dec. 5, 2016. Corrected after print Jan. 12, 2017.

Zhang et al. Self-assembled lipid—polymer hybrid nanoparticles: a robust drug delivery platform. ACS Nano 2:1696-1702 (2008).

Zhang et al. Stabilized plasmid-lipid particles for regional gene therapy: formulation and transfection properties. Gene Therapy 6:1438-1447 (Aug. 20, 1999).

Zhidkov et al. CHILD: a new tool for detecting low-abundance insertions and deletions in standard sequence traces. Nucleic Acids Research 39(7):e47 (2011). Published online Jan. 28, 2011. 8 pages.

Zhou et al. One-step generation of different immunodeficient mice with multiple gene modifications by CRISPR/Cas9 mediated genome engineering. International Journal of Biochemistry and Cell Biology 46:49-55 (Jan. 2014). DOI: https://doi.org/10.1016/j.biocel.2013.10.010.

Zhou et al. A Single-Chain Photoswitchable CRISPR-Cas9 Architecture for Light-Inducible Gene Editing and Transcription. ACS Chem Biol. 13(2):443-448 (Feb. 16, 2018). Published online Sep. 22, 2017.

Zhou et al. Dual sgRNAs facilitate CRISPR/Cas9-mediated mouse genome targeting. FEBS J 2014; 281:1717-1725. First published Feb. 3, 2014.

Zhu et al. Genome-scale deletion screening of human long non-coding RNAs using a paired-guide RNA CRISPR-Cas9 library. Nat Biotechnol 34, 1279-1286 (2016). Published online Oct. 31, 2016.

Zuo et al. One-step generation of complete gene knockout mice and monkeys by CRISPR/Cas9-mediated gene editing with multiple sgRNAs. Cell Research 27:933-945 (2017). Published online Jun. 6, 2017.

U.S. Appl. No. 16/418,893 Office Action dated Aug. 18, 2021.
U.S. Appl. No. 17/116,791 Office Action dated May 10, 2022.
U.S. Appl. No. 17/116,791 Office Action dated Jun. 1, 2021.

Sunagawa; Genshiro A. et al., "Mammalian Reverse Genetics without Crossing Reveals Nr3a as a Short-Sleeper Gene", Cell Reports, 14(3):662-677 (2016).

Shalem; O. et al., "Genome-Scale CRISPR-Cas9 Knockout Screening in Human Cells", Science, 343(6166):84-87 (2014).

Jang; Da Eun, et al. "Multiple sgRNAs with overlapping sequences enhance CRISPR/Cas9-mediated knock-in efficiency", Experimental & Molecular Medicine, 50:16 (2018), XP055716076, DOI: 10.1038/512276-018-0037-x.

Charleston; Noble, et al. "Evolutionary dynamics of CRISPR gene drives", Science Advances, 3:4 (2017), p. e1601964, XP055549865, DOI: 10.1126/sciadv.1601964.

The Moore Dissertation, published 2015. (Year: 2015).
The Rubin Dissertation, published 2013. (Year: 2013).

PCT/US2019/032735 International Search Report and Written Opinion dated Oct. 3, 2019.

PCT/US2019/035079 International Search Report and Written Opinion dated Nov. 20, 2019.

PCT/US2019/059557 International Search Report and Written Opinion dated Feb. 20, 2020.

Pearson et al. Improved Tools for Biological Sequence Comparison. PNAS USA 85:2444-48 (1988).

Peng et al. CRISPR-Cas9-Mediated Single-Gene and Gene Family Disruption in Trypanosoma cruzi. mBio 6(1):1-11 (Dec. 30, 2014).

Photoreactive Crosslinker Chemistry. Protein Biology Resource Library, ThermoFisher Scientific (website). Retrieved Feb. 5, 2019 at URL: https://www.thermofisher.com/us/en/home/life-science/protein-biology/protein-biology-Learning-center/protein-biology-

(56) References Cited

OTHER PUBLICATIONS resource-library/pierce-protein-methods/photoreactive-crosslinker-chemistry.html.6 pages.
Pinello, et al. Analyzing CRISPR genome-editing experiments with CRISPResso. Nat Biotechnol. Jul. 12, 2016; 34(7): 695-697.
Polstein et al. A light-inducible CRISPR/Cas9 system for control of endogenous gene activation. Nat Chem Biol. Mar. 2015; 11(3): 198-200.
Poly Peak Parser. Retrieved Sep. 17, 2018 at URL: yosttools.genetics.utah.edu/PolyPeakParser. 4 pages.
Pulido-Quetglas et al. Scalable Design of Paired CRISPR Guide RNAs for Genomic Deletion. PLoS Comput Biol. Mar. 2017; 13(3): e1005341. Epub Mar. 2, 2017. doi: 10.1371/journal.pcbi.1005341.
Quality Scores for Next-Generation Sequencing. Illumina. Copyright 2011. 2 pages.
Raper et al. Functional Insights Revealed by the Kinetic Mechanism of CRISPR/Cas9. J. Am. Chem. Soc. 140(8):2971-2984 (Feb. 14, 2018).
Richter et al. Switchable Cas9. CurrOpin Biotechnol 48:119-126 (Dec. 2017). Epub Apr. 26, 2017. doi: 10.1016/j.copbio.2017.03.025.
Rodriguez et al. APPRIS: annotation of principal and alternative splice isoforms. Nucleic Acids Research, vol. 41, Database issue, pp. D110-D117, (2013). Published online Nov. 17, 2012.
Samarsky et al. A small nucleolar RNA:ribozyme hybrid cleaves a nucleolar RNA target in vivo with near-perfect efficiency. Proc Natl Acad Sci U S A 96(12):6609-6614 (Jun. 8, 1999).
Sanson et al. Optimized libraries for CRISPR-Cas9 genetic screens with multiple modalities. Nat Commun. 2018; 9:5416 Published online Dec. 21, 2018. doi: 10.1038/s41467-018-07901-8. 15 pages.
Scaringe. Advanced 5'-Silyl-2'-Orthoester Approach to RNA Oligonucleotide Synthesis. Methods Enzymology. 2000;317:3-18.
Scaringe et al. Novel RNA synthesis method using 5'-0-silyl-2'-0-orthoester protecting groups. Journal of American Chemical Society. 1998;120:11820-11821. Epub Nov. 3, 1998.
Schroeder et al. Lipid-based nanotherapeutics for siRNA delivery. Journal of Internal Medicine 267(1):9-21 (Jan. 2010). First published Dec. 11, 2009. DOI: https://doi.org/10.1111/j.1365-2796.2009.02189.x.
Shao et al. Synthetic far-red light-mediated CRISPR-dCas9 device for inducing functional neuronal differentiation. PNAS115(29):E6722-E6730 (Jul. 17, 2018). First published Jul. 2, 2018. doi: https://doi.org/10.1073/pnas.1802448115.
Shen et al. Predictable and precise template-free CRISPR editing of pathogenic variants. Nature 563:646-651 (Nov. 7, 2018). Author Correction published Feb. 14, 2019.doi:10.1038/s41586-018-0686-x.
Shigemizu et al. IMSindel: An accurate intermediate-size indel detection tool incorporating de novo assembly and gapped global-local alignment with split read analysis. Scientific Reports 8:5608 (2018). Published online Apr. 4, 2018. DOI:10.1038/s41598-018-23978-z. 9 pages.
Shmakov et al. Discovery and Functional Characterization of Diverse Class 2 CRISPR-Cas Systems. Mol Cell 60(3):385-397 (2015).
Shukla et al. Exploring Chemical Modifications for siRNA Therapeutics: A Structural and Functional Outlook. ChemMedChem 5(3):328-349 (2010).
Siegwart, D.J. et al., Combinatorial synthesis of chemically diverse core-shell nanoparticles for intracellular delivery. Proceedings of the National Academy of the Sciences of the USA 108(32):12996-123001 (2011).
Slaymaker et al. Rationally engineered Cas9 nucleases with improved specificity. Science 351(6268):84-88 (Jan. 1, 2016).
Sletten, et al. Bioorthogonal chemistry: fishing for selectivity in a sea of functionality. Angew Chem Int Ed Engl. 2009;48(38):6974-98. doi: 10.1002/anie.200900942.
Smith et al. Comparison of Biosequences. Adv. Appl. Math. 2:482-489 (1981).
Song et al. Efficient dual sgRNA-directed large gene deletion in rabbit with CRISPR/Cas9 system. Cell. Mol. Life Sci. 73, 2959-2968 (2016). Published online Jan. 27, 2016.
Sürün et al. High Efficiency Gene Correction in Hematopoietic Cells by Donor-Template-Free CRISPR/Cas9 Genome Editing. Molecular Therapy: Nucleic Acids. vol. 10 (Mar. 2018). Copyright 2017 by The Author(s). 8 pages.
Staals et al. RNA Targeting by the Type III-A CRISPR-Cas Csm Complex of Thermus thermophilus. Molecular Cell 56:518-530 (Nov. 20, 2014).
Su, et al. In vitro and in vivo mRNA delivery using lipid-enveloped pH-responsive polymer nanoparticles. Mol Pharm. Jun. 6, 2011;8(3):774-87. doi: 10.1021/mp100390w. Epub Apr. 1, 2011.
Sulej et al. Sequence-specific cleavage of the RNA strand in DNA-RNA hybrids by the fusion of ribonuclease H with a zinc finger. Nucleic Acids Res 40(22):11563-11570 (Dec. 2012). Epub Oct. 5, 2012.doi: 10.1093/nar/gks885.
Synthego website. 2 pages. Accessed Oct. 31, 2018 at URL: (https://design.synthego.com/#/>).
Tamulaitis et al. Programmable RNA Shredding by the Type III-A CRISPR-Cas System of *Streptococcus thermophilus*. Molecular Cell 56:506-517 (Nov. 20, 2014).
Tatusova, et al., Erratum to BLAST 2 Sequences, a new tool for comparing protein and nucleotide sequences [FEMS Microbiol. 174 (1999) 247-250], FEMS Microbial. Lett. 1999;177(1):187-188.
Tatusova et al. BLAST 2 Sequences, a new tool for comparing protein and nucleotide sequences. FEMS Microbiology Letters 174:247-250 (1999).
Threlfall et al. Synthesis and biological activity of phosphonoacetate- and thiophosphonoacetate-modified 2'-O-methyl oligoribonucleotides. Org Biomol Chem 10:746-754 (2012).
TIDE: Tracking of Indels by DEcomposition. Retrieved Sep. 13, 2018 at URL: https://tide.deskgen.com/. 4 pages.
Tider. Retrieved Sep. 13, 2018 at URL: https://tider.deskgen.com. 5 pages.
Tsai, et al. GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Tzelepis et al. A CRISPR Dropout Screen Identifies Genetic Vulnerabilities and Therapeutic Targets in Acute Myeloid Leukemia. Cell Rep. Oct. 18, 2016; 17(4): 1193-1205. Published online Oct. 18, 2016. doi: 10.1016/j.celrep.2016.09.079.
Van Agtmaal et al. CRISPR/Cas9-Induced (CTG • CAG)n Repeat Instability in the Myotonic Dystrophy Type 1 Locus: Implications for Therapeutic Genome Editing. Molecular Therapy 25(1):24-43 (Jan. 4, 2017). DOI: https://doi.org/10.1016/j.ymthe.2016.10.014.
Wang et al. CRISPR-DAV: CRISPR NGS data analysis and visualization pipeline. Bioinformatics 33(23):3811-3812 (2017). Advance Access Publication Date: Aug. 14, 2017.
Wang et al. Genetic screens in human cells using CRISPR-Cas9 system. Science 343:80-84 (2014).
Wang et al. Dual gRNAs guided CRISPR/Cas9 system inhibits hepatitis B virus replication. World J Gastroenterol. Aug. 28, 2015; 21(32): 9554-9565. Published online Aug. 28, 2015. doi: 10.3748/wjg.v21.i32.9554.
Wang. Co-delivery of drugs and DNA from cationic core-shell nanoparticles self-assembled from a biodegradable copolymer. Nat Mater 5(10):791-796 (Oct. 2006). Epub Sep. 24, 2006.
Watts et al. Chemically modified siRNA: tools and applications. Drug Discov Today 13(19-20):842-855 (2008).
Wenzel et al. Genosnip: SNP Genotyping by MALDI-TOF MS Using Photocleavable Oligonucleotides. Nucleosides Nucleotides Nucleic Acids. May 2003-Aug. 22(5-8):1579-81. Published online Aug. 31, 2006.
Werner et al. Short oligonucleotides as external guide sequences for site-specific cleavage of RNA molecules with human RNase P. RNA. Jul. 1998;4(7):847-55.
FORECasT Favoured Outcomes of Repair Events at Cas9 Targets. Wellcome Sanger Institute. One page. Retrieved Jun. 21, 2019 at URL: https://partslab.sanger.ac.uk/FORECasT.

(56) References Cited

OTHER PUBLICATIONS

Fukuma et al. Conjugation of an antisense oligodeoxynucleotide to ribonuclease h results in sequence-specific cleavage and intracellular inhibition of HCV gene expression. Bioconjug Chem 14(2):295-301 (2003). Epub Jan. 30, 2003.
Fuller et al. Intracellular delivery of core-shell fluorescent silica nanoparticles. Biomaterials 29(10):1526-1532 (2008). Epub Dec. 21, 2007. DOI: https://doi.org/10.1016/j.biomaterials.2007.11.025.
Gangopadhyay et al. Precision Control of CRISPR-Cas9 Using Small Molecules and Light. Biochemistry. Jan. 29, 2019; 58(4): 234-244. doi:10.1021/acs.biochem.8b01202.
Genovese et al. Mapping the Human Reference Genome's Missing Sequence by Three-Way Admixture in Latino Genomes. American Journal of Human Genetics 93(3):411-421 (Sep. 5, 2013).
Gnaccarini et al. Site-specific cleavage of RNA by a metal-free artificial nuclease attached to antisense oligonucleotides. J Am Chem Soc 128(24):8063-8067 (2006). Epub May 25, 2006.
Grissa et al. CRISPRFinder: a web tool to identify clustered regularly interspaced short palindromic repeats. Nucleic Acids Res. 35(Web Server issue):W52-57 (2007).
Guzzardo et al. A small cassette enables conditional gene inactivation by CRISPR/Cas9. Scientific Reports vol. 7, Article No. 16770 (Dec. 1, 2017). DOI: 10.1038/s41598-017-16931-z. 11 pages.
Głów et al. Sequence-specific cleavage of dsRNA by Mini-III RNase. Nucleic Acids Res 43(5):2864-2873 (Mar. 11, 2015). Epub Jan. 29, 2015. doi: 10.1093/nar/gkv009.
Hart et al. High-Resolution CRISPR Screens Reveal Fitness Genes and Genotype-Specific Cancer Liabilities. Cell 163(3):1515-1526 (Dec. 3, 2015).
Hemphill et al. Optical Control of CRISPR/Cas9 Gene Editing. J Am Chem Soc 137(17):5642-5645 (Apr. 23, 2015).
Hendel, et al. Chemically modified guide RNAs enhance CRISPR-Cas genome editing in human primary cells. Nat Biotechnol. Sep. 2015;33(9):985-9. doi: 10.1038/nbt.3290. Epub Jun. 29, 2015.
Ho et al. Targeting non-coding RNAs with the CRISPR/Cas9 system in human cell lines. Nucleic Acids Res. Feb. 18, 2015;43(3):e17. doi: 10.1093/nar/gku1198. Epub Nov. 20, 2014. 11 pages.
How the sgRNA Designer Works (all versions). Broad Institute, Genetic Perturbation Platform (GPP) Web Portal. 3 pages. Accessed Oct. 31, 2018 at URL: (https://portals.broadinstitute.org/gpp/public/software/sgrna-scoring-help).
Hsiau et al. Inference of CRISPR Edits from Sanger Trace Data. Version 1. bioRxiv (Jan. 20, 2018). Retrieved from URL: https://www.biorxiv.org/content/10.1101/251082v1. 14 pages.
Hsiau et al. Inference of CRISPR Edits from Sanger Trace Data. Version 2. bioRxiv (published Jan. 20, 2018, updated Jan. 14, 2019). Retrieved from URL: https://www.biorxiv.org/content/10.1101/251082v2. 16 pages.
Hsiau et al. Inference of CRISPR Edits from Sanger Trace Data. Version 3. bioRxiv (published Jan. 20, 2018; updated Aug. 10, 2019). Retrieved from URL: https://www.biorxiv.org/content/10.1101/251082v3. 17 pages.
InDelphi machine learning algorithm. Gifford Laboratory at MIT. 2 pages. Retrieved Jun. 20, 2019 at URL: https://indelphi.giffordlab.mit.edu/about.
Jeffs et al. A Scalable, Extrusion-Free Method for Efficient Liposomal Encapsulation of Plasmid DNA. Pharm Res., 22(3):362-72, 2005.
Jensen et al. Comparative analysis of NHEJ and HDR repair pathways for genomic editing using CRISPR/Cas9 technology in ES cells. Charles River. Poster presented in "CRISPR Genome Editing: From high-throughput screening to disease models" meeting in Copenhagen, Denmark on Sep. 22, 2016. URL: https://www.criver.com/sites/default/files/resources/ComparativeAnalysisofNHEJandHDRRepairPathwaysforGenomicEditingUsingCRISPRCas9TechnologyinESCells.pdf.
Jinek et al. RNA-programmed genome editing in human cells. eLife 2013;2:e00471 doi: 10.7554/eLife.00471. 14 pages. Retrieved Mar. 23, 2020 from URL: https://elifesciences.org/articles/00471.
Jobst-Schwan et al. Acute multi-sgRNA knockdown of KEOPS complex genes reproduces the microcephaly phenotype of the stable knockout zebrafish model. PLoS One. 2018; 13(1): e0191503. Published online Jan. 18, 2018. doi: 10.1371/journal.pone.0191503. 18 pages.
Josephs et al. Structure and specificity of the RNA-guided endonuclease Cas9 during DNA interrogation, target binding and cleavage. Nucleic Acids Res 43(18):8924-8941 (Sep. 17, 2015).
Joung et al. Genome-scale CRISPR-Cas9 Knockout and Transcriptional Activation Screening. Nat Protoc. 12(4):828-863 (Apr. 2017). doi:10.1038/nprot.2017.016.
Kim et al. Deep learning improves prediction of CRISPR-Cpf1 guide RNA activity. Nature Biotechnology Advance Online Publication published Jan. 29, 2018. doi: 10.1038/nbt.4062. 8 pages.
Klein et al. Hybridization Kinetics Explains CRISPR-Cas Off-Targeting Rules. Cell Reports 22:1413-1423 (Feb. 6, 2018).
Kocak et al. Increasing the specificity of CRISPR systems with engineered RNA secondary structures. Nature Biotechnology 37:657-666 (2019). Published online Apr. 15, 2019.
Kowalik et al. Illuminating developmental biology through photochemistry. Nature Chemical Biology 13:587-598 (2017). Epub May 17, 2017.
Lamanna. Optogenetics + CRISPR, Using Light to Control Genome Editing. Blog post, Addgene blog (Mar. 8, 2016). Retrieved Jan. 22, 2020 at URL: https://blog.addgene.org/optogenetics-crispr-using-light-to-control-genome-editing. 8 pages.
Leenay et al. Systematic characterization of genome editing in primary T cells reveals proximal genomic insertions and enables machine learning prediction of CRISPR-Cas9 DNA repair outcomes. bioRxiv, Aug. 31, 2018. 37 pages. Retrieved Jun. 20, 2019 at URL: https://www.biorxiv.org/content/10.1101/404947v1.article-info.
Levy et al. Direct selection of trans-acting ligase ribozymes by in vitro compartmentalization. RNA 11(10):1555-1562 (Oct. 2005). Epub Aug. 30, 2005.
Liang et al. Enhanced CRISPR/Cas9-mediated precise genome editing by improved design and delivery of gRNA, Cas9 nuclease, and donor DNA. Journal of Biotechnology 241:136-146 (2017). Available online Nov. 11, 2016.
Li. Structural Principles of CRISPR RNA Processing. Structure 23(1):13-20 (Jan. 6, 2015). Epub Nov. 26, 2014. doi: 10.1016/j.str.2014.10.006.
Listgarten et al. Prediction of off-target activities for the end-to-end design of CRISPR guide RNAs. Nature Biomedical Engineering 2(1):38-47 (Jan. 10, 2018).
Love et al. Lipid-like materials for low-dose, in vivo gene silencing. PNAS 107(5):1864-1869 (Feb. 2, 2010). DOI: https://doi.org/10.1073/pnas.0910603106. Correction for article, PNAS 107(21):9915 (May 25, 2010). DOI: https://doi.org/10.1073/pnas.0910603106.
Mahon et al. Combinatorial Approach to Determine Functional Group Effects on Lipidoid-Mediated siRNA Delivery. Bioconjugate Chem 21(8):1448-1454 (2010). Epub Jul. 16, 2010. DOI: https://doi.org/10.1021/bc100041r.
Manoharan. RNA interference and chemically modified small interfering RNAs. Current Opinion in Chemical Biology 8(6):570-579 (2004). Available online Oct. 22, 2004. DOI: https://doi.org/10.1016/j.cbpa.2004.10.007.
Matteucci, et al. Synthesis of deoxyoligonucleotides on a polymer support. J. Am. Chem. Soc. 103(11):3185-3191, 1981.
Mekler et al. Kinetics of the CRISPR-Cas9 effector complex assembly and the role of 3'-terminal segment of guide RNA. Nucleic Acids Res. 44(6):2837-2845 (Mar. 3, 2016).
Meizakopian et al. Enhancing the genome editing toolbox: genome wide CRISPR arrayed libraries. Scientific Reports 7:2244 (May 22, 2017). 9 pages.
Morrissey et al., Potent and Persistent in vivo Anti-HBV Activity of Chemically Modified siRNAs. Nat. Biotechnol. 23(8):1003-1007 (2005).
Naito et al. CRISPRdirect: software for designing CRISPR/Cas guide RNA with reduced off-target sites. Bioinformatics, 31(7):1120-1123 (Nov. 20, 2014). doi: 10.1093/bioinformatics/btu743.
Needham-Vandevanter et al. Characterization of an adduct between CC-1065 and a defined bligodeoxynucleotide duplex. Nucleic Acids Res 12(15):6159-6168 (Aug. 10, 1984).

(56) References Cited

OTHER PUBLICATIONS

Needleman et al. A general method applicable to the search for similarities in the amino acid sequence of two proteins. Journal of molecular biology 48(3):443-453 (1970).

Nishimasu et al. Crystal structure of *Streptococcus pyogenes* Cas9 in complex with guide RNA and target DNA. Worldwide Protein Data Bank (2014). DOI: 10.2210/pdb4oo8/pdb. 1 page. Retrieved Dec. 8, 2019 from URL: https://www.wwpdb.org/pdb?id=pdb_00004oo8.

O'Geen et al. A genome-wide analysis of Cas9 binding specificity using ChIP-seq and targeted sequence capture. Nucleic Acids Research 43(6):3389-3404 (2015). Published online Feb. 20, 2015. doi: 10.1093/nar/gkv137.

Olejnik et al. Photocleavable aminotag phosphoramidites for 5'-termini DNA/RNA labeling. Nucleic Acids Res 26(15):3572-3576 (1998).

Ortigão et al. Antisense effect of oligodeoxynucleotides with inverted terminal internucleotidic linkages: a minimal modification protecting against nucleolytic degradation. Antisense Res Dev 2(2):129-146 (1992).

Pan et al. Near-infrared upconversion-activated CRISPR-Cas9 system: A remote-controlled gene editing platform. Science Advances 5(4):eaav7199 (Apr. 3, 2019). 11 pages.

Park et al. Cas-Database: web-based genome-wide guide RNA library design for gene knockout screens using CRISPR-Cas9. Bioinformatics 32(13):2017-2023 (Feb. 24, 2016). DOI: https://doi.org/10.1093/bioinformatics/btw103.

Chen et al. Dynamic Imaging of Genomic Loci in Living Human Cells by an Optimized CRISPR/Cas System. Cell. Dec. 19, 2013; 155(7): 1479-1491. doi: 10.1016/j.cell.2013.12.001.

Jain et al. Development of Light-Activated CRISPR Using Guide RNAs with Photocleavable Protectors. Angew Chem Int Ed Engl. Sep. 26, 2016; 55(40): 12440-12444. Published online Aug. 24, 2016. doi: 10.1002/anie.201606123. Supporting Information, 19 pages.

Lee et al. Synthetically modified guide RNA and donor DNA are a versatile platform for CRISPR-Cas9 engineering. eLife. 2017; 6: e25312. Published online May 2, 2017. doi: 10.7554/eLife.25312. 17 pages.

Liu, Q. Synthesis of Photo- and Chemical-Activated Nucleosides and Unnatural Amino Acids (Dissertation), North Carolina State University, 315 pages (2014).

Maleimide, Biosynthesis (website), 2018. Retrieved Dec. 17, 2020 at URL: https://web.archive.org/web/20180620150124/http://www.biosyn.com/oligonucleotideproduct/maleimide-oligonucleotide-modification.aspx. 2 pages.

Nishimasu et al. Crystal Structure of Cas9 in Complex with Guide RNA and Target DNA. Cell 156(5):935-949 (2014).

PCT/US2019/032735 International Preliminary Report on Patentability dated Nov. 17, 2020.

PCT/US2019/035079 International Preliminary Report on Patentability dated Dec. 1, 2020.

PCT/US2020/015127 International Search Report and Written Opinion dated Jul. 22, 2020.

PCT/US2020/042681 International Search Report and Written Opinion dated Dec. 3, 2020.

Sigman et al. Chemical nucleases. Chem. Rev. 93, 6, 2295-2316 (Sep. 1, 1993). DOI: https://doi.org/10.1021/cr00022a011.

U.S. Appl. No. 16/418,893 Office Action dated Jun. 18, 2020.

U.S. Appl. No. 16/418,893 Office Action dated Sep. 22, 2020.

Knuckles et al. RNA fate determination through cotranscriptional adenosine methylation and microprocessor binding. Nat Struct Mol Biol. Jul. 2017;24(7):561-569. doi: 10.1038/nsmb.3419. Epub Jun. 5, 2017. With Supplementary Text and Figures, 6 pages.

Peng et al. EuPaGDT: a web tool tailored to design CRISPR guide RNAs for eukaryotic pathogens. Microbial Genomics (2015). 7 pages.

Woodbury-Smith et al. Mutations in RAB39B in individuals with intellectual disability, autism spectrum disorder, and macrocephaly. Molecular Autism (2017) 8:59. 10 pages.

Akinc, A. et al., A combinatorial library of lipid-like materials for delivery of RNAi therapeutics. Nature Biotechnology 26(5):561-569 (May 2008). Published online Apr. 27, 2008. DOI: 10.1038/nbt1402.

Allen et al. Predicting the mutations generated by repair of Cas9-induced double-strand breaks. Nature Biotechnology 37:64-72 (2019). Published online Nov. 27, 2018.

Amir et al. Bacterial Community Reconstruction Using Compressed Sensing. V. Bafna and S.C. Sahinalp (Eds.): RECOMB 2011, LNB1 6577, pp. 1-15, 2011. Copyright Springer-Verlag Berlin Heidelberg 2011.

Aparicio-Prat et al. DECKO: Single-oligo, dual-CRISPR deletion of genomic elements including long non-coding RNAs. BMC Genomics. Oct. 23, 2015;16:846. doi: 10.1186/s12864-015-2086-z. 15 pages. Erratum in vol. 15, Article No. 215 (2016). Published online Mar. 9, 2016. One page.

Arbab et al. Predictable and precise template-free editing by CRISPR-Cas9 nuclease. Poster presented at 2nd Annual Genome Editing USA Congress, May 10-11, 2018.

Beaucage et al. Deoxynucleoside Phosphoramidites—A New Class of Key Intermediates for Deoxypolynucleotide Synthesis. Tetrahedron Letters. 1981;22(20):1859-1862.

Behlke, M. Chemical modification of siRNAs for in vivo use. Oligonucleotides. Dec. 2008;18(4):305-319.

Beloglazova, et al. A novel family of sequence-specific endoribonucleases associated with the clustered regularly interspaced short palindromic repeats. J Biol Chem. Jul. 18, 2008;283(29):20361-71. doi: 10.1074/jbc.M803225200. Epub May 15, 2008.

Bohacova et al. Protected 5-(hydroxymethyl)uracil nucleotides bearing visible-light photocleavable groups as building blocks for polymerase synthesis of photocaged DNA. Org Biomol Chem 16:1527-1535 (2018). First published Feb. 2, 2018. DOI: 10.1039/C8OB00160J.

Brinkman et al. Easy quantification of template-directed CRISPR/Cas9 editing. Supplementary Data. Nucleic Acids Research 46(10):e58 (2018). Published online Mar. 10, 2018. doi: 10.1093/nar/gky164.

Brinkman et al. Easy quantification of template-directed CRISPR/Cas9 editing. Nucleic Acids Research 46(10):e58 (2018). Published online Mar. 10, 2018. doi: 10.1093/nar/gky164. 9 pages.

Brinkman et al. Easy quantitative assessment of genome editing by sequence trace decomposition. Nucleic Acids Research 42(22):e168 (Dec. 16, 2014). Published online Oct. 9, 2014.

Chakrabarti et al. Target-Specific Precision of CRISPR-Mediated Genome Editing. Molecular Cell 73:699-713 (Feb. 21, 2019). DOI: https://doi.org/10.1016/j.molcel.2018.11.031.

Chang et al. Mixed Sequence Reader: A Program for Analyzing DNA Sequences with Heterozygous Base Calling. The Scientific World Journal, vol. 2012, Article ID 365401. Copyright 2012. doi: 10.1100/2012/365104. 10 pages.

Chari et al. Unraveling CRISPR-Cas9 genome engineering parameters via a library-on-library approach. Nature Methods Advance Online Publication Published Online Jul. 13, 2015. 7 pages. doi: 10.1038/NMETH.3473.

Chen et al. Dual sgRNA-directed gene knockout using CRISPR/Cas9 technology in Caenorhabditis elegans. Scientific Reports 4:7581 (Dec. 22, 2014). 7 pages.

Chen et al. Chemical conversion of a DNA-binding protein into a site-specific nuclease. Science 237(4819):1197-1201 (Sep. 4, 1987).

Chen et al. Functional disruption of the dystrophin gene in rhesus monkey using CRISPR/Cas9. Hum Mol Genet. Jul. 1, 2015; 24(13): 3764-3774. Published online Apr. 9, 2015. doi: 10.1093/hmg/ddv120 . . . .

Chen et al. Nuclease activity of 1, 10-phenanthroline-copper. New conjugates with low molecular weight targeting ligands. Bioconjugate Chem 4(1):69-77 (1993). DOI: https://doi.org/10.1021/bc00019a010.

CRISPR gRNA Design tool. ATUM. (Website.) One page. Accessed Oct. 31, 2018 at URL: (https://www.atum.bio/eCommerce/cas9/input).

CRISPResso: Analysis of CRISPR-Cas9 genome editing outcomes from deep sequencing data. Retrieved Aug. 6, 2018 at URL: http://crispresso.rocks/help. 12 pages.

(56) References Cited

OTHER PUBLICATIONS

De Koker et al. Polymeric multilayer capsules delivering biotherapeutics. Adv Drug Deliv Rev 63(9):748-61 (Aug. 14, 2011). Epub Apr. 12, 2011. DOI: 10.1016/j.addr.2011.03.014.

Dehairs et al. CRISP-ID: decoding CRISPR mediated indels by Sanger sequencing. Scientific Reports 6:28973 (Jul. 1, 2016). DOI: 10.1038/srep28973. 5 pages.

Dellinger et al. Solid-phase chemical synthesis of phosphonoacetate and thiophosphonoacetate oligodeoxynucleotides. J Am Chem Soc 125(4):940-950 (2003). Epub Jan. 3, 2003. DOI: 10.1021/ja027983f.

Dellinger et al. Streamlined process for the chemical synthesis of RNA using 2'-O-thionocarbamate-protected nucleoside phosphoramidites in the solid phase. J Am Chem Soc 133(30):11540-11556 (Jun. 20, 2011). doi: 10.1021/a201561z.

Design sgRNAs for CRISPRko (*S. pyogenes* and *S. aureus*). Broad Institute, Genetic Perturbation Platform (GPP) Web Portal. 2 pages. Accessed Oct. 31, 2018 at URL:https://portals.broadinstitute.org/gpp/public/analysis-tools/sgrna-design.

Dharmacon(TM) Edit-R(TM) CRISPR-Cas9 Gene Editing Products. GE Healthcare. (Mar. 2017).

Doench et al. Optimized sgrNA design to maximize activity and minimize off-target effects of crisPr-cas9. Nature Biotechnology 34(2):184-191 (Feb. 2016). Advance Online Publication published online Jan. 18, 2016. doi: 10.1038/nbt/3437.

Doench et al. Rational design of highly active sgRNAs for CRISPR-Cas9-mediated gene inactivation. Nat Biotechnol 32(12):1262-1267 (Dec. 2014). doi:10.1038/nbt.3026.

Dominguez, et al. Beyond editing: repurposing CRISPR-Cas9 for precision genome regulation and interrogation. Nature reviews Molecular cell biology 17.1 (2016): 5.

Endres et al. Self-assembled biodegradable amphiphilic PEG-PCL-IPEI triblock copolymers at the borderline between micelles and nanoparticles designed for drug and gene delivery. Biomaterials 32(30):7721-7731 (2011). Epub Jul. 22, 2011.doi: 10.1016/j.biomaterials.2011.06.064.

Erard et al. A CRISPR Resource for Individual, Combinatorial, or Multiplexed Gene Knockout. Mol Cell 67(2):348-354.e4 (Jul. 20, 2017). Correction published in Mol Cell 67(6):1080. (Sep. 21, 2017).

Fagerlund, et al. The CPf1 CRISPR-Cas protein expands genome-editing tools. Genome Biol. Nov. 17, 2015;16:251. doi: 10.1186/s13059-015-0824-9.

Ferenczi et al. Efficient targeted DNA editing and replacement in Chlamydomonas reinhardtii using Cpf1 ribonucleoproteins and single-stranded DNA.PNAS 114(51):13567-13572 (Dec. 19, 2017). Published ahead of print Dec. 19, 2017. URL: http://www.pnas.org/cgi/doi/10.1073/pnas.1710597114.

```
{'azimuth': 0.26953322761152265,
 'azimuth_display': '0.270',
 'chr_start': 65662059,
 'cutsite': 65662091,
 'exclude_reason': 'Azimuth score too low (0.269533 < 0.400000)',
 'exon': 'Exon 3',
 'guide': u'AGGCCUGGGCUGGCUCUGCC',
 'id': 184030497,
 'offtarget': [0, 2, 10, 80, 627],
 'pam_right': True,
 'recommendation': [False, True, False, False],
 'target': u'AGGCCTGGGCTGGCTCTGCC'},
{'azimuth': 0.43603879353943326,
 'azimuth_display': '0.436',
 'chr_start': 65662065,
 'cutsite': 65662083,
 'exclude_reason': '',
 'exon': 'Exon 3',
 'guide': 'UCCCCUGGCAGAGCCAGCCC',
 'id': 184030500,
 'offtarget': [0, 0, 3, 60, 501],
 'pam_right': False,
 'pick_order': 1,
 'recommendation': [True, True, True, True],
 'target': 'TCCCCTGGCAGAGCCAGCCC'},
{'azimuth': 0.39264677738557313,
 'azimuth_display': '0.393',
 'chr_start': 65662049,
 'cutsite': 65662081,
 'exclude_reason': 'Azimuth score too low (0.392647 < 0.400000)',
 'exon': 'Exon 3',
 'guide': u'UAGGGGCCAGAGGCCUGGGC',
 'id': 184030495,
 'offtarget': [0, 0, 41, 79, 535],
 'pam_right': True,
 'recommendation': [True, True, False, True],
 'target': u'TAGGGGCCAGAGGCCTGGGC'},
{'azimuth': 0.28614525667750368,
 'azimuth_display': '0.286',
 'chr_start': 65662045,
 'cutsite': 65662077,
 'exclude_reason': 'Azimuth score too low (0.286145 < 0.400000)',
 'exon': 'Exon 3',
 'guide': u'CACAUAGGGGCCAGAGGCCU',
 'id': 184030493,
 'offtarget': [0, 1, 4, 14, 293],
 'pam_right': True,
 'recommendation': [True, True, False, False],
 'target': u'CACATAGGGGCCAGAGGCCT'},
```

| ≡ RECOMMENDED GUIDES | | ≡ ALL GUIDES |
|---|---|---|
| GENOME<br>Homo sapiens<br>Gencode Release 26 (GRCh38.p10) ⓘ | GENE<br>RELA : ENST00000406246 (primary)<br>HAVANA ⓘ | NUCLEASE<br>SpCas9 |

We found 43 targets and recommend these 4 top-ranked guide RNAs for knocking out — 910
the RELA gene ⓘ in the Homo sapiens genome ⓘ

940

+ STRAND   EXON 3 -151BP
           CDS
930 — STRAND

← RELA →

65,661,900  65,661,950  65,662,000  65,662,050  65,662,100  65,662,150  65,662,200

RECOMMENDED GUIDES FOR KNOCKOUT ⓘ

| RANK ⓘ | SEQUENCE ⓘ | EARLY CODING REGION ⓘ | COMMON EXON ⓘ | HIGH ACTIVITY ⓘ | MINIMAL OFF TARGETS ⓘ | |
|---|---|---|---|---|---|---|
| 1 | UCCCCUGGGAGACCCACCCC | ⓘ | ⓘ | ⓘ | ⓘ | ✓ SELECTED |
| 2 | GAUCUCCACAUAGGGGCCAG | ⓘ | ⓘ | ⓘ | ⓘ | ✓ SELECTED |
| 3 | CCAGGCCUCUGGCCCCUAUG | ⓘ | ⓘ | ⓘ | ⓘ | ✓ SELECTED |
| 4 | GCUCAAUGAUCUCCACAUAG | ⓘ | ⓘ | ⓘ | ⓘ | ✓ SELECTED |

920

⊕ SHARE  ⊕ EXPORT      ⓘ WHY OUR RECOMMENDATIONS?   CONTINUE WITH 4 GUIDES >

| RANK | SEQUENCE | EARLY CODING REGION | COMMON EXON | HIGH ACTIVITY | MINIMAL OFF TARGETS | |
|---|---|---|---|---|---|---|
| 1 | UCCCCUGGGAGACCCACCCC | ⊘ | ⊘ | ⊘ | ⊘ | ✓ SELECTED |
| 2 | GAUCUCCACAUAGGGCCAG | ⊘ | ⊘ | ⊘ | ⊘ | ✓ SELECTED |
| 3 | CCAGGCCUCUGGCCCCUAUG | ⊘ | ⊘ | ⊘ | ⊘ | ✓ SELECTED |
| 4 | GCUCAAUGAUCUCCACAUAG | ⊘ | ⊘ | ⊘ | ⊘ | ✓ SELECTED |

GENOME: Homo sapiens Gencode Release 26 (GRCh38.p10)

GENE: RELA: ENST00000406246 (primary) HAVANA

NUCLEASE: SpCas9

We found 43 targets and recommend these 4 top-ranked guide RNAs for knocking out the RELA gene in the Homo sapiens genome

RECOMMENDED GUIDES FOR KNOCKOUT

⊙ WHY OUR RECOMMENDATIONS?   CONTINUE WITH 4 GUIDES >

SHARE  EXPORT

FIG. 9C

≡ RECOMMENDED GUIDES | ≡ ALL GUIDES

GENOME
Homo sapiens
Gencode Release 26 (GRCh38.p10)

GENE
RELA : ENST00000406246 (primary)
HAVANA

NUCLEASE
SpCas9

We found 43 targets and recommend these 4 top-ranked guide RNAs for knocking out the RELA gene in the Homo sapiens genome

```
                                                                    Rank 1
                                                                    Target: TCCCCTGGCAGAGCCAGCCC
                                                                    Outside: 65,662,063
                                                                    Exon: Exon 3
                                                                    On Target Score: 0.436
                                                                    Off Targets: 0.0.3.60.501
                                                                                                    944

65,661,900  65,661,950  65,662,000  65,662,050  65,662,089  65,662,100  65,662,150  65,662,200
                                                 65,662,050
+ STRAND    EXON 3 -151BP
            CDS
930
- STRAND
                                    RELA
```

RECOMMENDED GUIDES FOR KNOCKOUT

| RANK | SEQUENCE | EARLY CODING REGION | COMMON EXON | HIGH ACTIVITY | MINIMAL OFF TARGETS | |
|------|----------|---------------------|-------------|---------------|---------------------|---|
| 1 | UCCCCUGGGAGACCCACCCC | ⊘ | ⊘ | ⊘ | ⊘ | ✓ SELECTED |
| 2 | GAUCUCCACAUAGGGGCCAG — 922 | ⊘ | ⊘ | ⊘ | ⊘ | ✓ SELECTED |
| 3 | CCAGGCCUCUGGCCCCUAUG | ⊘ | ⊘ | ⊘ | ⊘ | ✓ SELECTED |
| 4 | GCUCAUGAUCUCCACAUAG | ⊘ | ⊘ | ⊘ | ⊘ | ✓ SELECTED |

920

⊘ WHY OUR RECOMMENDATIONS?  [CONTINUE WITH 4 GUIDES >]

SHARE  EXPORT

≡ RECOMMENDED GUIDES ≡ ALL GUIDES

GENOME
Homo sapiens
Gencode Release 26 (GRCh38.p10)

GENE
RELA: ENST00000406246 (primary)
HAVANA

NUCLEASE
SpCas9

Contig: chr11    ENST00000406246 (primary) ▾    Exon 3 - 151bp

| RANK | SEQUENCE | CUTSITE | EXON | ON TARGET SCORE | OFF TARGETS | |
|---|---|---|---|---|---|---|
| 15 | GAUGGUGGGGUGGUCUUGG | 65,661,957 | EXON 3 | 0.477 | 0,0,9,52,615 | SELECT |
| 16 | GCUGACCUUGAUGGUGGGU | 65,661,948 | EXON 3 | 0.519 | 0,0,3,27,312 | SELECT |
| 17 | UGCUGACCUUGAUGGUGGGG | 65,661,947 | EXON 3 | 0.460 | 0,0,0,38,287 | SELECT |
| 18 | CAGUGCUGACCUUGAUGUG | 65,661,944 | EXON 3 | 0.558 | 0,0,1,19,172 | SELECT |
| 19 | GCAGUGCUGACCUUGAUGU | 65,661,943 | EXON 3 | 0.540 | 0,0,1,11,125 | SELECT |
| 20 | CCCAGUGCUGACCUUGAUGG | 65,661,942 | EXON 3 | 0.492 | 0,0,0,12,126 | SELECT |
| 21 | CAAGACCCACCCCACCAUCA | 65,661,942 | EXON 3 | 0.629 | 0,0,5,48,1173 | SELECT |

FIG. 9D

| | | ADDITIONAL GUIDES | | | |
|---|---|---|---|---|---|
| RANK ⊚ | SEQUENCE ⊚ | CUTSITE ⊚ | EXON ⊚ | ON TARGET SCORE ⊚ | OFF TARGETS ⊚ |
| - | GACACCGCAGCCCCAUUAGG | 65,662,115 | EXON 3 | 0.594 | 0,0,1,6,104 | SELECT |
| - | GGGGACACCGCAGCCCCAUU | 65,662,112 | EXON 3 | 0.471 | 0,0,1,27,265 | SELECT |
| - | AAUGGGGCUCGCGGUGUCCCC | 65,662,098 | EXON 3 | 0.388 | 0,0,1,27,265 | SELECT |

⊚ WHY OUR RECOMMENDATIONS? | CONTINUE WITH 4 GUIDES >

⊡ SHARE ⊞ EXPORT

METHODS AND SYSTEMS FOR GUIDE RNA DESIGN AND USE

CROSS-REFERENCE TO RELATED APPLICATIONS

This application is a continuation of U.S. application Ser. No. 16/418,893 filed on May 21, 2019, which is a continuation of International Application No. PCT/US2019/032735, filed on May 16, 2019, which claims priority to U.S. Provisional Application No. 62/672,437 filed May 16, 2018, all of which are hereby incorporated by reference in their entirety.

SEQUENCE LISTING

This application is being filed electronically via EFS-Web and includes an electronically submitted Sequence Listing in .txt format. The .txt file contains a sequence listing entitled "174774-00107 ST25.txt" created on Apr. 25, 2022, and is 18,545 bytes in size. The Sequence Listing contained in this .txt file is part of the specification and is hereby incorporated by reference herein in its entirety.

BACKGROUND

Engineered nuclease technologies designed to target and manipulate specific DNA sequences are rapidly being adopted as useful techniques for a number of different applications including genetic manipulation of cells and whole organisms, targeted gene deletion, replacement and repair, and insertion of exogenous sequences (transgenes) into the genome. Examples of genome editing techniques include zinc finger, transcription activator-like effector (TALE), and clustered regularly interspaced short palindromic repeats (CRISPR)/CRISPR-associated (Cas) ("CRISPR/Cas") systems.

The CRISPR/Cas system can be used as a gene editing tool in a plethora of different organisms to generate breaks at a target site and subsequently introduce mutations at the locus. Two main components can be needed for the gene editing process: an endonuclease like Cas enzyme and a short RNA molecule to recognize a specific DNA target sequence. Instead of engineering a nuclease enzyme for every DNA target, the CRISPR/Cas system can rely on customized short RNA molecules to recruit the Cas enzyme to a new DNA target site. Examples of Cas enzymes include Cas9 and Cpf1.

The CRISPR/Cas system can be used in prokaryotic and eukaryotic systems for genome editing and transcriptional regulation. In some cases, the CRISPR/Cas system can yield unwanted off-target genome editing and varied editing efficiency across different gene targets.

SUMMARY

The present disclosure describes technologies relating to designing one or more oligonucleotides (e.g. RNA molecules) that recognize respective target oligonucleotide sequences for CRISPR/Cas mediated gene manipulation, and more specifically, the present disclosure describes methods of determining an off-target value across the entire genome of a species of interest to minimize off-target genome editing and improve editing efficiency. The present disclosure describes software and hardware configurations for performing the design and validation of such oligonucleotides.

Described herein, in certain embodiments, are methods for identifying a set of guide RNAs (gRNAs) that are hybridizable to a genomic region of interest in a genome comprising: designing a set of gRNAs where each gRNA in the set of gRNAs: is hybridizable to a target site from a plurality of target sites within the genomic region of interest that is at least 30 bases apart from a different target sites in the plurality of target sites of at least one other guide RNA from the set of guide RNAs. In some embodiments, the target site is at most 170 bases apart from the different target site.

In some embodiments, the sequence of at least one gRNA in the set of gRNAs is complementary to the genomic region of interest. In some embodiments, the sequence of at least one gRNA in the set of gRNAs is partially complementary to the genomic region of interest. In some embodiments, the sequence of the at least one gRNA in the set of gRNAs partially complementary to the genomic region of interest comprises 1, 2, 3, 4, 5, or more than 5 mismatches relative to the genomic region of interest. In some embodiments, each gRNA in the set of gRNAs is from about 17 to about 42 bases in length. In some embodiments, each gRNA in the set of gRNAs is about 20 bases in length. In some embodiments, each gRNA in the set of gRNAs comprises a guide sequence of about 20 bases and further comprises a constant region of from about 22 to about 80 bases in length. In some embodiments, the guide sequence of each gRNA in the set of gRNAs selectively hybridizes to the genomic region of interest. In some embodiments, each gRNA in the initial set of gRNAs is about 100 bases in length.

In some embodiments, the genomic region of interest comprises a coding region of a gene. In some embodiments, the genomic region of interest comprises an exon of the gene. In some embodiments, the genomic region of interest comprises a family of genes. In some embodiments, the genomic region of interest comprises one or more coding regions from the family of genes. In some embodiments, the genomic region of interest comprises a non-coding region of the genome. In some embodiments, the non-coding region is a regulatory element. In some embodiments, the regulatory element is a cis-regulatory element or a trans-regulatory element. In some embodiments, the cis-regulatory element is selected from the group consisting of: a promoter, an enhancer, and a silencer.

In some embodiments, the genomic region of interest spans greater than 5 kbs, greater than 10 kbs, greater than 15 kbs, greater than 20 kbs, greater than 50 kbs, or greater than 100 kbs. In some embodiments, the set of gRNAs comprises at least 1, at least 2, at least 3, or at least 4 gRNAs. In some embodiments, at least one gRNA from the set of guide RNAs comprises a modification. In some embodiments, the modification is selected from the group consisting of: 2'-O—C1-4alkyl such as 2'-O-methyl (2'-OMe), 2'-deoxy (2'-H), 2'-O—C1-3alkyl-O—C1-3alkyl such as 2'-methoxyethyl (2'-MOE), 2'-fluoro (2'-F), 2'-amino (2'-NH2), 2'-arabinosyl (2'-arabino) nucleotide, 2'-F-arabinosyl (2'-F-arabino) nucleotide, 2'-locked nucleic acid (LNA) nucleotide, 2'-unlocked nucleic acid (ULNA) nucleotide, a sugar in 1 form (1-sugar), and 4'-thioribosyl nucleotide. In some embodiments, the modification is an internucleotide linkage modification selected from the group consisting of: phosphorothioate, phosphonocarboxylate, thiophosphonocarboxylate, alkylphosphonate, and phosphorodithioate. In some embodiments, the modification is selected from the group consisting of: 2-thiouracil (2-thioU), 2-thiocytosine (2-thioC), 4-thiouracil (4-thioU), 6-thioguanine (6-thioG), 2-aminoadenine (2-aminoA), 2-aminopurine, pseudouracil, hypoxanthine, 7-deazaguanine, 7-deaza-8-azaguanine, 7-deazaadenine, 7-deaza-8-azaadenine, 5-methylcytosine (5-methylC), 5-methyluracil (5-methylU), 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil (5-allylU), 5-allylcytosine (5-allylC), 5-aminoallyluracil (5-aminoallylU), 5-aminoallyl-cytosine (5-aminoallylC), an abasic nucleotide, Z base, P base, Unstructured Nucleic Acid (UNA), isoguanine (isoG), isocytosine (isoC), and 5-methyl-2-pyrimidine.

In some embodiments, a target site of the plurality of target sites is adjacent to a PAM site for a nuclease selected from the group consisting of: Cas9, C2c1, C2c3, and Cpf1. In some embodiments, the nuclease is Cas9. In some embodiments, the nuclease is inactivated Cas9. In some embodiments, the set of gRNAs are designed to knock-out a gene in the genomic region of interest in a cell. In some embodiments, the cell is selected from the group consisting of: human primary cells, human immortalized cells, human induced pluripotent stem cells, mouse embryonic stem cells, and Chinese hamster ovary cells. In some embodiments, the designing is performed by a computer. In some embodiments, described herein, are kits comprising a set of guide RNAs (gRNAs), each gRNA in the set of gRNAs designed by any of the methods described herein.

Described herein, in certain embodiments, are kits comprising a set of gRNAs that are hybridizable to a genomic region of interest in a genome, wherein each gRNA in the set of gRNAs: is hybridizable to a target site from a plurality of target sites within the genomic region of interest that is at least 30 bases apart from a different target site in the plurality of target sites of at least one other guide RNA from the set of guide RNAs. In some embodiments, the target site is at most 170 bases apart from the different target site. In some embodiments, the set of gRNAs comprises at least 2, at least 3, or at least 4 gRNAs. In some embodiments, the kit further comprises one or more nucleases selected from the group consisting of Cas9, C2c1, C2c3, and Cpf1. In some embodiments, the kit further comprises a plurality of sets of gRNAs, each set of gRNA hybridizable to a different genomic region of interest in the genome. In some embodiments, the one or more nucleases are coupled to at least one gRNA.

Described herein, in certain embodiments, are methods for selecting one or more guide RNAs (gRNAs) for hybridizing a gene of a genome of a species comprising: for each of a plurality of guide RNAs of an initial set of guide RNAs that hybridize to the gene, calculating an off-target value by enumerating a number of mismatches to potential guide RNA hybridizing sites in the genome. In some embodiments, each gRNA in the plurality of gRNAs is 100 bases in length. In some embodiments, about 20 bases of each gRNA in the plurality of gRNAs hybridizes to different target site within a genomic region of interest. In some embodiments, the number of mismatches is 0. In some embodiments, the number of mismatches is 1. In some embodiments, the number of mismatches is 2. In some embodiments, the number of mismatches is 3. In some embodiments, the calculating enumerates an aggregate sum of the number of mismatches for each gRNA of the initial set of guide RNAs. In some embodiments, the calculating organizes the number of mismatches into shards.

In some embodiments, the off-target value is calculated against a reference genome. In some embodiments, the reference genome is a human reference genome. In some embodiments, the reference genome is selected from the group consisting of: *Homo sapiens, Mus musculus, Cricetulus griseus, Rattus Norvegicus, Danio rerio,* and *Caenorhabditis elegans*. In some embodiments, the off-target value is determined over 1,000,000 bp of a reference genome or across a reference genome. In some embodiments, the off-target value is calculated against a database of binding sites of a nuclease. In some embodiments, the nuclease is selected from the group consisting of: Cas9, C2c1, C2c3, and Cpf1. In some embodiments, the nuclease is Cas9. In some embodiments, the database comprises greater than 10,000, greater than 50,000, greater than 100,000, greater than 150,000, greater than 200,000, greater than 250,000, greater than 300,000, greater than 350,000, greater than 400,000, greater than 450,000, greater than 500,000, greater than 550,000, greater than 600,000, greater than 650,000, greater than 700,000, greater than 750,000, greater than 800,000, greater than 850,000, greater than 900,000, greater than 950,000, or greater than 1,000,000 binding sites of the nuclease. In some embodiments, the database of nuclease binding sites comprises greater than 25 million, greater than 50 million, greater than 75 million, greater than 100 million, greater than 125 million, greater than 150 million, greater than 175 million, greater than 200 million, greater than 225 million, greater than 250 million, greater than 275 million, or greater than 300 million binding sites of the nuclease. In some embodiments, the calculating of the off-target value by enumerating the number of mismatches is performed by a computer.

Described herein, in certain embodiments, are methods for designing one or more guide RNAs (gRNAs) for hybridizing to a gene of a genome of a species comprising: selecting a transcript from a plurality of transcripts of the gene; and identifying an initial set of gRNAs, wherein each gRNA in the initial set of gRNAs hybridizes to different target sites in the gene of the selected transcript. In some embodiments, each gRNA in the initial set of gRNAs is from about 17 to about 42 bases in length. In some embodiments, each gRNA in the initial set of gRNAs is about 20 bases in length. In some embodiments, each gRNA in the initial set of gRNAs comprises a guide sequence of about 20 bases and a constant region of from about 22 to about 80 bases in length. In some embodiments, the guide sequence each gRNA in the initial set of gRNAs selectively hybridizes a target site. In some embodiments, each gRNA in the initial set of gRNAs is about 100 bases in length. In some embodiments, the selected transcript is a most abundant transcript of the gene in a database. In some embodiments, the selected transcript is a longest transcript of the plurality of transcripts of the gene.

In some embodiments, the method further comprises selecting a coding region in the gene present in the selected transcript. In some embodiments, the selected coding region is an early position exon. In some embodiments, the early position exon is in a first half of the gene. In some embodiments, the early position exon is a first, second, third, fourth, fifth, or sixth exon of the gene. In some embodiments, the selected coding region is a selected exon that is a transcript with the highest abundance in the plurality of transcripts of the gene. In some embodiments, the selected exon is longer than one or more other exons in the plurality of transcripts. In some embodiments, the selected exon is at least 50 bp, at least 55 bp, at least 60 bp, at least 65 bp, at least 70 bp, or at least 75 bp. In some embodiments, the selected exon is selected based on both length and abundance in the plurality of transcripts.

In some embodiments, the method further comprises determining an off-target value for each gRNA of the initial set of gRNAs. In some embodiments, the off-target value is determined across the genome of the species. In some embodiments, the genome is a reference genome of the species. In some embodiments, the reference genome of the species is a complete reference assembly containing chromosomes and unlocalized contigs. In some embodiments, the method further comprises determining the off-target value by enumerating a number of mismatches for each gRNA in the initial set of gRNAs as compared to a plurality of target sites in the genome. In some embodiments, the plurality of target sites comprises all possible Cas nuclease binding sites across the genome. In some embodiments, the plurality of target site comprises at least 1000, 10,000, 100,000, 200,000, 300,000, 400,000, 500,000, 600,000, 700,000, 800,000, 900,000, 1,000,000, 2,000,000, or 3,000,000 target sites. In some embodiments, the plurality of target site comprises at least 100,000,000, 200,000,000, 300,000,000, 400,000,000, 500,000,000, 600,000,000, 700,000,000, 800,000,000, 900,000,000, 1,000,000,000, or 1,500,000,000 target sites. In some embodiments, the enumerating comprises determining an off-target hybridization region for each gRNA of the initial set of guide RNAs with 0, 1, 2, 3, or 4 numbers of mismatches.

In some embodiments, a target site of the different target sites is adjacent to a PAM site for a nuclease selected from the group consisting of: Cas9, C2c1, C2c3, and Cpf1. In some embodiments, the nuclease is Cas9. In some embodiments, the PAM site is NGG. In some embodiments, the nuclease is an inactivated Cas. In some embodiments, the species is selected from the group consisting of: *Homo sapiens, Mus musculus, Cricetulus griseus, Rattus Norvegicus, Danio rerio*, and *Caenorhabditis elegans*.

In some embodiments, the method further comprises selecting a subset of guide RNAs from the initial set of gRNAs based on an on-target efficiency threshold value and an off-target threshold value. In some embodiments, the on-target efficiency threshold value for each guide RNA of the initial set of gRNAs is determined by calculating an azimuth score. In some embodiments, the azimuth score is greater than 0.4. In some embodiments, the identifying is based on thresholds of the azimuth score and the off-target hybridizing value. In some embodiments, the initial set of gRNAs knocks-out the gene in a cell. In some embodiments, the initial set of gRNAs knocks-in a mutation into the gene in a cell.

In some embodiments, the cell is selected from the group consisting of: human primary cells, human immortalized cells, human induced pluripotent stem cells, mouse embryonic stem cells, and Chinese hamster ovary cells. In some embodiments, at least one nucleotide from at least one guide RNA in the initial set of guide RNAs comprises a modification. In some embodiments, the modification is selected from the group consisting of: 2'-O—C1-4alkyl such as 2'-O-methyl (2'-OMe), 2'-deoxy (2'-H), 2'-O—C1-3alkyl-O—C1-3alkyl such as 2'-methoxyethyl (2'-MOE), 2'-fluoro (2'-F), 2'-amino (2'-NH2), 2'-arabinosyl (2'-arabino) nucleotide, 2'-F-arabinosyl (2'-F-arabino) nucleotide, 2'-locked nucleic acid (LNA) nucleotide, 2'-unlocked nucleic acid (ULNA) nucleotide, a sugar in 1 form (1-sugar), and 4'-thioribosyl nucleotide. In some embodiments, the modification is an internucleotide linkage modification selected from the group consisting of: phosphorothioate, phosphonocarboxylate, thiophosphonocarboxylate, alkylphosphonate, and phosphorodithioate. In some embodiments, the modification is selected from the group consisting of: 2-thiouracil (2-thioU), 2-thiocytosine (2-thioC), 4-thiouracil (4-thioU), 6-thioguanine (6-thioG), 2-aminoadenine (2-aminoA), 2-aminopurine, pseudouracil, hypoxanthine, 7-deazaguanine, 7-deaza-8-azaguanine, 7-deazaadenine, 7-deaza-8-azaadenine, 5-methylcytosine (5-methylC), 5-methyluracil (5-methylU), 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil (5-allylU), 5-allylcytosine (5-allylC), 5-aminoallyluracil (5-aminoallylU), 5-aminoallyl-cytosine (5-aminoallylC), an abasic nucleotide, Z base, P base, Unstructured Nucleic Acid (UNA), isoguanine (isoG), isocytosine (isoC), and 5-methyl-2-pyrimidine.

In some embodiments, the selecting and the identifying are performed by a computer. In some embodiments, each gRNA in the initial set of gRNAs is hybridizable to a target site that is at least 30 bases apart from the target site of at least one other guide RNA from the initial set of guide RNAs. In some embodiments, described herein, are kits comprising a set of guide RNAs (gRNAs), each gRNA in the set of gRNAs designed by any of the methods described herein.

Described herein, in certain embodiments, are method for editing a genomic region of interest, comprising: contacting a population of cells comprising the genomic region of interest with: (i) a set of gRNA comprising at least two gRNAs targeting the genomic region of interest and (ii) a nuclease; wherein an editing efficiency of the set of gRNA comprising at least two gRNAs is higher than an individual editing efficiency of each of the at least two gRNAs. In some embodiments, the genomic region of interest is a coding region of a gene. In some embodiments, the coding region is an exon of the gene. In some embodiments, the genomic region of interest is a non-coding region in a genome. In some embodiments, the non-coding region is a regulatory element. In some embodiments, the regulatory element is a cis-regulatory element or a trans-regulatory element. In some embodiments, the cis-regulatory element is selected from the group consisting of: a promoter, an enhancer, and a silencer. In some embodiments, the method further comprises contacting the cell with a donor polynucleotide. In some embodiments, the donor polynucleotide comprises a point mutation, allele, tag or exogenous exon relative to a wild-type genotype of the cell.

In some embodiments, the editing efficiency is a proportion of cells in the population of cells comprising a non-wild type genotype after the contacting. In some embodiments, the non-wild type genotype is a knock-out of a gene. In some embodiments, the non-wild type genotype is an insertion or a deletion relative to a wild type genotype. In some embodiments, at least 50%, at least 60%, at least 70%, at least 80%, at least 90%, or at least 95% of the cells in the population of cells comprise the non-wild type genotype. In some embodiments, each gRNA of the at least two gRNAs hybridize to different target sites in the genomic region of interest. In some embodiments, each gRNA of the at least two gRNAs is hybridizable to a target site that is at least 30 bases apart from the target site of at least one other guide RNA from the set of guide RNAs.

In some embodiments, the method further comprises introducing a plurality of sets of gRNA targeting a plurality of genomic regions of interest. In some embodiments, each of the plurality of sets of gRNA is contacted with each of a plurality of subsets of the population of cells. In some embodiments, each of the plurality of sets of gRNA target a different genomic region of interest in the plurality of genomic regions of interest. In some embodiments, at least 50%, at least 60%, at least 70%, at least 80%, at least 90%, or at least 95% of the cells in at least 50% of the plurality of subsets of the population of cells comprise a non-wild type genotype. In some embodiments, at least 50%, at least 60%, at least 70%, at least 80%, at least 90%, or at least 95% of the cells in at least 70% of the plurality of subsets of the population of cells comprise a non-wild type genotype. In some embodiments, at least 50%, at least 60%, at least 70%, at least 80%, at least 90%, or at least 95% of the cells in at least 90% of the plurality of subsets of the population of cells comprise a non-wild type genotype.

In some embodiments, the method further comprises screening the population of cells for a phenotype.

Described herein, in certain embodiments, are computer systems for designing one or more guide RNAs (gRNAs) for hybridizing to a gene of a genome of a species comprising: one or more computer processors; and a non-transient a computer readable medium comprising instructions operable, when executed by the one or more computer processors, to cause the system to: select a transcript from a plurality of transcripts of the gene, and identify an initial set of gRNAs that hybridize to different target sites from a plurality of target sites within in the gene of the selected transcript. In some embodiments, each gRNA in the initial set of gRNAs is from about 17 to about 42 bases in length. In some embodiments, each gRNA in the initial set of gRNAs is about 20 bases in length. In some embodiments, each gRNA in the initial set of gRNAs comprises a guide sequence of about 20 bases and further comprises a constant region of from about 22 to about 80 bases in length. In some embodiments, the guide sequence of each gRNA in the initial set of gRNAs selectively hybridizes to the gene. In some embodiments, each gRNA in the initial set of gRNAs is about 100 bases in length. In some embodiments, the selected transcript is a most abundant transcript of the gene in a database. In some embodiments, the selected transcript is a longest transcript of the plurality of transcripts of the gene.

In some embodiments, the instructions are further operable to cause the system to select a coding region in the gene present in the selected transcript, thereby selecting a selected coding region. In some embodiments, the selected coding region is an early position exon. In some embodiments, the early position exon is in a first half of the gene. In some embodiments, the early position exon is a first, second, third, fourth, fifth, or sixth exon of the gene. In some embodiments, the selected coding region is a selected exon that a transcript with the highest abundance in the plurality of transcripts of the gene. In some embodiments, the selected exon is longer than one or more other exons in the plurality of transcripts. In some embodiments, the selected exon is at least 50 bp, at least 55 bp, at least 60 bp, at least 65 bp, at least 70 bp, or at least 75 bp. In some embodiments, the selected exon is selected based on both length and abundance in the plurality of transcripts. In some embodiments, the instructions are further operable to cause the system to determine an off-target value for each gRNA of the initial set of gRNAs. In some embodiments, the instructions are further operable to cause the system to determine across the genome of the species.

In some embodiments, the genome is a reference genome of the species. In some embodiments, the reference genome of the species is a complete reference assembly comprising chromosomes and unlocalized contigs. In some embodiments, the instructions are further operable to cause the system to determine the off-target value by enumerating a number of mismatches for each of the gRNAs in the initial set of gRNAs as compared to a plurality of target sites in the genome. In some embodiments, the plurality of target sites includes all possible Cas nuclease binding sites across the genome. In some embodiments, the plurality of target site comprises at least 1000, 10,000, 100,000, 200,000, 300,000, 400,000, 500,000, 600,000, 700,000, 800,000, 900,000, 1,000,000, 2,000,000, or 3,000,000 target sites. In some embodiments, the plurality of target site comprises at least 100,000,000, 200,000,000, 300,000,000, 400,000,000, 500, 000,000, 600,000,000, 700,000,000, 800,000,000, 900,000, 000, 1,000,000,000, or 1,500,000,000 target sites. In some embodiments, the enumerating comprises determining an off-target hybridization region for each gRNA of the initial set of guide RNAs with 0, 1, 2, 3, or 4 numbers of mismatches. In some embodiments, a target site of the plurality of target sites is adjacent to a PAM site for a nuclease selected from the group consisting of: Cas9, C2c1, C2c3, and Cpf1. In some embodiments, the nuclease is Cas9. In some embodiments, the PAM site is NGG. In some embodiments, the species is selected from the group consisting of: *Homo sapiens, Mus musculus, Cricetulus griseus, Rattus Norvegicus, Danio rerio*, and *Caenorhabditis elegans*.

In some embodiments, the instructions are further operable to cause the system to select a subset of guide RNAs from the initial set of gRNAs based on an on-target efficiency threshold value and an off-target threshold value. In some embodiments, the on-target efficiency threshold value for each guide RNA of the initial set of gRNAs is determined by calculating an azimuth score. In some embodiments, the azimuth score is greater than 0.4. In some embodiments, the instructions are further operable to cause the system to identify the initial set of gRNAs based on thresholds of the azimuth score and the off-target hybridizing value. In some embodiments, at least one nucleotide from at least one guide RNA in the initial set of guide RNAs comprises a modification. In some embodiments, the modification is selected from the group consisting of: 2'-O—C1-4alkyl such as 2'-O-methyl (2'-OMe), 2'-deoxy (2'-H), 2'-O—C1-3alkyl-O—C1-3alkyl such as 2'-methoxyethyl (2'-MOE), 2'-fluoro (2'-F), 2'-amino (2'-NH2), 2'-arabinosyl (2'-arabino) nucleotide, 2'-F-arabinosyl (2'-F-arabino) nucleotide, 2'-locked nucleic acid (LNA) nucleotide, 2'-unlocked nucleic acid (ULNA) nucleotide, a sugar in 1 form (1-sugar), and 4'-thio-ribosyl nucleotide. In some embodiments, the modification is an internucleotide linkage modification selected from the group consisting of: phosphorothioate, phosphonocarboxylate, thiophosphonocarboxylate, alkylphosphonate, and phosphorodithioate. In some embodiments, the modification is selected from the group consisting of: 2-thiouracil (2-thioU), 2-thiocytosine (2-thioC), 4-thiouracil (4-thioU), 6-thioguanine (6-thioG), 2-aminoadenine (2-aminoA), 2-aminopurine, pseudouracil, hypoxanthine, 7-deazaguanine, 7-deaza-8-azaguanine, 7-deazaadenine, 7-deaza-8-azaadenine, 5-methylcytosine (5-methylC), 5-methyluracil (5-methylU), 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil (5-allylU), 5-allylcytosine (5-allylC), 5-aminoallyluracil (5-aminoallylU), 5-aminoallyl-cytosine (5-aminoallylC), an abasic nucleotide, Z base, P base, Unstructured Nucleic Acid (UNA), isoguanine (isoG), isocytosine (isoC), and 5-methyl-2-pyrimidine. In some embodiments, each gRNA in the set: is hybridizable to a different target site within a genomic region of interest; and is hybridizable to a target site that is at least 30 bases apart from the target site of at least one other guide RNA from the set of guide RNAs.

Described herein, in certain embodiments, are methods for designing one or more guide RNAs for hybridizing to a genomic region of an individual comprising: using the individual's genome, determining gRNA target site potentials; for each gRNA target site potential of the gRNA target site potentials, determining an off-target value for a prospective guide RNA; and identifying one or more guide RNAs with an improved utility index. In some embodiments, each gRNA of the one or more gRNAs is about 100 bases in length. In some embodiments, about 20 bases of each gRNA of the one or more gRNAs is hybridizable to each gRNA target site potential of the gRNA target site potentials. In some embodiments, the utility index is a therapeutic index. In some embodiments, the therapeutic index comprises reduction of off-target binding, increased on-target efficiency, increased knock-out efficiency, increased knock-in efficiency, or modulation of CRISPR interference. In some embodiments, the individual is a human. In some embodiments, the individual is afflicted with a condition. In some embodiments, the individual is part of a population cohort afflicted with one or more conditions. In some embodiments, the one or more conditions include one or more types of cancer. In some embodiments, the condition is a cancer.

In some embodiments, the one or more guide RNAs are designed to knock-out a gene in the genomic region of a cell of the individual. In some embodiments, the one or more guide RNAs are designed to knock-in a mutation in the genomic region of a cell of the individual. In some embodiments, the method further comprises editing a cell with the one or more guide RNAs with the improved utility index. In some embodiments, the determining of the gRNA target site potentials and the identifying of the one or more guide RNAs is performed by a computer.

Described herein, in certain embodiments, are methods for assessing off-target effect of a CRISPR agent on an individual comprising: using the individual's genome, determining, by a computer system, the off-target value of the CRISPR agent by enumerating a number of mismatches to potential target sites in the individual's genome. In some embodiments, the CRISPR agent is a therapeutic agent. In some embodiments, the CRISPR agent is a guide RNA (gRNA) that is about 100 bases in length. In some embodiments, the gRNA comprises 20 bases that are hybridizable to a target. In some embodiments, the number of mismatches is calculated independently for each of the 20 bases that are hybridizable to a target.

In some embodiments, the enumerating comprises separately enumerating at least two of 1, 2, 3, 4, or 5 numbers of mismatches from the potential target sites. In some embodiments, the number of potential target sites is at least 1000, 10,000, 100,000, 200,000, 300,000, 400,000, 500,000, 600,000, 700,000, 800,000, 900,000, 1,000,000, 2,000,000, or 3,000,000. In some embodiments, the method further comprises outputting a report that enumerates the number of mismatches to potential target sites in the individual's genome. In some embodiments, the outputting is displayed on a screen. In some embodiments, the assessing of the off-target effect of the CRISPR agent is used as a companion diagnostic.

Described herein, in certain embodiments, are methods for validating a prospective gRNA comprising: determining, on a computer system, a plurality of off-target sites for the prospective gRNA in a genome or part of the genome; calculating, using the computer system, an off-target value for the prospective gRNA for each off-target site in the plurality of off-target sites; and predicting, using the computer system, activity of the prospective gRNA using the off-target value. In some embodiments, the predicting lists a potential of on-target hybridization sites or off-target hybridization sites. In some embodiments, the genome or part of the genome is over 1,000,000 bps. In some embodiments, the off-target value is determined by calculating a number of mismatches for the gRNA to a plurality of off-target sites. In some embodiments, the number of mismatches is 0, 1, 2, 3, and/or 4. In some embodiments, the plurality of off-target sites comprises at least 100,000,000 off-target sites.

Described herein, in certain embodiments, are computer systems comprising: a user interface system configured to select of a species of interest and a gene of interest from the species of interest; a design module integrated with the user interface configured to identify one or more guide RNA (gRNA) sequences for the gene of interest; an output system configured to display selected gRNAs; and an activation unit configured to initiate synthesis by an RNA synthesizer of the one or more gRNAs. In some embodiments, each gRNA is about 20 bases in length. In some embodiments, the user interface system includes a selection of over 100, 1000, 10,000, 100,000, 500,000 different reference genomes. In some embodiments, the design module is configured to select gRNAs based on off-target value and on-target efficiency score. In some embodiments, the design module is configured to access to reference genomes in the cloud. In some embodiments, the design module is configured to access to more than 10,000, 20,000, 30,000, 40,000, 50,000, 60,000, 70,000, 80,000, 90,000, 100,000, 110,000, or 120,000 reference genomes. In some embodiments, the user interface comprises: a genomic data receiving module for obtaining input of an individual's genome. In some embodiments, the genomic data receiving module is configured to obtain the individual's genome from a server or from a file uploaded by a user.

Described herein, in certain embodiments, are systems comprising: an interface configured to provide a user with access to more than 10,000 reference genomes; a software configured to select one or more guide RNAs for a gene in any one of the more than 50,000 reference genomes; and an output system configured to display selected guide RNAs. In some embodiments, the system comprises more than 20,000, 30,000, 40,000, 50,000, 60,000, 70,000, 80,000, 90,000, 100,000, 110,000, or 120,000 reference genomes. In some embodiments, the system further comprises a script configured to activate and initiate synthesis of the at least one or more guide RNAS.

Described herein, in certain embodiments, are methods for designing a guide RNA (gRNA) comprising: identifying, by a computer system, a primary transcript of a gene; identifying, by a computer system, a common exon between the primary transcript and a plurality of alternative transcripts; identifying, by a computer system, a nuclease target site within the common exon; calculating, by a computer system, a number of off-target binding sites in a reference genome sequence for a nuclease, thereby yielding a calculated number of nuclease off-target binding sites; calculating, by a computer system, an on-target efficiency score, thereby yielding a calculated on-target efficiency score; and outputting, by a computer system, at least one gRNA sequence wherein the at least one gRNA sequence comprises a sequence for which the calculated on-target efficiency is above a threshold and the calculated number of nuclease off-target binding sites is zero. In some embodiments, the method further comprises directing a synthesis of a nucleic acid that has partial complementarity to the target site. In some embodiments, described herein, are kits comprising a set of guide RNAs (gRNAs), each gRNA in the set of gRNAs designed by any of the methods described herein.

Described herein, in certain embodiments, are systems for processing a biopolymer synthesis request from a user over a network, comprising: a communications interface configured to communicate with a digital computer of the user over the network; a reference genome database configured to store one or more reference genomes; and a computer comprising one or more computer processors operatively coupled to the communications interface and the database, wherein the one or more computer processors are individually or collectively configured to: (a) receive from the communications interface over the network, the biopolymer synthesis request from the digital computer of the user, which biopolymer synthesis request comprises target genomic information; (b) process the target genomic information against the one or more reference genomes from the database to identify a target sequence corresponding to the target genomic information; (c) execute an algorithm to generate a first set of guide ribonucleic acid (gRNA) sequences that are at least partially complementary to the target sequence, and calculate an off-target complementarity score for each of the gRNA sequences in the first set of gRNA sequences; (d) output a second set of gRNA sequences for display on a graphical user interface of the digital computer of the user, where each of the second set of gRNA sequences has a calculated off-target complementarity score below a threshold; and (e) receive from the digital computer of the user a selection of a given gRNA sequence from the second set of gRNA sequences.

In some embodiments, the one or more computer processors are individually or collectively programmed to direct the given gRNA sequence in a queue for synthesizing the gRNA sequence. In some embodiments, at least one genome in the reference genome database is a personalized genome of an individual. In some embodiments, at least one genome in the reference genome database is a set of personalized genomes of a population afflicted with a condition. In some embodiments, the reference genome is a *Homo sapiens* reference genome. In some embodiments, the system further comprises outputting a predicted genomic sequence, wherein the predicted genomic sequence represents a predicted output of editing the target genomic information with one or more gRNA's from the second set of gRNA sequences. In some embodiments, the predicted genomic sequence comprises a genomic deletion. In some embodiments, the predicted genomic sequence comprises a genomic insertion. In some embodiments, the calculating calculates an Azimuth score. In some embodiments, the second set of gRNA sequences displays at least two gRNAs above a certain threshold. In some embodiments, the reference genome database comprises at least 50 thousand reference genomes. In some embodiments, the reference genome database comprises at least 120 thousand reference genomes.

Described herein, in certain embodiments, are methods for processing a biopolymer synthesis request from a user over a network, comprising: (a) receiving, by the computer system, the biopolymer synthesis request from a digital computer of the user over the network, which biopolymer synthesis request comprises target genomic information; (b) processing, by the computer system, the target genomic information against one or more reference genomes from a reference genome database to identify a target sequence corresponding to the target genomic information; (c) using one or more computer processors to execute an algorithm to (i) generate a first set of guide ribonucleic acid (gRNA) sequences that are at least partially complementary to the target sequence, and (ii) calculate an off-target complementarity score for each of the gRNA sequences in the first set of gRNA sequences for each of the gRNA sequences; (d) outputting, by the computer system, a second set of gRNA sequences for display on a graphical user interface of the digital computer of the user, where each of the second set of gRNA sequences comprises a calculated off-target complementarity score below a threshold; and (e) receiving from the digital computer of the user a request for a synthesis of a given gRNA sequence from the second set of gRNA sequences.

In some embodiments, the one or more computer processors receiving the request for the synthesis are individually or collectively programmed to direct the synthesis of the given gRNA sequence from the second set of gRNA sequences in a synthesizer. In some embodiments, at least one genome in the reference genome database is a personalized genome of an individual. In some embodiments, at least two genomes in the reference genome database are personalized genomes of a population afflicted with a condition. In some embodiments, the reference genome is a *Homo sapiens* reference genome. In some embodiments, the method further comprises outputting a predicted genomic sequence, wherein the predicted genomic sequence represents a predicted output of editing the target genomic information with one or more gRNA's from the second set of gRNA sequences. In some embodiments, the predicted genomic sequence comprises a genomic deletion. In some embodiments, the predicted genomic sequence comprises a genomic insertion. In some embodiments, the calculating calculates an Azimuth score. In some embodiments, the second set of gRNA sequences displays at least two gRNAs above a certain threshold. In some embodiments, the reference genome database comprises at least 50 thousand reference genomes. In some embodiments, the reference genome database comprises at least 120 thousand reference genomes.

In some embodiments, described herein, are non-transitory computer readable mediums comprising instructions operable, when executed by one or more computer processors, to cause the one or more computer processors to perform any of the methods described herein.

Described herein, in certain embodiments, are non-transitory computer-readable mediums comprising machine executable code that, upon execution by one or more computer processors, implements a method for processing a biopolymer synthesis request from a user over a network, the method comprising: (a) receiving the biopolymer synthesis request from a digital computer of the user over the network, which biopolymer synthesis request comprises target genomic information; (b) processing the target genomic information against one or more reference genomes from a reference genome database to identify a target sequence corresponding to the target genomic information; (c) executing an algorithm to generate a first set of guide ribonucleic acid (gRNA) sequences that are at least partially complementary to the target sequence, and calculate an off-target complementarity score for each of the gRNA sequences in the first set of gRNA sequences; (d) outputting a second set of gRNA sequences for display on a graphical user interface of the digital computer of the user, where each of the second set of gRNA sequences has a calculated off-target complementarity score below a threshold; and (e) receiving from the digital computer of the user a selection of a given gRNA sequence from the second set of gRNA sequences.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 4B shows examples of guides and their off-target and on-target activity analyses. FIG. discloses SEQ ID NO:1-8, respectively, in order of appearance.

FIG. 5 discloses SEQ ID NOS: 9, 9-21, 21-38, 8, 39, 6, 40, 2, 41-44, 44-45, respectively, in order of appearance.

FIG. 7A illustrate a window prior to selecting a genome of interest and a gene of interest. FIG. 7B illustrates a window showing a list of genomes that match a typed input. FIG. 7C illustrates a window showing a list of genes that match a typed input. FIG. 7D illustrates a window after selection of a genome of interest, a gene of interest, and a nuclease.

FIGS. 9A-9D illustrate examples of a window of the GUI for displaying one or more guides that are designed to hybridize the gene of the genome of interest. FIG. 9A discloses SEQ ID NOS: 46-49, respectively in order of appearance. FIG. 9A illustrates a window showing a summary of the designing the one or more gRNAs. FIG. 9B illustrates selection of the top ranked gRNA. FIG. 9B discloses SEQ ID NOS: 46-49, respectively, in order of appearance. FIG. 9C illustrates a window showing information about the selected gRNA. FIG. 9C discloses the Target sequence as SEQ ID NO:4 and gRNA as SEQ ID NOS: 46-49, respectively, in the order of appearance. FIG. 9D illustrates a window showing additional gRNAs designed to hybridize to the gene of the genome of interest. FIG. 9D discloses SEQ ID NOS: 50-59, respectively, in order of appearance.

FIGS. 10A-10E illustrate examples of a window of the GUI for displaying detailed information about a designed guide. FIG. 10A illustrates a summary of the performance of the selected gRNA. FIG. 10A discloses SEQ ID NOS: 3 and 60-64, respectively, in order of appearance. FIG. 10B illustrates a schematic of the Cas-gRNA complex interacting with the target region of interest, with the RNA guide sequence selected. FIG. 10B discloses SEQ ID NOS: 60-62, respectively, in order of appearance. FIG. 10C illustrates a schematic of the Cas-gRNA complex interacting with the target region of interest, with the PAM region selected. FIG. 10C discloses SEQ ID NOS: 60-62, respectively, in order of appearance. FIG. 10D illustrates a schematic of the Cas-gRNA complex interacting with the target region of interest, with the target sequence selected. FIG. 10D discloses SEQ ID NOS: 60-62, respectively, in order of appearance. FIG. 10E illustrates a list of off-target sites of the selected gRNA. FIG. 10E discloses SEQ ID NOS: 63-82, respectively, in order of appearance.

FIG. 11A illustrates a window showing selection of a subset of gRNAs. FIG. 11A discloses SEO ID NOS: 3 and 47-49, respectively, in order of appearance. FIG. 11B illustrates a window showing the selected gRNAs with an additional choice to order modified or unmodified gRNAs. FIG. 11B discloses SEO ID NOS 47 and 3, respectively, in order of appearance.

FIG. 12A illustrates a window prior to selecting a genome of interest and a guide sequence. FIG. 12B illustrates a window after selection of a genome of interest and a guide sequence. (SEQ ID NO:3)

FIGS. 13A-13B illustrate examples of a window of the GUI for displaying detailed information about validation of a guide. FIG. 13A illustrates a summary of the performance of the predetermined gRNA. FIG. 13A discloses SEO ID NOS 3 and 60-62, respectively, in order of appearance. FIG. 13B illustrates a list of off-target sites of the predetermined gRNA. FIG. 13B discloses SEQ ID NOS: 65, 63, 64, 83, 80, 80, 77, 66, 84, 85, 69-71, 73, 80 and 86-90, respectively, in order of appearance.

FIG. 18A illustrates screening of a library for a functional measure. FIG. 18B illustrates screening of a library for editing efficiency.

DETAILED DESCRIPTION

Figure 1:
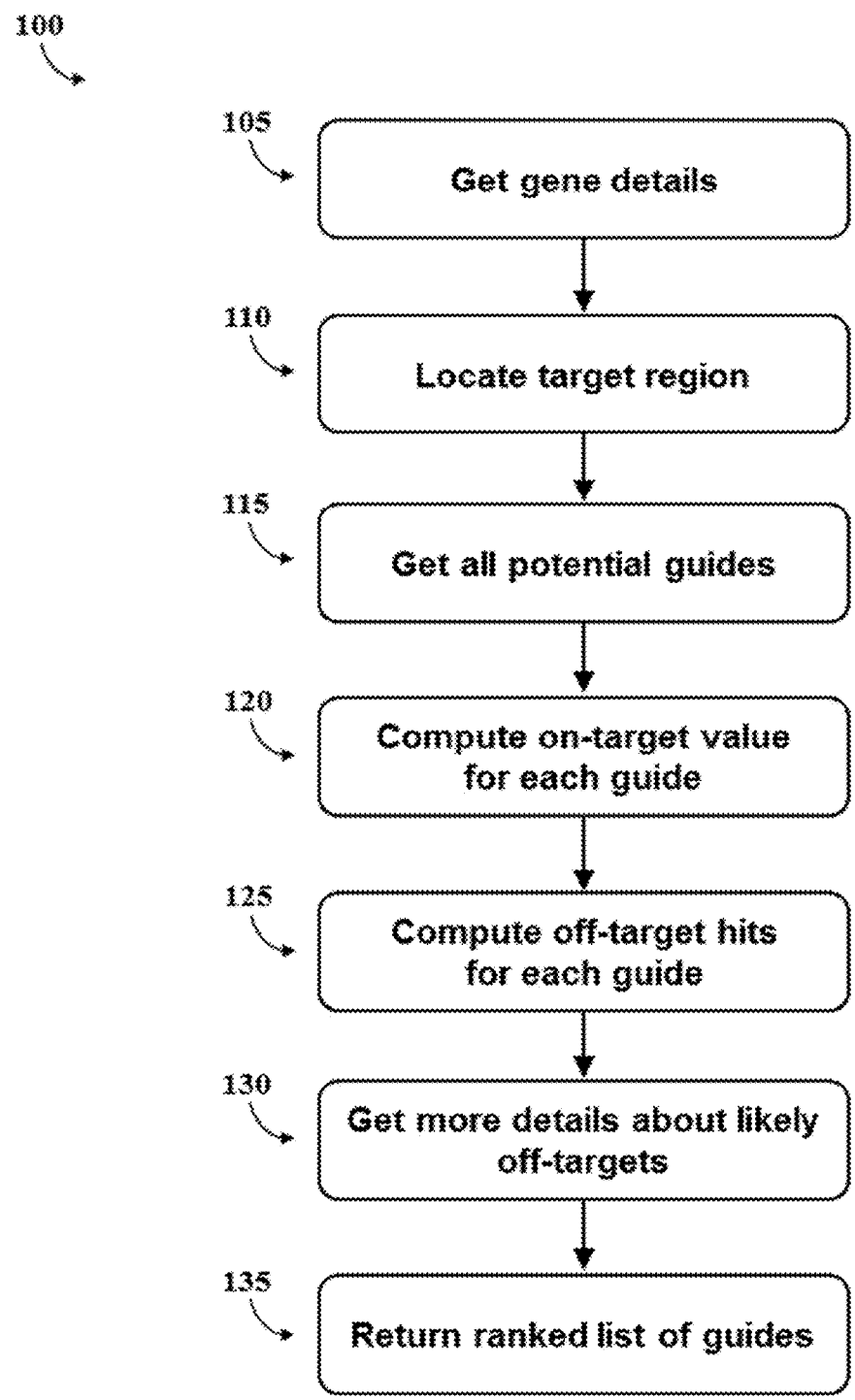
FIG. 1 shows an example of a flowchart of a method of designing one or more guides for hybridizing to a gene of a genome of a species.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

The terminology used herein is for the purpose of describing particular cases only and is not intended to be limiting. The below terms are discussed to illustrate meanings of the terms as used in this specification, in addition to the understanding of these terms by those of skill in the art. As used herein and in the appended claims, the singular forms "a," "an," and, "the" include plural referents unless the context clearly dictates otherwise. It is further noted that the claims can be drafted to exclude any optional element. As such, this statement is intended to serve as antecedent basis for use of such exclusive terminology as "solely," "only," and the like in connection with the recitation of claim elements, or use of a "negative" limitation.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number. Where a range of values is provided, it is understood that each intervening value, to the tenth of the unit of the lower limit unless the context clearly dictates otherwise, between the upper and lower limit of that range and any other stated or intervening value in that stated range, is encompassed within the methods and compositions described herein. The upper and lower limits of these smaller ranges may independently be included in the smaller ranges and are also encompassed within the methods and compositions described herein, subject to any specifically excluded limit in the stated range. Where the stated range includes one or both of the limits, ranges excluding either or both of those included limits are also included in the methods and compositions described herein.

The term "polynucleotide" or "nucleic acid," as used interchangeably herein, can generally refer to a polymeric form of nucleotides of any length, either ribonucleotides and/or deoxyribonucleotides. Thus, these term include, but are not limited to, single-, double-, or multi-stranded DNA or RNA, genomic DNA, complementary DNA (cDNA), guide RNA (gRNA), messenger RNA (mRNA), DNA-RNA hybrids, or a polymer comprising purine and pyrimidine bases or other natural, chemically or biochemically modified, non-natural, or derivatized nucleotide bases. The term "oligonucleotide," as used herein, can generally refer to a polynucleotide of between about 5 and about 100 nucleotides of single- or double-stranded DNA or RNA. However, for the purposes of this disclosure, there may be no upper limit to the length of an oligonucleotide. In some cases, oligonucleotides can be known as "oligomers" or "oligos" and can be isolated from genes, or chemically synthesized by methods known in the art. The terms "polynucleotide" and "nucleic acid" should be understood to include single-stranded (such as sense or antisense) and double-stranded polynucleotides.

The term "modified nucleotide," as used herein, can generally refer to a nucleotide having a modification to the chemical structure of one or more of the base, the sugar, and/or the phosphodiester linkage or backbone portions, including the nucleotide phosphates, relative to a naturally occurring base, sugar, and/or phosphodiester linkage or backbone portions.

The term "hybridization" or "hybridizing," as used herein, can generally refer to a process where completely or partially complementary polynucleotide strands come together under suitable hybridization conditions to form a double-stranded structure or region in which the two constituent strands are joined by hydrogen bonds. In some cases, modified nucleotides can form hydrogen bonds that allow or promote hybridization. In some cases, a guanine (G) of a protein-binding segment of a subject DNA-targeting RNA molecule can be considered complementary to a uracil (U), and vice versa.

The term "cleavage" or "cleaving," as used herein, can generally refer to breaking of the covalent phosphodiester linkage in the ribosyl phosphodiester backbone of a polynucleotide. The term "cleavage" or "cleaving" can encompass cleavage that results in both single-stranded breaks and double-stranded breaks. In some cases, a cleavage may result in the production of either blunt ends or staggered (or sticky) ends.

The term "CRISPR/Cas," as used herein, can refers to a ribonucleoprotein complex comprising a guide RNA (gRNA) and a CRISPR-associated (Cas) endonuclease. The term "CRISPR" refers to the Clustered Regularly Interspaced Short Palindromic Repeats and the related system thereof. While CRISPR was discovered as an adaptive defense system that enables bacteria and archaea to detect and silence foreign nucleic acids (e.g., from viruses or plasmids), it can be adapted for use in a variety of cell types to allow for polynucleotide editing in a sequence-specific manner. In some cases, one or more elements of a CRISPR system can be derived from a type I, type II, or type III CRISPR system. In the CRISPR type II system, the guide RNA can interact with Cas and direct the nuclease activity of the Cas enzyme to a target region. The target region can comprise a "protospacer" and a "protospacer adjacent motif" (PAM), and both domains can be needed for a Cas enzyme mediated activity (e.g., cleavage). The protospacer can be referred to as a target site (or a genomic target site). The gRNA can pair with (or hybridize) the opposite strand of the protospacer (binding site) to direct the Cas enzyme to the target region. The PAM site generally refers to a short sequence recognized by the Cas enzyme and, in some cases, required for the Cas enzyme activity. The sequence and number of nucleotides for the PAM site can differ depending on the type of the Cas enzyme.

The term "Cas," as used herein, can generally refer to a wild type Cas protein, a fragment thereof, or a mutant or variant thereof.

A Cas protein can comprise a protein of or derived from a CRISPR/Cas type I, type II, or type III system, which can be an RNA-guided polynucleotide-binding or nuclease activity. Examples of suitable Cas proteins include CasX, Cas3, Cas4, Cas5, Cas5e (or CasD), Cash, Cas6e, Cas6f, Cas7, Cas8a1, Cas8a2, Cas8b, Cas8c, Cas9 (also known as Csn1 and Csx12), Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cu1966, homologues thereof, and modified versions thereof. In some cases, a Cas protein can comprise a protein of or derived from a CRISPR/Cas type V or type VI system, such as Cpf1 (Cas12a), C2c1 (Cas12b), C2c2, homologues thereof, and modified versions thereof. In some cases, a Cas protein can be a catalytically dead or inactive Cas (dCas).

In some cases, the Cas protein can be a Cas9 protein. In some cases, the PAM sequence recognized by the Cas9 protein can be NGG, where "N" is any nucleotide.

The term "guide RNA" or "gRNA," as used herein, can generally refer to an RNA molecule (or a group of RNA molecules collectively) that can bind to a Cas protein and aid in targeting the Cas protein to a specific location within a target polynucleotide (e.g., a DNA). A guide RNA can comprise a CRISPR RNA (crRNA) segment and a trans-activating crRNA (tracrRNA) segment. The term "crRNA" or "crRNA segment," as used herein, can refer to an RNA molecule or portion thereof that includes a polynucleotide-targeting guide sequence, a stem sequence, and, optionally, a 5'-overhang sequence. The term "tracrRNA" or "tracrRNA segment," can refer to an RNA molecule or portion thereof that includes a protein-binding segment (e.g., the protein-binding segment is capable of interacting with a CRISPR-associated protein, such as a Cas9). The term "guide RNA" can encompasses a single guide RNA (sgRNA), where the crRNA segment and the tracrRNA segment are located in the same RNA molecule. The term "guide RNA" can also encompasses, collectively, a group of two or more RNA molecules, where the crRNA segment and the tracrRNA segment are located in separate RNA molecules.

In some cases, the CRISPR/Cas activity can be useful in any in vitro or in vivo application in which it is desirable to modify a nucleic acid in a site-specific (targeted) way, for example gene knock-out (KO), gene knock-in (KI), gene editing, gene tagging, etc., as used in, for example, gene therapy. The nucleic acid can be DNA or RNA. Examples of gene therapy include treating a disease or as an antiviral, antipathogenic, or anticancer therapeutic; the production of genetically modified organisms in agriculture; the large scale production of proteins by cells for therapeutic, diagnostic, or research purposes; the induction of induced pluripotent stem cells (iPS cells or iPSCs); and the targeting of genes of pathogens for deletion or replacement. In some cases, the Cas can be a catalytically dead or inactive Cas (dCas), and the resulting CRISPR/dCas system can be useful for sequence-specific repression (CRISPR interference) or activation (CRISPR activation) of gene expression.

The term "subject," "individual," or "patient," as used herein, can generally refer to whole organism or a collection thereof that can be in need of and/or subjected to a treatment, such as a farm animal, companion animal, or human, or a collection thereof. In some cases, the term "subject" can be a cell or a cell line thereof.

The term "gene," as used herein, can generally refer to a nucleotide sequence that encodes functional genetic information, such as for example, a nucleotide sequence encoding a polypeptide (e.g., protein), a transfer RNA (tRNA), or a ribosomal RNA (rRNA). The gene can comprise DNA, RNA, or other nucleotides.

Methods for Designing Oligonucleotides

In an aspect, the present disclosure provides a method for designing one or more guide RNAs (gRNAs) for hybridizing to a genomic region of interest. The genomic region of interest can be a gene of a genome of a species. The method can comprise selecting a transcript from a plurality of transcripts of the gene. The method can comprise identifying an initial set of gRNAs that hybridize different target sites in the gene of the selected transcript. The gene can be a gene of interest. The genomic region of interest can be a non-coding region of the genome. The non-coding region can be a regulatory element. The regulatory element can be a cis-regulatory element or a trans-regulatory element. The cis-regulatory element can be a promoter, an enhancer, or a silencer.

Information comprising the genome of the species and/or a reference genome of the species can be obtained from a plurality of databases. In some cases, the plurality of databases can include gene and/or genome databases comprising sequencing data from DNA (DNA-seq) and/or RNA (RNA-seq). Examples of such genome databases include GEN-CODE, NCBI, Ensembl, {APPRIS}, and NIH Human Microbiome Project. Alternatively or in addition to, genomic information of an individual can be retrieved from personalized genome databases, including, but are not limited to, 23andMe, deCODE Genetics, Gene by Gene, Gene Planet, DNA Ancestry, uBiome, and healthcare providers. In some cases, necessary information comprising at least a portion of the genome of the species of interest can be provided by a user (e.g., via a user interface on a user device such as a personal computer).

The genome of the species can comprise some or a complete set of genetic material present in the species (e.g., cell or organism). Examples of the species include, but are not limited to, mammals (e.g., *Homo sapiens, Mus musculus, Cricetulus griseus, Rattus norvegecus, Pan paniscus*), fish (e.g., *Danio rerio, Amphiprion frenatus*), insect (e.g., *Drosophila melanogaster*), plants (e.g., *Arabidopsis thaliana*), roundworms (e.g., *Caenorhabditis elegans*), and microorganisms including bacteria (e.g., *Escherichia coli, Lactobacillus bulgaricus*). In some cases, the bacteria can include strains that are to be consumed by an individual as a supplement (e.g., in yogurt as a medium) and/or as a treatment (e.g., to suppress or ameliorate a condition). In some cases, the bacteria can include strains that are present in the body of an individual (e.g., human microbiome).

The genetic material of the genome can be DNA and/or RNA. The genetic material can include nucleic acid sequences in genes and intergenetic regions. In some cases, the genetic material can be represented as a unit of a chromosome. In some cases, the genetic material can be represented as one or more transcripts that have been transcribed from a gene. The gene and its respective one or more transcripts can comprise one or more coding regions (i.e., exons). In some cases, the gene and its respective one or more transcripts can comprise one or more intragenic non-coding regions (i.e., introns). The one or more intragenic non-coding regions can be located between the coding regions. In some cases, a gene can encode one transcript. In some cases, a gene encode a plurality of transcripts, each transcript comprising different variations of exons and introns from the gene. In an example, the RelA gene encodes for transcription factor p65, and the RELA gene of *Homo sapiens* encodes at least 18 known transcripts of varied length: RELA-202, RELA-207, RELA-226, RELA-205, RELA-201, RELA-208, RELA-220, RELA-207, RELA-215, RELA-204, RELA-222, RELA-213, RELA-225, RELA-211, RELA-219, RELA-221, and RELA-212. Thus, the plurality of transcripts can have different numbers of nucleotide bases (polynucleotide lengths). Alternatively or in addition to, the plurality of transcripts can be translated into polypeptides (e.g., proteins) having different numbers of amino acids (polypeptide lengths). In some cases, each of the plurality of transcripts can have different expression levels (abundance) reported relative to one or more other transcripts.

To identify the initial set of gRNAs for hybridizing the gene, a transcript can be selected from the plurality of transcripts of the gene. In some cases, the selected transcript can have a higher abundance reported than one or more other transcripts in the plurality of transcripts. In some embodiments, the abundance of the plurality of transcripts of the gene is determined from a database. The selected transcript can have the first, second, third, fourth, or fifth highest abundance reported in the plurality of transcripts. In some cases, the selected transcript can have at least one additional nucleotide than one or more other transcripts in the plurality of transcripts. The selected transcript can have the first, second, third, fourth, of fifth largest number of nucleotides in the plurality of transcripts. In some cases, a translated polypeptide (e.g., protein) from the selected transcript can have at least one additional amino acid than one or more polypeptides translated from one or more other transcripts in the plurality of transcripts. The translated polypeptide from the selected transcript can have the first, second, third, fourth, or fifth largest number of amino acids in the plurality of transcripts. In some cases, the abundance of the plurality of transcripts can be a first criterion used to determine the selected transcript from the plurality of transcripts of the gene.

To identify the initial set of gRNAs for hybridizing to the gene, a coding region in the gene present in the selected transcript can be selected. If the gene is DNA, the selected coding region can be closer to a promoter (upstream) of the gene than a terminator (downstream) of the gene. If the gene is RNA, the selected coding region can be closer to a 5' end of the gene than a 3' end of the gene. In some cases, the selected coding region can be an early position exon within the selected transcript. The early position exon can be an exon that is located within the first half of the gene. The early position exon can be the first, second, third, fourth, fifth, of sixth exon of the gene.

In some cases, the selected coding region of the selected transcript can be an exon that has a higher prevalence than one or more other exons present in the one or more of the plurality of transcripts of the gene. In some cases, the selected exon of the selected transcript can be contained (common) in about 50% of the other transcripts in the plurality of transcripts. The selected exon of the selected transcript can be contained in at least about 40 percent (%), 45%, 50%, 55%, 60%, 65%, 70%, 75%, 80%, 85%, 90%, 95%, or more of the other transcripts in the plurality of transcripts. The selected exon of the selected transcript can be contained in at most about 95%, 90%, 85%, 80%, 75%, 70%, 65%, 60%, 55%, 50%, 45%, 40%, or less of the other transcripts in the plurality of transcripts. In some cases, the selected exon of the selected transcript can have at least one additional nucleotide than the other exons in the selected transcript. In some cases, the selected exon can have at least 40, 45, 50, 55, 60, 65, 70, 75, 80, 85, 90, 95, 100, 105, 110, 115, 120, or more nucleotides. In some cases, both the prevalence and the number of nucleotides of the exons can be the criteria to determine the selected exon of the selected transcript.

The initial set of gRNAs can be designed to hybridize to a target region, also referred to herein as a binding site. The target region can be in a gene or a portion of the gene in the genome of the species. In some cases, the portion of the gene can be an exon of the gene. The exon can be an exon found in each transcript of the gene. The exon can be the selected exon of a selected transcript of the plurality of transcripts of the gene from the aforementioned criteria. In some cases, one or more gRNAs in the initial set of gRNAs can be a single guide RNA (sgRNA). In some cases, the sgRNA can be a single polynucleotide chain. The sgRNA can comprise a hybridizing polynucleotide sequence and a second polynucleotide sequence.

The hybridizing polynucleotide sequence can hybridize to the portion of the gene (e.g., the selected exon of the selected transcript of the plurality of transcripts of the gene). The hybridizing polynucleotide sequence of the sgRNA can range between 17 to 23 nucleotides. The hybridizing polynucleotide sequence of the sgRNA can be at least 17, 18, 19, 20, 21, 22, 23, or more nucleotides. The hybridizing polynucleotide sequence of the sgRNA can be at most 23, 22, 21, 20, 19, 18, 17, or less nucleotides. In an example, the hybridizing polynucleotide sequence of the gRNA is 20 nucleotides. The hybridizing polynucleotide sequence can be complementary or partially complementary to the target region. A hybridizing polynucleotide sequence complementary to the target region can comprise a sequence with 100% complementarity to a sequence of the target region. A gRNA partially complementary to the target region can comprise a sequence with at least 1, at least 2, at least 3, at least 4, or at least 5 mismatches relative to a sequence comprising 100% complementary to the target region.

The second polynucleotide sequence of the single polynucleotide chain sgRNA can interact (bind) with the Cas enzyme. The second polynucleotide sequence can be about 80 nucleotides. The second polynucleotide sequence can be 80 nucleotides. The second polynucleotide sequence can be at least 80, or more nucleotides. The second polynucleotide sequence can be at most 80, or less nucleotides.

Overall, the single polynucleotide chain sgRNA can range between 97 to 103 nucleotides. The single polynucleotide chain sgRNA can be at least 97, 98, 99, 100, 101, 102, 103, or more nucleotides. The single polynucleotide chain sgRNA can be at most 103, 102, 101, 100, 99, 98, 97, or less nucleotides. In an example, the single polynucleotide chain sgRNA can be 100 nucleotides.

In some cases, one or more gRNAs in the initial set of gRNAs can be a complex (e.g., via hydrogen bonds) of a CRISPR RNA (crRNA) segment and a trans-activating crRNA (tracrRNA) segment. The crRNA can comprise a hybridizing polynucleotide sequence and a tracrRNA-binding polynucleotide sequence. The hybridizing polynucleotide sequence can hybridize to the portion of the gene (e.g., the selected exon of the selected transcript of the plurality of transcripts of the gene). The hybridizing polynucleotide sequence of the crRNA can range from 17 to 23 nucleotides. The hybridizing polynucleotide sequence of the crRNA can be at least 17, 18, 19, 20, 21, 22, 23, or more nucleotides. The hybridizing polynucleotide sequence of the crRNA can be at most 23, 22, 21, 20, 19, 18, 17, or less nucleotides. In an example, the hybridizing polynucleotide sequence of the crRNA is 20 nucleotides. The tracrRNA-binding polynucleotide sequence of the crRNA can be 22 nucleotides. The tracrRNA-binding polynucleotide sequence of the crRNA can be at least 22, or more nucleotides. The tracrRNA-binding polynucleotide sequence of the crRNA can be at most 22, or less nucleotides. Overall, the crRNA can range from 39 to 45 nucleotides. The crRNA can be at least 39, 40, 41, 42, 43, 44, 45, or more nucleotides. The crRNA can be at most 45, 44, 43, 42, 41, 40, 39, or less nucleotides. The tracrRNA can range from 60 and 80 nucleotides. The tracrRNA can be at least 60, 61, 62, 63, 64, 66, 68, 70, 72, 74, 76, 78, 80, or more nucleotides. The tracrRNA can be at most 80, 79, 78, 77, 76, 74, 72, 70, 68, 66, 64, 62, 60, or less nucleotides. In an example, the tracrRNA can be 72 nucleotides. In another example, the hybridizing polynucleotide sequence of the crRNA is 20 nucleotides, the crRNA is 42 nucleotides, and the respective tracrRNA is 72 nucleotides.

In some cases, the initial set of gRNAs can comprise both one or more sgRNAs and one or more complexes of the crRNA and the tracrRNA. Alternatively or in addition to, one or more gRNAs in the initial set of gRNAs can be a complex of three or more RNA chains. At least one RNA chain of the complex of three or more RNA chains can comprise a hybridizing polynucleotide sequence. At least one RNA chain of the complex of three or more RNA chains can comprise a Cas enzyme binding sequence.

When the gRNA hybridizes to the target region of the genomic region of interest, the hybridized portion of the genomic region of interest can be a target region (or target locus) that comprises a protospacer (target site), a protospacer adjacent motif (PAM) that is recognized by the Cas enzyme, and the opposite strand of the protospacer (binding site). The opposite strand of the protospacer can be the gRNA-hybridizing genomic region (sequence). The gRNA-hybridizing sequence in the gene can range from 17 to 23 nucleotides. The gRNA-hybridizing sequence in the gene can be at least 17, 18, 19, 20, 21, 22, 23, or more nucleotides. The gRNA-hybridizing sequence in the gene can be at most 23, 22, 21, 20, 19, 18, 17, or less nucleotides.

Each of the gRNAs in the initial set of gRNAs can be designed to bind its respective binding site in the genomic region of interest (e.g., a binding site in the selected exon). However, in some cases, each of the gRNAs can also bind other Cas target regions that comprise the PAM site, resulting in an undesirable, off-target binding to an off-target hybridization region. As such, for each of the gRNA of the initial set of gRNAs, an off-target value can be determined. The off-target value can be determined across the genome of the species. In some cases, the off-target value can be determined across a reference genome (e.g., a human reference genome, a microbiome genome, etc.) of the species. The reference genome of the species can be a set of genes assembled from sequencing of DNA (or RNA) from a collection of donors. The reference genome can comprise genetic material from one or more chromosomes. The reference genome can comprise one or more contigs (e.g., unlocalized sequence contigs). Each contig can be a set of overlapping polynucleotide clones that represent a continuous region of DNA. In an example, each contig can be a continuous DNA sequence. The off-target value can be determined (e.g., calculated) by enumerating a number of mismatches for each of the gRNAs in the initial set of gRNAs as compared to a plurality of target sites in the genome. The plurality of target sites can include protospacers of all possible Cas nuclease target regions across the genome.

In some cases, each of the plurality of target sites can be adjacent to a PAM site. In some cases, each of the plurality of target sites can be adjacent to a PAM site for a nuclease selected from the group consisting of: Cas9, C2c1, C2c3, Cpf1, Cas13b, and Cas13c. In an example, the Cas nuclease is Cas9 from *Streptococcus pyogenes* (SpCas9), and the plurality of target sites include all nucleotide sequences adjacent to the PAM site of SpCas9 (NGG, where "N" is any nucleotide). In another example, the Cas nuclease is Cas9 from *Neisseria meningitidis* (NmCas9), and the plurality of target sites include al nucleotide sequences adjacent to the PAM site of NmCas9 (GATT). To be directed to such target sites, one or more of the nucleases (e.g., Cas9, C2c1, C2c3, Cpf1, Cas13b, Cas13c, etc.) can be coupled to at least one gRNA. The at least one gRNA can be designed to hybridize at least one binding site that is an opposite strand of the target site (protospacer).

In an example, a plurality of target sites reported for bacterium can include at least 100, 1,000, 10,000, 20,000, 30,000, 40,000, 50,000, 60,000, 70,000, 80,000, 90,000, 100,000, or more target sites. In another example, a plurality of target sites reported for human can include at least 1000, 10,000, 100,000, 1,000,000, 10,000,000, 20,000,000, 30,000,000, 40,000,000, 50,000,000, 60,000,000, 70,000,000, 80,000,000, 90,000,000, 100,000,000, 200,000,000, 300,000,000, or more target sites. In another example, a plurality of target sites reported for plants can include at least 10,000, 100,000, 1,000,000, 10,000,000, 100,000,000, 200,000,000, 300,000,000, 400,000,000, 500,000,000, 600,000,000, 700,000,000, 800,000,000, 900,000,000, 1,000,000,000, 1,100,000,000, 1,200,000,000, 1,300,000,000, 1,400,000,000, 1,500,000,000, or more target sites.

In some cases, enumerating the number of mismatches for each of the gRNAs as compared to the plurality of target sites can comprise determining the off-target hybridizing region with 0, 1, 2, 3, 4, 5, or more numbers of mismatches. This can be determined across an entire genome for which the gRNA is designed for or a portion of such a genome. The genome can be a reference genome. In some cases, the portion of the genome can be at least 1, 2, 3, 4, 5, 6, 7, 8, 9, 10, or more chromosomes. The number of mismatches can be calculated independently for each of the gRNA (e.g., a gRNA comprising a hybridizing polynucleotide sequence of 20 bases) that are hybridizable to the target. The number of enumerated mismatches can be 0. The number of enumerated mismatches can be 1. The number of enumerated mismatches can be 2. The number of enumerated mismatches can be 3. The number of enumerated mismatches can be 4. In some cases, determining (e.g., calculating) the off-target value comprises enumerating an aggregate sum of the number of mismatches for each of the initial set of gRNAs. In some cases, the enumerating can comprise separately enumerating at least two of 0, 1, 2, 3, 4, or 5 numbers of mismatches from the target sites (potential target sites). In an example, for a designed gRNA, there can be 1 off-target hybridizing region with 0 mismatch (e.g., very nucleotide of the gRNA is collectively paired with a respective nucleotide of the off-target hybridizing region), 3 off-target hybridizing region with 1 mismatch, 5 off-target hybridizing region with 2 mismatches, 7 off-target hybridizing region with 3 mismatches, and 9 off-target hybridizing region with 4 mismatches. Thus, the resulting off-target value of the designed gRNA can be denoted as [1, 3, 5, 7, 9]. In another example, for another designed gRNA, there can be 0 off-target hybridizing region with 0 mismatch (e.g., every nucleotide of the gRNA is collectively paired with a respective nucleotide of the off-target hybridizing region), 0 off-target hybridizing region with 1 mismatch, 15 off-target hybridizing region with 2 mismatches, 50 off-target hybridizing region with 3 mismatches, and 90 off-target hybridizing region with 4 mismatches. Thus, the resulting off-target value of the designed gRNA can be denoted as [0, 0, 15, 50, 90].

The off-target value can be used as a criterion to select a subset of gRNAs from the initial set of gRNAs. In some cases, one of the numbers of mismatches can be used as a threshold to generate the subset of gRNAs from the initial set of gRNAs. In an example, the subset of gRNAs can not have any off-target hybridization region with 0 mismatch. In such case, each of the subset of gRNAs can have an off-target value of [0, #, #, #, #], where "#" denotes any integer of at least 0. In another example, the subset of gRNAs can not have any off-target hybridization region with 0 and 1 mismatch. In such case, each of the subset of gRNAs can have an off-target value of [0, 0, #, #, #], where "#" denotes any integer of at least 0. Not wishing to be bound by theory, increasing the threshold can yield a subset of gRNAs with lower chance of off-target effects in vitro or in vivo.

An on-target efficiency value for each gRNA of the initial set of gRNAs can be determined. The off-target efficiency value of the gRNA can be determined by calculating an azimuth score. The azimuth score can be based on the Doench "Rule Set 2" scoring model. The Rule Set 2 scoring model can use one or more machine learning algorithms to calculate the on-target activity of each gRNA to its respective target region. Examples of parameters used by the one or more machine learning algorithms include: the position of single nucleotides; the position of dinucleotides; the frequency of the single and di-nucleotides; the number of G and C bases in the gRNA; the location of the gRNA within the gene; and the melting temperatures of the first 5, middle 8, and last 5 nucleotides of the gRNA. After the calculation, the resulting on-target activity (azimuth score) can range from 0 and 1.

In some cases, the on-target efficiency value (azimuth score) can be a criterion in selecting a subset of gRNAs from the initial set of gRNAs. The subset of gRNAs from the initial set of gRNAs can have the on-target efficiency value of at least about 0.2. The subset of gRNAs from the initial set of gRNAs can have the on-target efficiency value of at least about 0.2, 0.3, 0.4, 0.5, 0.6, 0.7, 0.8, 0.9, or more. In an example, the subset of gRNAs from the initial set of gRNAs can have the on-target efficiency value of greater than 0.4.

In some cases, both the on-target efficiency and the off-target value of a gRNA can be the criteria in selecting a subset of gRNAs from the initial set of gRNAs. In an example, identifying the subset of gRNAs can be based on the threshold value of the on-target efficiency (e.g., an azimuth score greater than 0.4) and the threshold value of the off-target value (e.g., no off-target hybridization sites with 0 or 1 mismatches). Based on the two criteria, each gRNA in the initial set of gRNAs can be ranked. The subset of gRNAs from the initial set of gRNAs can comprise from 1 to 10 of the top ranked gRNAs. The subset of gRNAs from the initial set of gRNAs can comprise at least 1, 2, 3, 4, 5, 6, 7, 8, 9, 10, or more of the top ranked gRNAs. The subset of gRNAs from the initial set of gRNAs can comprise at most 10, 9, 8, 7, 6, 5, 4, 3, 2, or less of the top ranked gRNAs.

The initial set of gRNAs, each designed to hybridize a portion of the gene of the genome of the species, can be used to knock-out (KO) the gene in a cell. The KO can be a targeted KO. Alternatively or in addition to, the initial set of gRNAs, each designed to hybridize the portion of the gene of the genome of the species, can be used to knock-in (KI) a mutation in the gene in a cell. The KI can be a targeted insertion. The targeted insertion can be an insertion of a donor polynucleotide. In some cases, at least one CRISPR/Cas complex can be directed to a target region by at least one specific gRNA and cleave the target region. In some examples, the cleavage can lead to insertion and/or deletion ("indel") mutations or a frameshift by a non-homologous end joining (NHEJ) process, leading to a target gene-specific KO. In some cases, CRISPR/Cas complex can be directed to the target genomic region by the specific gRNA along with a co-administered, donor polynucleotide (single- or double-stranded). Following the cleavage of the target region, a homology-directed repair (HDR) process can use one or more of the donor polynucleotide as one or more templates for (a) repair of the cleaved target nucleotide sequence and (b) a transfer of genetic information from the donor polynucleotide to the target DNA. Depending on the nature of the genetic information, the HDR process can yield a target gene-specific KO or KI. Examples of applications of the HDR-mediated gene KI include the addition (insert or replace) of nucleic acid material encoding for a protein, mRNA, small interfering RNA (siRNA), tag (e.g., 6×His (SEQ ID NO:91), a reporter protein (e.g., a green fluorescent protein), and a regulatory sequence to a gene (e.g., a promotor, polyadenylation signal).

For the HDR process, the donor polynucleotide can contain the desired gene edit (sequence) to be copied, as well as additional nucleotide sequences on both ends (homology arms) that are homologous immediately upstream and downstream of the cleaved target site. In some cases, the efficiency of the HDR process can depend on the size of the gene edit and/or the size of the homology arms. Alternatively or in addition to, the efficiency of the HDR process can depend on the availability of Cas target regions that comprise the PAM site. Thus, the methods comprising determining (a) the initial set of RNA sequences from the plurality of gene and/or genome databases, (b) the on-target efficiency, and/or (c) the off-target value can be utilized to design a set of donor polynucleotides for HDR.

The CRISPR/cas system according to the present disclosure can be used in a variety of cells. Cells can be any prokaryotic or eukaryotic living cells, cell lines derived from these organisms for in vitro cultures, primary cells from animal or plant origin. Eukaryotic cells can refer to a fungal, plant, algal or animal cell or a cell line derived from the organisms listed below and established for in vitro culture. The fungus can be of the genus *Aspergillus, Penicillium, Acremonium, Trichoderma, Chrysoporium, Mortierella, Kluyveromyces* or *Pichia*; More preferably, the fungus is of the species *Aspergillus nagger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyceslactis, Pichia pastoris* or *Pichia ciferrii*. The plant can be of the genus *Arabidospis, Nicotiana, Solanum, lactuca, Brassica, Oryza, Asparagus, Pisum, Medicago, Zea, Hordeum, Secale, Triticum, Capsicum, Cucumis, Cucurbita, Citrullis, Citrus, Sorghum*. The plant can be of the species *Arabidospis thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisumsativum, Medicago sativa, Zea mays, Hordeum vulgare, Secale cereal, Triticuma estivum, Triticum durum, Capsicum sativus, Cucurbitapepo, Citrullus lanatus, Cucumis melo, Citrus aurantifolia, Citrus maxima, Citrus medica*, and *Citrus reticulata*. The animal cell can be of the genus *Homo, Rattus, Mus, Cricetulus, Pan, Sus, Bos, Danio, Canis, Felis, Equus, Salmo, Oncorhynchus, Gallus, Meleagris, Drosophila, Caenorhabditis*. The animal cell can be of the species *Homo sapiens, Rattus norvegicus, Mus musculus, Cricetulus griseus, Pan paniscus, Sus scrofa, Bos taurus, Canis lupus, Cricetulus griseus, Danio rerio, Felis catus, Equus caballus, Rattus norvegecus, Salmo salar, Oncorhynchus mykiss, Gallus gallus, Meleagris gallopavo, Drosophila melanogaster*, and *Caenorhabditis elegans*.

Examples cell lines can be selected from the group consisting of CHO cells (e.g., CHO-K1); HEK293 cells;

Caco2 cells; U2-OS cells; NIH 3T3 cells; NSO cells; SP2 cells; DG44 cells; K-562 cells, U-937 cells; MC5 cells; IMR90 cells; Jurkat cells; HepG2 cells; HeLa cells; HT-1080 cells; HCT-116 cells; Hu-h7 cells; Huvec cells; and Molt 4 cells. Examples of other cells applicable to the scope of the present disclosure can include stem cells, embryonic stem cells (ESCs) and induced pluripotent stem cells (iP-SCs). All these cell lines and/or cells can be modified by the method of the present invention to provide cell line models to produce, express, quantify, detect, and/or study a gene or a protein of interest; and/or to screen biologically active molecules of interest in research and production and various fields such as chemical, biofuels, therapeutics and agronomy as non-limiting examples.

In some cases, at least one nucleotide from at least one guide RNA in the initial set of guide RNAs can be modified. Examples of the modification of the at least one nucleotide can include: (a) end modifications, including 5' end modifications or 3' end modifications; (b) nucleobase (or "base") modifications, including replacement or removal of bases; (c) sugar modifications, including modifications at the 2', 3', and/or 4' positions; and (d) backbone modifications, including modification or replacement of the phosphodiester linkages. Not wishing to be bound by theory, the modification of the at least one nucleotide can provide, for example: (a) improved target specificity; (b) reduced effective concentration of the CRISPR/Cas complex; (c) improved stability of the gRNA (e.g., resistance to ribonucleases (RNases) and/or deoxyribonucleases (DNases)); and (d) decreased immunogenicity. In an example, the at least one nucleotide from the at least one guide RNA in the initial set of guide RNAs can be a 2'-O-methyl nucleotide. Such modification can increase the stability of the gRNA with respect to attack by RNases and/or DNases.

In some cases, a nucleotide sugar modification incorporated into the guide RNA is selected from the group consisting of 2'-O—C1-4alkyl such as 2'-O-methyl (2'-OMe), 2'-deoxy (2'-H), 2'-O—C1-3alkyl-O—C1-3alkyl such as 2'-methoxyethyl ("2'-MOE"), 2'-fluoro ("2'-F"), 2'-amino ("2'-NH2"), 2'-arabinosyl ("2'-arabino") nucleotide, 2'-F-arabinosyl ("2'-F-arabino") nucleotide, 2'-locked nucleic acid ("LNA") nucleotide, 2'-unlocked nucleic acid ("ULNA") nucleotide, a sugar in L form ("L-sugar"), and 4'-thioribosyl nucleotide. In some cases, an internucleotide linkage modification incorporated into the guide RNA is selected from the group consisting of: phosphorothioate "P(S)" (P(S)), phosphonocarboxylate (P(CH$_2$)$_n$COOR) such as phosphonoacetate "PACE" (P(CH$_2$COO$^-$)), thiophosphonocarboxylate ((S)P(CH$_2$)$_n$COOR) such as thiophosphonoacetate "thioPACE" ((S)P(CH$_2$)$_n$COO$^-$)), alkylphosphonate (P(C1-3alkyl) such as methylphosphonate —P(CH$_3$), boranophosphonate (P(BH$_3$)), and phosphorodithioate (P(S)$_2$).

In some cases, a nucleobase ("base") modification incorporated into the guide RNA is selected from the group consisting of: 2-thiouracil ("2-thioU"), 2-thiocytosine ("2-thioC"), 4-thiouracil ("4-thioU"), 6-thioguanine ("6-thioG"), 2-aminoadenine ("2-aminoA"), 2-aminopurine, pseudouracil, hypoxanthine, 7-deazaguanine, 7-deaza-8-azaguanine, 7-deazaadenine, 7-deaza-8-azaadenine, 5-methylcytosine ("5-methylC"), 5-methyluracil ("5-methylU"), 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil ("5-allylU"), 5-allylcytosine ("5-allylC"), 5-aminoallyluracil ("5-aminoallylU"), 5-aminoallyl-cytosine ("5-aminoallylC"), an abasic nucleotide, Z base, P base, Unstructured Nucleic Acid ("UNA"), isoguanine ("isoG"), isocytosine ("isoC"), and 5-methyl-2-pyrimidine.

In some cases, one or more isotopic modifications are introduced on the nucleotide sugar, the nucleobase, the phosphodiester linkage and/or the nucleotide phosphates. Such modifications include nucleotides comprising one or more $^{15}$N, $^{13}$C, $^{14}$C, Deuterium, $^3$H, $^{32}$P, $^{125}$I, $^{131}$I atoms or other atoms or elements used as tracers.

In some cases, an "end" modification incorporated into the guide RNA is selected from the group consisting of: PEG (polyethyleneglycol), hydrocarbon linkers (including: heteroatom (O,S,N)-substituted hydrocarbon spacers; halo-substituted hydrocarbon spacers; keto-, carboxyl-, amido-, thionyl-, carbamoyl-, thionocarbamaoyl-containing hydrocarbon spacers), spermine linkers, dyes including fluorescent dyes (for example fluoresceins, rhodamines, cyanines) attached to linkers such as for example 6-fluorescein-hexyl, quenchers (for example dabcyl, BHQ) and other labels (for example biotin, digoxigenin, acridine, streptavidin, avidin, peptides and/or proteins). In some cases, an "end" modification comprises a conjugation (or ligation) of the guide RNA to another molecule comprising an oligonucleotide (comprising deoxynucleotides and/or ribonucleotides), a peptide, a protein, a sugar, an oligosaccharide, a steroid, a lipid, a folic acid, a vitamin and/or other molecule. In some cases, an "end" modification incorporated into the guide RNA is located internally in the guide RNA sequence via a linker such as, for example, 2-(4-butylamidofluorescein)propane-1,3-diol bis(phosphodiester) linker, which is incorporated as a phosphodiester linkage and can be incorporated anywhere between two nucleotides in the guide RNA.

In some cases, a computer can be utilized to perform the method for designing one or more guide RNAs (gRNAs) for hybridizing to a to genomic region of interest.

FIG. 1 shows an example of a flowchart 100 of a method of designing one or more guides (e.g., gRNAs) for hybridizing to a gene of a genome of a species. The method comprises: (a) getting details on the gene of interest from one or more databases 105; (b) locate a target region (e.g., an exon of a selected transcript of a plurality of transcripts of the gene) 110; (c) get potential guides (e.g., one or more gRNAs with a hybridizing polynucleotide sequence) 115; (d) compute on-target value for each guide (e.g., calculate an azimuth score for each guide) 120; (e) compute off-target hits for each guide 125; (f) get more details about likely off-targets (e.g., enumerating the number of mismatches for each of the gRNAs as compared to a plurality of possible Cas target regions across the genome) 130; and (g) return a ranked list of the guides 135. In (g), the guides can be ranked by the on-target values and/or the off-target values. In some cases, the order of the steps (d) and (e-f) can be interchangeable.

Figure 2:
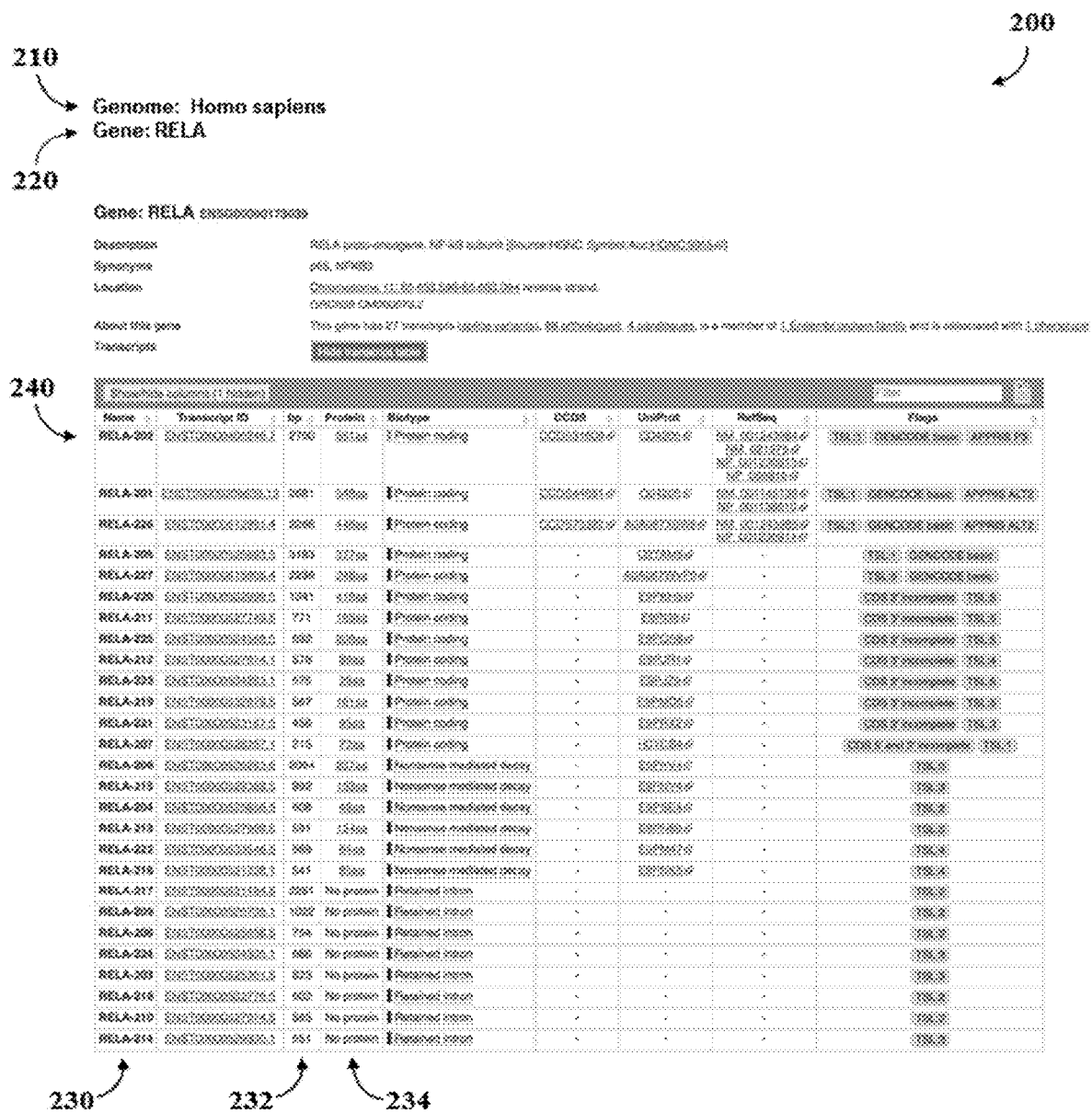
FIG. 2 shows an example of a table of a plurality of transcripts of a gene of a genome of a species.

FIG. 2 shows an example of a table 200 of a plurality of transcripts of a gene of a genome of a species. The information can be obtained from one or more databases. In this example, the gene of interest is RELA 220 of *Homo sapiens* 210. A plurality of transcripts 230 are known for RELA. The plurality of RELA transcripts can have different numbers of nucleotide bases 232. Alternatively or in addition to, the plurality of transcripts can be translated into polypeptides (e.g., proteins) that have different numbers of amino acids 234. Furthermore, a transcript can have a higher abundance reported than one or more other transcripts in the plurality of transcripts (not shown). Based on one or more of the aforementioned factors, a primary transcript 240 is selected.

Figure 3:
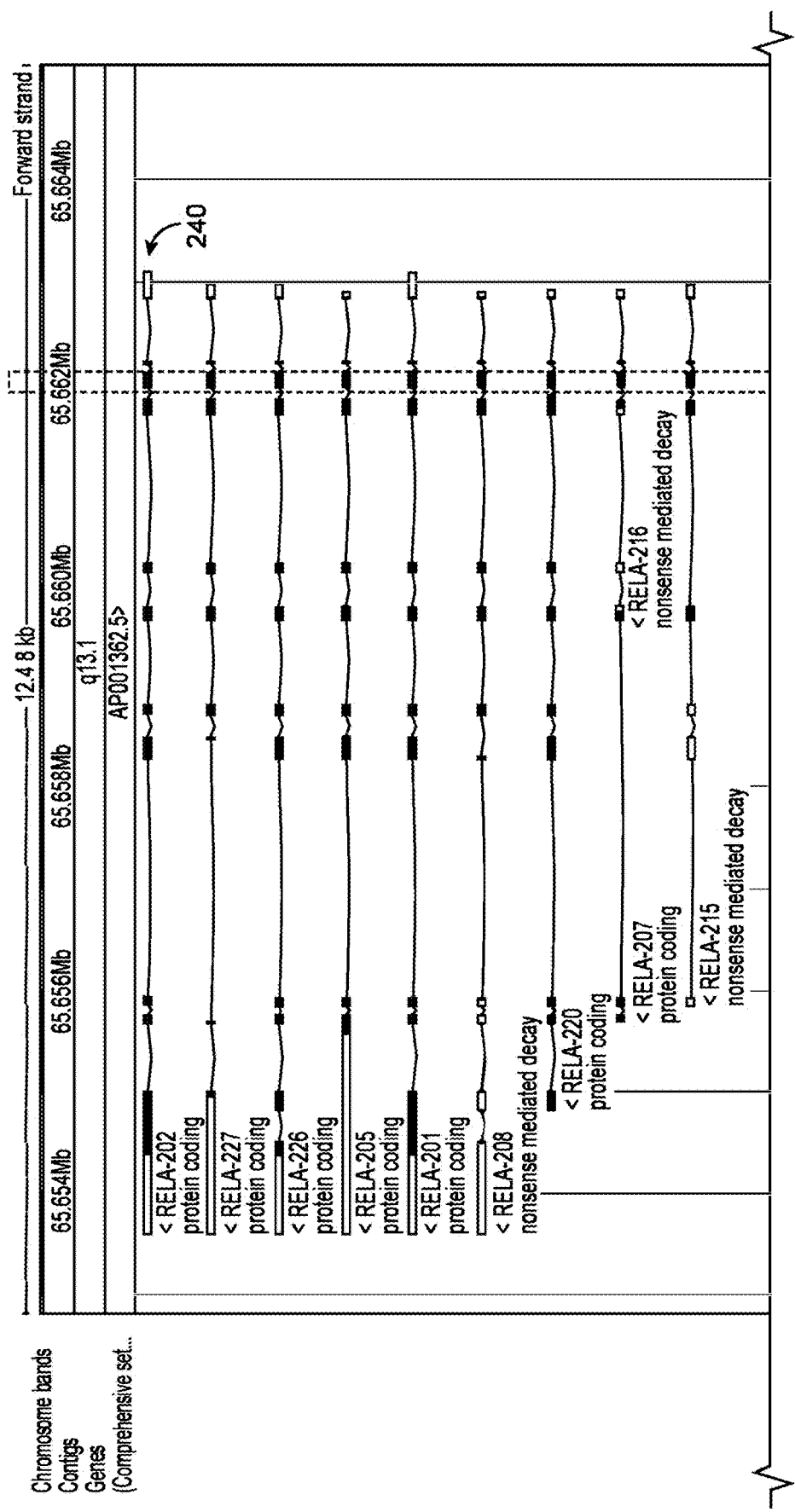
FIG. 3 shows an example of an early coding region of a transcript to be targeted by one or more gRNAs.
Figure 3:
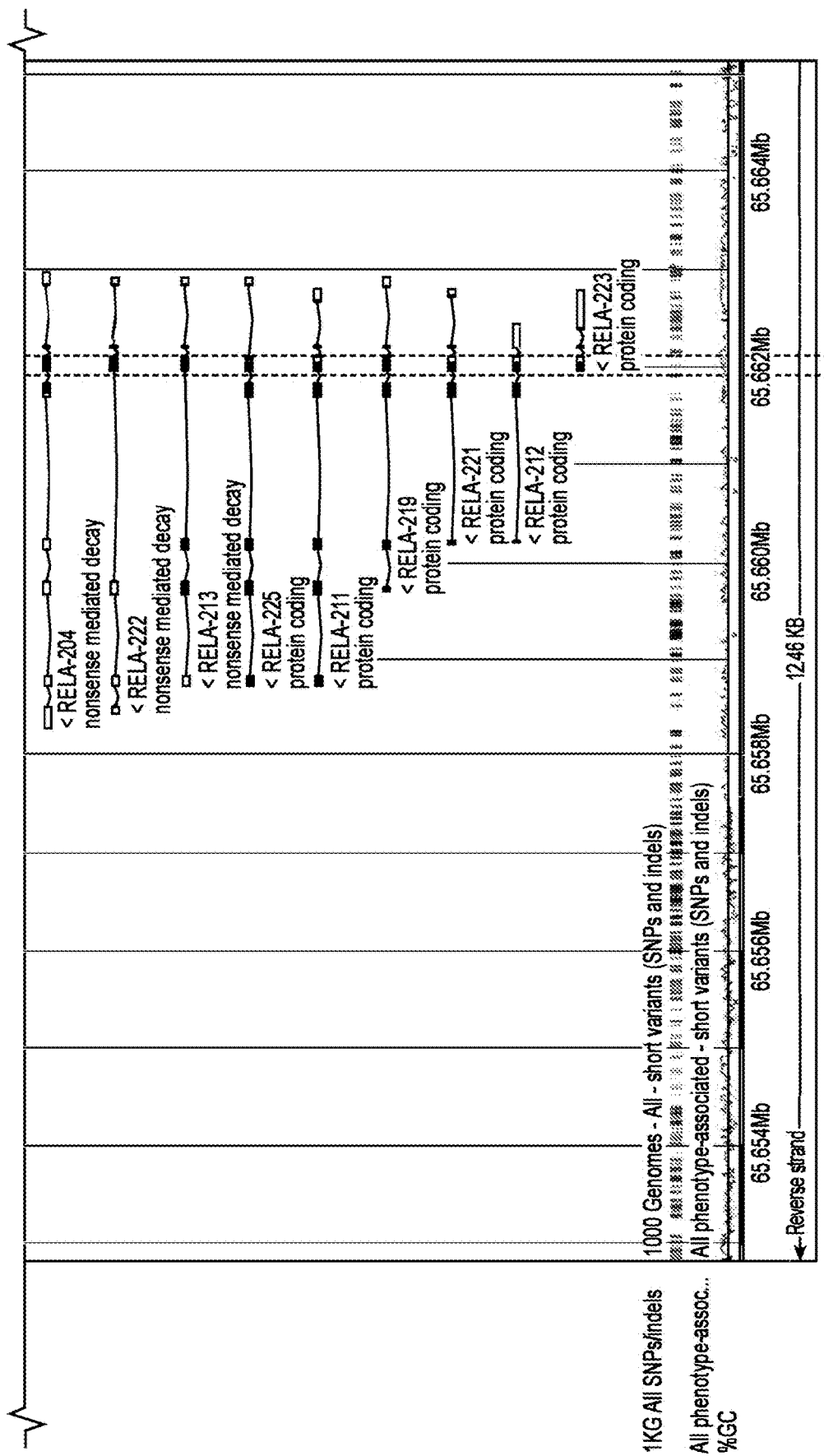

FIG. 3 shows an example of an early coding region of a transcript to be targeted by one or more gRNAs. In a plurality of transcripts of the human gene RELA, the primary transcript 240 is analyzed to select an early coding region comprising an exon 310. The exon 310 is also found in more than 50 percent (%) of the other transcripts of the plurality of transcripts. Subsequently, all possible Cas target regions across the exon 310 can be identified to design the one or more gRNAs for targeting and hybridizing.

Figure 4A:
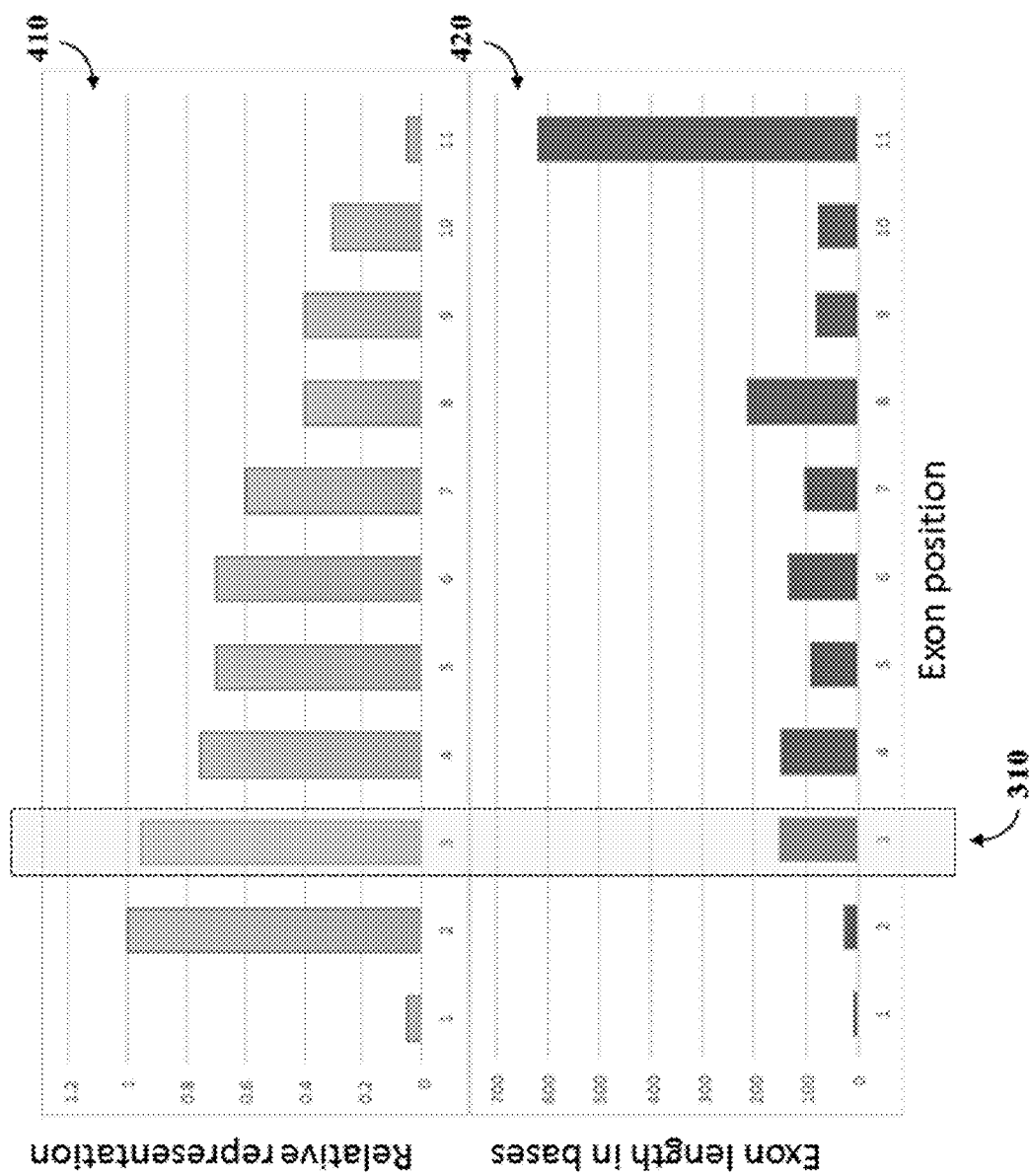
FIG. 4A shows examples of plots of relative representation and exon length of a plurality of exons from a transcript.

FIG. 4A shows examples of plots of relative representation 410 and exon length 420 of a plurality of exons from a transcript. The plurality of exons (positions 1 through 11) are from the primary transcript 240. The selected exon 310 has a relative representation value of over 0.9, suggesting that it is present in more than 90% of the other transcripts of the same gene. The selected exon 310 is also over 100 nucleotides in length.

FIG. 4B shows examples of gRNAs 450, 452, 454, and 460 and their off-target and on-target activity analyses. The analysis for each gRNA is summarized as a recommendation bracket [A, B, C, D], where A denotes whether the gRNA is designed to target an early coding region of a gene; B denotes whether the intended target site of the gene is common in a plurality of transcripts of the gene (i.e., found in over 50% of the other transcripts in the plurality of transcripts of the gene); C denotes whether the on-target activity of the gRNA is above a threshold value (i.e., an azimuth score greater than 0.4); and D denotes whether the off-target activity of the gRNA is above a threshold value (i.e., not having any off-target hybridizing region with 0 and 1 mismatch). All four factors A through D need to be "True" (as opposed to "False") for the gRNA to be selected for use. In FIG. 4B, only the gRNA 460 is deemed True for all four factors.

Computer System

Another aspect of the present disclosure provides a computer system for performing the aforementioned method for designing one or more guide RNAs (gRNAs) for hybridizing to a genomic region of interest. Another aspect of the present disclosure provides a computer system for performing the aforementioned method for designing one or more guide RNAs (gRNAs) for hybridizing to each of a plurality of genomic regions of interest. The genomic region of interest can be a gene of a genome of a species. The computer system can comprise a computer readable medium for selecting a transcript from a plurality of transcripts of the gene. The computer system can comprise a computer readable medium for identifying an initial set of gRNAs that hybridize different target sites in the gene of the selected transcript.

The computer readable medium of the computer can receive (e.g., from a user via a user interface on a user device) input of the gene and the species of interest. The computer readable medium can be in communication with a plurality of databases to obtain information comprising the genome of the species and/or a reference genome of the species. In some cases, the computer readable medium can be in communication with the plurality of databases including gene and/or genome databases comprising sequencing data from DNA (DNA-seq) and/or RNA (RNA-seq). Based on such information, the computer readable medium can select the transcript from the plurality of transcripts of the gene. The computer readable medium can identify the initial set of gRNAs that hybridize different target sites in the gene of the selected transcript. Alternatively or in addition to, the computer readable medium can be configured to perform one or more tasks related to the aforementioned method for designing the one or more gRNAs for hybridizing the gene of the genome of the species (e.g., calculating off-target values for the one or more gRNAs). Furthermore, the computer readable medium can also include instructions for automatically activating a biopolymer (e.g., RNA) synthesizer as selected by a user of the design tool.

Figure 5:
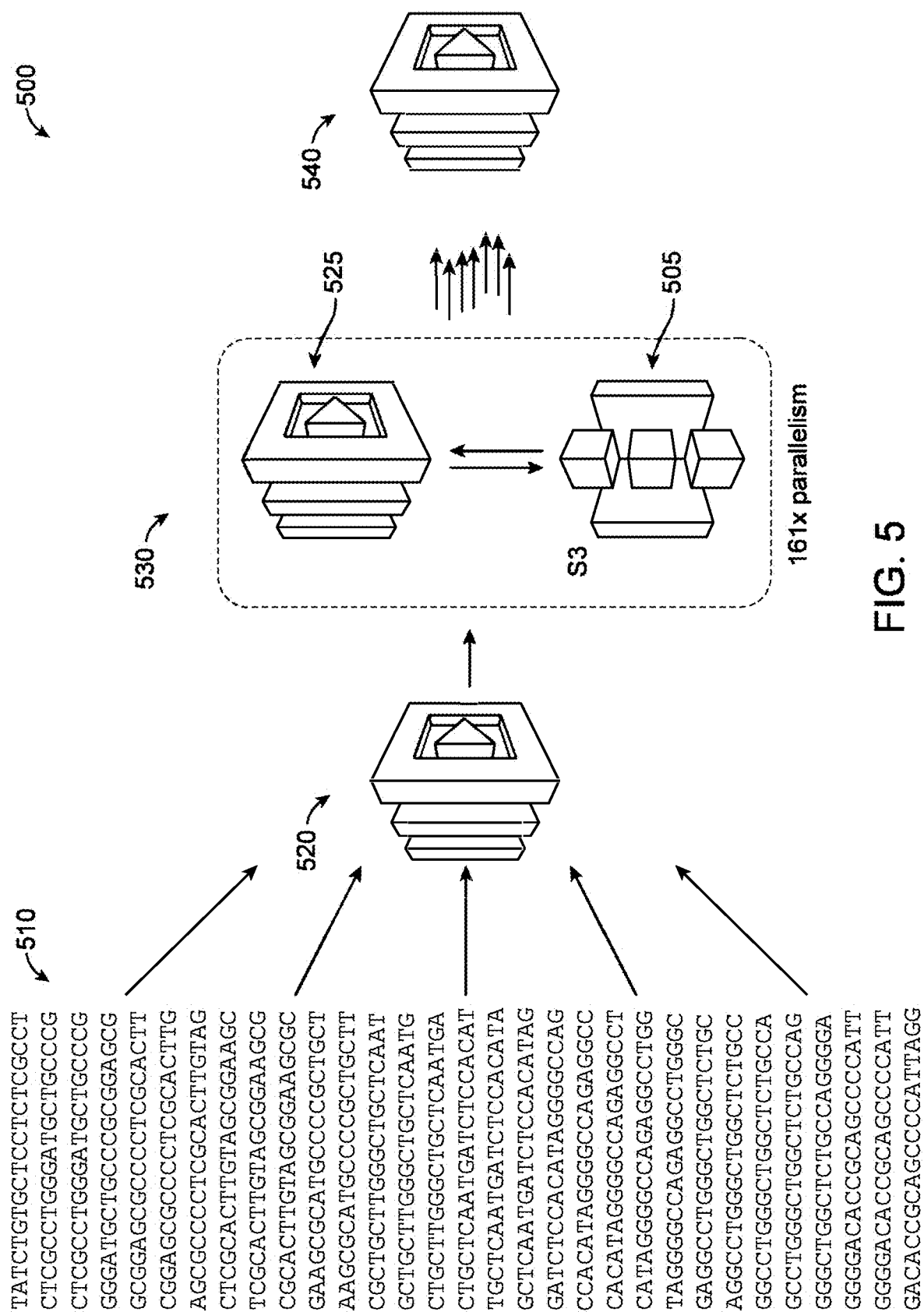
FIG. 5 shows a data processing architecture for calculating off-target values of a plurality of guides across a genome.

FIG. 5 shows a data processing architecture 500 for calculating off-target values of a plurality of gRNAs across a genome. An initial set of gRNAs (or, alternatively, a set of the respective target site sequences of each gRNA) 510 is entered into a "master" query 520 of a computing platform (e.g., a serverless computing platform). At the same time, a database of all possible Cas target regions across the genome (e.g., each domain comprising a protospacer sequence and a PAM site) is partitioned into smaller subsets (or "shards") 505. To obtain the off-target values, the master query 520 invokes additional "slave" queries 525, one per each shard, and compares 530 each slave query to each shard to determine mismatches and the overall off-target value of each gRNA. After the off-target search, the results from slave query-shard comparisons are collected into a results aggregator 540. In an example, a database of about 320 million Cas target regions can be partitioned into 161 shards, each comprising about 2 million Cas target regions. As such, the master query would invoke 161 slave queries for off-target search. By using the data processing architecture 500 and simultaneously running comparisons, the output time of the analyses can be reduced.

Multiple gRNA Systems

In some embodiments, the present disclosure provides a method for identifying a set of guide RNAs (gRNAs) that target a genomic region of interest. The set of gRNAs can comprise at least 2, at least 3, at least 4, at least 5, at least 10, at least 20, at least 50, at least 100, or at least 200 gRNAs. The set of gRNAs can consist of 2 gRNAs. The set of gRNAs can consist of 3 gRNAs. The set of gRNAs can consist of 4 gRNAs. The method can comprise designing, in a computer, a set of gRNAs. Each gRNA in the set can be hybridizable to a different target site within the genomic region of interest (e.g., a gene, gene cluster, exon).

The distance between a target site of each gRNA in a set of gRNAs targeting the same genomic region of interest can also be referred to herein as the inter-guide spacing. The inter-guide spacing can be the distance, in base pairs, from the 3' end of a first target site in a genomic region of interest of a first gRNA to the 5' end of a second target site in the genomic region of interest of a second gRNA in a set of gRNAs. The inter-guide spacing can be non-inclusive of the base pairs comprising the target site in the genomic region of interest of the first gRNA and the target site in the genomic region of interest of the second gRNA. The inter-guide spacing can be determined based on a reference genome. The inter-guide spacing can be determined between sequential target sites in the genomic region of interest. In an example, a minimum distance between a target site in a genomic region of interest of a gRNA in the set of gRNAs is at least 30 bases apart from the target site in the genomic region of interest of at least one other gRNA from the set of gRNAs. In another example, a minimum distance between a target site in a genomic region of interest of each gRNA in the set of gRNAs is at least 30 bases apart from the target site in the genomic region of interest of every other gRNA from the set of gRNAs. In another example, a maximum distance between a target site in a genomic region of interest of a gRNA in the set of gRNAs is at most 150 bases apart from the target site in the genomic region of interest of at least one other gRNA from the set of gRNAs. In some embodiments, at least 50%, at least 60%, at least 70%, at least 80%, at least 90%, or at least 95% of the sets of gRNAs in a plurality of sets of gRNAs comprise at least 3 gRNAs.

Editing efficiency can indicate the proportion of cells comprising an edited genotype at the genomic region of interest. The cells can be a population of cells contacted with at least one set of gRNAs, a nuclease, and optionally a donor polynucleotide. The edited genotype can be any non-wild-type genotype. The edited genotype can comprise an insertion or deletion relative to a wild-type genotype. The edited genotype can be a result of repair of a double stranded break caused by a CRISPR/Cas complex at the target site. The edited genotype can result in a knock-out of the genomic region of interest. In some embodiments, a set of gRNAs with a minimum distance between target regions in the genomic region of interest of each gRNA in the set of gRNAs of 30 or more bases produces an editing efficiency of greater than 50%, 60%, 70%, or 80%. In some embodiments, a plurality of sets of gRNAs comprise a mean editing efficiency of at least 50%, 60%, 70%, or 80%. In some embodiments, at least 50%, 60%, 70%, 80%, 90%, or 95% of the sets of gRNA in a plurality of sets of gRNAs comprise a mean editing efficiency of greater than 50%. In some embodiments, at least 50%, 60%, 70%, 80%, 90%, or 95% of the sets of gRNA in a plurality of sets of gRNAs comprise a mean editing efficiency of greater than 70%. The editing efficiency can be determined by sequencing. The sequencing can be Sanger sequencing. The sequencing can be high throughput sequencing.

Each gRNA in the set can be hybridizable to a target site that is at least 10 bases apart from the target site in the genomic region of interest of at least one other gRNA from the set of gRNAs. Each gRNA in the set can be hybridizable to a target site in the genomic region of interest that is at least 30 bases apart from the target site in the genomic region of interest of at least one other gRNA from the set of gRNAs. Each gRNA in the set can be hybridizable to a target site in the genomic region of interest that is at most 170 bases apart from the target site in the genomic region of interest of at least one other guide RNA from the set of guide RNAs. Each gRNA in the set can be hybridizable to a target site in the genomic region of interest that is at most 1000 bases apart from the target site in the genomic region of interest of at least one other guide RNA from the set of guide RNAs. Preferably the target site in the genomic region of interest of each gRNA from the set of gRNAs is separated from the target site in the genomic region of interest of any other gRNA in the set by about 10-170, 30-170, 10-150, 30-150, 10-100, 30-100, or 30-1000 bases. This arrangement can result in improved KO properties and synergistic effects between the various CRISPR enzymes. In some embodiments, knockout of a genomic region of interest is achieved using an amount of each gRNA in a set of gRNAs less than the amount of each gRNA individually required to achieve knockout of the genomic region of interest. The amount of each gRNA in a set of gRNAs required to achieve knockout of the genomic region of interest can be ⅓ of the amount of each gRNA individually required to achieve knockout of the genomic region of interest. The amount of each gRNA in a set of gRNAs required to achieve knockout of the genomic region of interest can be ½ of the amount of each gRNA individually required to achieve knockout of the genomic region of interest.

Further described herein, in certain embodiments, are methods for identifying a plurality of sets of guide RNAs (gRNAs), each set of gRNAs in the plurality of sets of gRNAs targeting a different genomic region of interest in a plurality of genomic region of interests. The plurality of genomic regions of interest can comprise 2, 3, 4, 5, 6, 7, 8, 9, 10, or more than 10 genomic regions of interest. The method can comprise designing, in a computer, a different set of gRNAs for each of the plurality of genomic regions of interest. Each gRNA in the set of gRNAs can be hybridizable to a different target site within the genomic region of interest (e.g., a gene, gene cluster, exon). Each gRNA in the set of gRNAs can be hybridizable to a target site in the genomic region of interest that is at least 10 bases apart from the target site in the genomic region of interest of at least one other gRNA from the set of gRNAs. Each gRNA in the set can be hybridizable to a target site in the genomic region of interest that is at least 30 bases apart from the target site in the genomic region of interest of at least one other gRNA from the set of gRNAs. Each gRNA in the set of gRNAs can be hybridizable to a target site in the genomic region of interest that is at most 170 bases apart from the target site in the genomic region of interest of at least one other guide RNA from the set of guide RNAs. Each gRNA in the set of gRNAs can be hybridizable to a target site in the genomic region of interest that is at most 1000 bases apart from the target site in the genomic region of interest of at least one other gRNA from the set of gRNAs. Preferably the target site in the genomic region of interest of each gRNA from the set of gRNAs is separated from the target site in the genomic region of interest of any other gRNA in the set by about 10-170, 30-170, 10-150, 30-150, 10-100, 30-100, or 30-1000 bases. This arrangement can result in improved KO properties and synergistic effects between the various CRISPR enzymes.

The computer can be the aforementioned computer system for performing the method for designing one or more gRNAs for hybridizing to a genomic region of interest. The genomic region of interest can be a gene of a genome of a species. The genomic region of interest can be a non-coding region of the genome. The non-coding region can be a regulatory element. The regulatory element can be a cis-regulatory element or a trans-regulatory element. The cis-regulatory element can be a promoter, an enhancer, or a silencer. The identified set of gRNAs can be a subset of the one or more gRNAs for hybridizing the gene of the genome of the species. In some cases, one or more gRNAs of the set of gRNAs can be a single guide RNA (sgRNA). In some cases, one or more gRNAs of the set of gRNAs can be a complex (e.g., via hydrogen bonds) of a CRISPR RNA (crRNA) segment and a trans-activating crRNA (tracrRNA) segment.

Each gRNA of the set of gRNAs can comprise a polynucleotide sequence (a hybridizing polynucleotide sequence) that hybridizes to the different target site within the genomic region of interest. The hybridizing polynucleotide sequence of the gRNA can range from 17 to 23 nucleotides. The hybridizing polynucleotide sequence of the gRNA can be at least 17, 18, 19, 20, 21, 22, 23, or more nucleotides. The hybridizing polynucleotide sequence of the gRNA can be at most 23, 22, 21, 20, 19, 18, 17, or less nucleotides. In an example, the hybridizing polynucleotide sequence of the gRNA is 20 nucleotides.

The gene of the genome of the species can have one or more transcripts. In an example, the gene can be transcribed into one or more transcripts. The one or more transcripts can comprise one or more coding regions (i.e., exons) and/or one or more intragenic non-coding regions (i.e., introns). In some cases, the genomic region of interest can comprise a coding region of the gene. In some cases, the genomic region of interest can comprise a non-coding region of the gene. In some cases, the genomic region of interest can comprise a coding region of the gene and a non-coding region of the gene. If the gene is DNA, the coding region of the gene can be closer to a promoter (upstream) of the gene than a terminator (downstream) of the gene. If the gene is RNA, the coding region of the gene can be closer to a 5' end of the gene than a 3' end of the gene. In some cases, the genomic region of interest can comprise an exon of the gene. The genomic region of interest can be an early position exon within the gene. The early position exon can be an exon that is located within the first half of the gene. The early position exon can be the first, second, third, fourth, fifth, of sixth exon of the gene.

The gene of the genome of the species can be one of a family of genes, and the genomic region of interest that is targeted by the set of gRNAs can comprise the family of genes. In an example, the gene is of the NF-κB (Rel) family of genes comprises RELA, RELB, REL, NFKB1, and NFKB2, and the genomic region of interest can be the NF-κB (Rel) family of genes comprising the five genes. In another example the peroxiredoxin family of genes comprises PRDX1, PRDX2, PRDX3, PRDX4, PRDX5, and PRDX6, and the genomic region of interest can be the peroxiredoxin family of genes comprising the six genes.

The gene of the genome of the species can be one of a pseudogene. The pseudogene can be a processed pseudogene, non-processed pseudogene, unitary pseudogene, and pseudo-pseudogene.

The genomic region of interest that is targeted by the set of gRNAs can comprise one or more coding regions from the family of genes. Each coding region of the one or more coding regions can be represented by (contained in) between 0% to 100% of the family of genes. Each coding region of the one or more coding regions can be represented by at least 0%, 10%, 20%, 30%, 40%, 50%, 60%, 70%, 80%, 90%, 95%, or more of the family of genes. Each coding region of the one or more coding regions can be represented by at most 100%, 90%, 80%, 70%, 60%, 50%, 40%, 30%, 20%, 10%, 5%, or less of the family of genes. In an example, the genomic region of interest comprises one coding region that is represented in all genes of the family of genes.

In some cases, the genomic region is a continuous polynucleotide segment of the gene. The genomic region of interest can range from 1,000 bases or nucleotides (1 kb) to 500 kb. The genomic region of interest can be at least 1 kb, 5 kb, 10 kb, 15 kb, 20 kb, 50 kb, 100 kb, 500 kb, or more. The genomic region of interest can be at most 500 kb, 100 kb, 50 kb, 20 kb, 15 kb, 10 kb, 5 kb, 1 kb, or less.

The identified set of gRNAs that target the genomic region of interest can comprise from 2 to 200 gRNAs. The identified set of gRNAs that target the genomic region of interest can comprise at least 2, 3, 4, 5, 6, 7, 8, 9, 10, 15, 20, 30, 40, 50, 60, 70, 80, 90, 100, 200, or more gRNAs. The identified set of gRNAs that target the genomic region of interest can comprise at least 2 gRNAs. The identified set of gRNAs that target the genomic region of interest can comprise at least 3 gRNAs. The identified set of gRNAs that target the genomic region of interest can comprise at most 200, 100, 90, 80, 70, 60, 50, 40, 30, 0, 15, 10, 9, 8, 7, 6, 5, 4, 3, or less gRNAs. The identified set of gRNAs that target the genomic region of interest can comprise at most 4 gRNAs. The identified set of gRNAs that target the genomic region of interest can comprise at most 3 gRNAs.

Each gRNA in the set of gRNAs that target the genomic region of interest can be hybridizable to a target site in the genomic region of interest that is about 10 to 200 bases (nucleotides) apart from the target site in the genomic region of interest of the at least one other gRNA from the set of gRNAs. Each gRNA in the set of gRNAs that target the genomic region of interest can be hybridizable to a target site in the genomic region of interest that is about 30 to 1000 bases (nucleotides) apart from the target site in the genomic region of interest of the at least one other gRNA from the set of gRNAs. Each gRNA in the set of gRNAs that target the genomic region of interest can be hybridizable to a target site in the genomic region of interest that is at least 30 bases (nucleotides) apart from the target site in the genomic region of interest of the at least one other gRNA from the set of gRNAs. Each gRNA in the set of gRNAs can be hybridizable to a target site in the genomic region of interest that is at least 10, 15, 20, 25, 30, 25, 40, 45, 50, 60, 70, 80, 90, 100, 120, 140, 160, 180, 200 or more bases apart from the target site in the genomic region of interest of the at least one other gRNA from the set of gRNAs. Each gRNA in the set of gRNAs can be hybridizable to a target site in the genomic region of interest that is at most 2000, 1500, 1000, 500, 200, 180, 160, 140, 120, 100, 90, 80, 70, 60, 50, 45, 40, 35, 30, 25, 20, 15, 10, or less bases apart from a target site in genomic region of interest of the at least one other gRNA from the set of gRNAs.

The set of gRNAs can be designed so that the set of gRNAs directs a set of CRISPR/Cas complexes to different target sites within the genomic region of interest in a cell. The CRISPR/Cas complex can create a break in the nucleic acid sequence at the target site. The break can be a double stranded break. The break can be a single stranded break In an example, the set of gRNAs can be designed to direct the set of CRISPR/Cas complexes to knock-out (KO) one or more of the different target sites within the genomic region of interest in the cell. The knock-out can occur as a result of a frameshift mutation introduced by repair of a break caused by the CRISPR/Cas complex. The knock-out can occur as a result of deletion of an exon in a gene of interest. The knock-out can occur as a result of deletion of at least 1, at least 2, at least 3, at least 4, at least 5, at least 6, at least 7, at least 8, at least 9, at least 10, at least 100, at least 1000, or at least 10,000 base pairs in the genomic region of interest. The knock-out can eliminate the function of the gene.

In another example, the set of gRNAs can be designed to direct the set of CRISPR/Cas complexes knock-in (KI) one or more mutations in the different target sites within the genomic region of interest in the cell. The set of CRISPR/Cas complexes can be co-administered with a set of donor polynucleotides for the KI. The knock-in one or more mutations can introduce a point mutation, an allele, a tag, or an exogenous exon into the genome. The point mutation, allele, tag or exogenous exon can be located on the donor polynucleotide. The donor polynucleotide can be incorporated into the genome using homology directed repair (HDR), as described herein. The knock-in one or more mutations can restore function of a previously non-functional gene. The knock-in one or more mutations can improve a function of a gene. The improvement of the function of the gene can be an increase in an amount of a protein produced by the gene. The knock-in can knock-out the function of gene.

In some embodiments, the knock-in one or more mutations can introduce a tag into the genome. The tag can be a detectable tag. The detectable tag can be a fluorescent tag. The detectable tag can be a restriction fragment length polymorphism (RFLP).

In some embodiments, the knock-in one or more mutations can introduce a point mutation into the genome. The point mutation can be an insertion, a deletion, or a substitution of a nucleic acid in the genomic region of interest. In some embodiments, the knock-in one or more mutations can introduce an allele into the genome. The allele can be a transgene.

In some embodiments, the knock-in one or more mutations can introduce an exogenous exon into the genome. The exon can be at least 80%, 85%, 90%, 95%, or 99% identical to an endogenous exon of the target gene. The endogenous exon can be a wild-type exon. The exogenous exon can be an exon comprising at least one mutation relative to the endogenous exon of the target gene. In some embodiments, the knock-in one or more mutations can replace an endogenous exon with an exogenous exon. The exogenous exon can comprise at least one mutation relative to the wild-type exon. The exogenous exon can be in a donor polynucleotide.

In some embodiments, the method further comprises designing at least a second initial set of gRNAs to create a plurality of initial sets of gRNAs. The method can comprise identifying a plurality of initial sets of gRNAs targeting a plurality of genes, wherein each initial set of gRNA in the plurality of initial sets of gRNAs hybridizes different target sites in a gene in the plurality of genes.

Kit of Multiple gRNAs

Another aspect of the present disclosure provides a kit comprising a plurality of gRNAs generated by the aforementioned methods for identifying a set of guide RNAs (gRNAs) that target a genomic region of interest. The kit can comprise a set of gRNAs. Each gRNA in the set can be hybridizable to a different target site within the genomic region of interest. Each gRNA in the set can be hybridizable to a target site in the genomic region of interest that is at least 10 bases apart from the target site in the genomic region of interest of at least one other gRNA from the set of gRNAs. Each gRNA in the set can be hybridizable to a target site in the genomic region of interest that is at least 30 bases apart from the target site in the genomic region of interest of at least one other gRNA from the set of gRNAs. Each gRNA in the set can be hybridizable to a target site in the genomic region of interest that is at most 170 bases apart from the target site in the genomic region of interest of at least one other guide RNA from the set of guide RNAs. Each gRNA in the set can be hybridizable to a target site in the genomic region of interest that is between 30 and 1000 bases apart from the target site in the genomic region of interest of every other guide RNA from the set of guide RNAs. In some embodiments, the set of gRNAs comprises at least 2, at least 3, at least 4, at least 5, at least 10, at least 15, at least 20, or at least 30 gRNAs.

In some embodiments, the kit comprises one set of gRNAs for each of a plurality of genomic regions of interest. The kits described herein can be used to knock-out the genomic region of interest or the plurality of genomic regions of interest. The kits described herein can be used to introduce a donor polynucleotide into the genomic region of interest. The kits described herein can be used to introduce a plurality of donor polynucleotides into the plurality of genomic region of interest.

In some embodiments, the kit comprises at least one donor polynucleotide. In some embodiments, the kit comprises at least one donor polynucleotide for each of a plurality of genomic regions of interest. In some embodiments, the kit comprises a nuclease. The nuclease can be a Cas protein. The Cas protein can be any Cas protein described herein, such as, for example, Cas9, C2c1, C2c3, or Cpf1. In some embodiments, the kit comprises a reagent, such as a buffer. The buffer can be a Tris buffer, Tris-EDTA (TE) buffer, Tris/Borate/EDTA (TBE) buffer, or Tris-acetate-EDTA (TAE) buffer. The kit can comprise RNAase-free $H_2O$. In some embodiments, the kit comprises a transfection reagent. Examples of transfection agents include, but are not limited to, Lipofectamine™ and Oligofectamine™.

In some embodiments, the kit comprises a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the container is formed from a variety of materials such as glass or plastic. The kit can comprise a multi-well plate. The multi-well plate can be a 4-well plate, a 6-well plate, a 12-well plate, a 24-well plate, a 48-well plate, a 96-well plate, or a 384-well plate. In some embodiments, each well in the multi-well plate comprises one gRNA. In some embodiments, each well in the multi-well plate comprises one set of gRNAs targeting a single genomic region of interest. In some embodiments, each well in the multi-well plate comprises a plurality of gRNAs targeting a plurality of genomic regions of interest.

In some embodiments, a kit comprises one or more additional containers, each with one or more of various materials (such as reagents, optionally in concentrated form, and/or devices) desirable from a commercial and user standpoint for use of described herein. Non-limiting examples of such materials include, but not limited to, buffers, primers, enzymes, diluents, filters, carrier, package, container, vial and/or tube labels listing contents and/or instructions for use and package inserts with instructions for use. In some cases, a set of instructions is included. In some cases, a label is on or associated with the container. The label can be on a container when letters, numbers or other characters forming the label are attached, molded or etched into the container itself. The label can be associated with a container when it is present within a receptacle or carrier that also holds the container, e.g., as a package insert. The label can be used to indicate that the contents are to be used for a specific therapeutic application. The label can indicate directions for use of the contents, such as in the methods described herein.

Another aspect of the present disclosure provides a kit comprising a single gRNA generated by the aforementioned methods for identifying a guide RNA (gRNA) that targets a genomic region of interest. The gRNA can be hybridizable to a target site within a genomic region of interest.

Another aspect of the present disclosure provides a kit comprising a plurality of modified cells comprising a modification at a genomic region of interest. The plurality of modified cells can be produced by contacting a plurality of cells with a set of gRNAs generated by the aforementioned methods for identifying a set of guide RNAs (gRNAs) that target the genomic region of interest, in combination with a nuclease and optionally a donor polynucleotide.

Computer System Algorithm

Another aspect of the present disclosure provides a computer system comprising algorithm for performing the aforementioned method for identifying a set of guide RNAs (gRNAs) that target a genomic region of interest. The algorithm can comprise a step of identifying a set of gRNAs. The algorithm can comprise a step of identifying a set of gRNAs for each of a plurality of genomic regions of interest. Each gRNA in the set can be hybridizable to a different target site within the genomic region of interest. Each gRNA in the set can be hybridizable to a target site in the genomic region of interest that is at least 10 bases apart from the target site in the genomic region of interest of at least one other gRNA from the set of gRNAs. Each gRNA in the set can be hybridizable to a target site in the genomic region of interest that is at least 30 bases apart from the target site in the genomic region of interest of at least one other gRNA from the set of gRNAs. Each gRNA in the set can be hybridizable to a target site in the genomic region of interest that is at least 30 bases apart from the target site in the genomic region of interest of at all other gRNA from the set of gRNAs. Each gRNA in the set can be hybridizable to a target site in the genomic region of interest that is at most 170 bases apart from the target site in the genomic region of interest of at least one other guide RNA from the set of guide RNAs. Each gRNA in the set can be hybridizable to a target site in the genomic region of interest that is between 30 and 1000 bases apart from the target site in the genomic region of interest of every other guide RNA from the set of guide RNAs.

Calculating an Off-Target Efficiency

Another aspect of the present disclosure provides a method for selecting at least one guide RNA (gRNA) for hybridizing to a genomic region of interest. The genomic region of interest can be a gene of a genome of a species. The method can comprise, for each of a plurality of gRNAs of an initial set of gRNAs that hybridize to the gene, calculating an off-target value by enumerating a number of mismatches to potential gRNA hybridizing sites in the genome.

The method can utilize the aforementioned computer system comprising the computer readable medium for performing the method for designing one or more gRNAs for hybridizing to a genome region of interest. The genomic region of interest can be a gene of a genome of a species. The computer readable medium can calculate the off-target value by enumerating the number of mismatches to potential gRNA hybridizing sites in the genome.

In some cases, the computer readable medium of the computer system can calculate the off-target value and organize the number of mismatches in shards. When calculating the off-target value of the initial set of gRNAs, the database comprising all possible nuclease (e.g., Cas nuclease) target regions across the genome and/or the reference genome of the species can be partitioned (divided) into a plurality of "shards" (subsets) of the possible Cas nuclease target regions. The initial set of gRNAs can be compared to each of the shards to enumerate mismatches of 0, 1, 2, 3, and/or 4. In contrast to comparing the initial set of gRNAs to one database comprising all the possible Cas nuclease target regions, simultaneously comparing the initial set of gRNAs to each of the shards comprising the subsets of the possible Cas nuclease target regions can improve throughout, speed, and overall performance of calculating the off-target value.

The off-target value can be determined over 100,000 base pairs (bp) or nucleotides to 3,000,000,000 bp of a reference genome or across a reference genome. The off-target value can be determined over at least 100,000 bp, 500,000 bp, 1,000,000 bp, 5,000,000 bp, 10,000,000 bp, 50,000,000 bp, 100,000,000 bp, 500,000,000 bp, 1,000,000,000 bp, 2,000,000,000 bp, 3,000,000,000 bp, or more of the reference genome or across the reference genome. The off-target value can be determined over at most 3,000,000,000 bp, 2,000,000,000 bp, 1,000,000,000 bp, 500,000,000 bp, 100,000,000 bp, 50,000,000 bp, 10,000,000 bp, 5,000,000 bp, 1,000,000 bp, 500,000 bp, 100,000 bp, or less of the reference genome or across the reference genome. In an example, the off-target value can be determined over 1,000,000 bp of the reference genome or across the reference genome.

The database comprising the possible nuclease (e.g., Cas nuclease) target regions of a plurality of genomes and/or reference genomes can have from 1,000 to 1,000,000 nuclease binding sites. The database can have at least 1,000, 10,000, 50,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, or more nuclease binding sites. The database can have at most 1,000,000, 950,000, 900,000, 850,000, 800,000, 750,000, 700,000, 650,000, 600,000, 550,000, 500,000, 450,000, 400,000, 350,000, 300,000, 250,000, 200,000, 150,000, 100,000, 50,000, 10,000, 1,000, or less nuclease biding sites.

The database comprising the possible nuclease (e.g., Cas nuclease) target regions of a plurality of genomes and/or reference genomes can have from 10 million to 300 million nuclease binding sites. The database can have at least 10 million, 25 million, 50 million, 75 million, 100 million, 125 million, 150 million, 175 million, 200 million, 225 million, 250 million, 275 million, 300 million, or more nuclease binding sites. The database can have at most 300 million, 275 million, 250 million, 225 million, 200 million, 175 million, 150 million, 125 million, 100 million, 75 million, 50 million, 25 million, 10 million, or less nuclease biding sites.

Personalized Therapeutics

Another aspect of the present disclosure provides a method for designing one or more guide RNAs (gRNAs) for hybridizing to a genomic region of interest in an individual. The method can comprise using the individual's genome to determine gRNA target site potentials. The method can comprise determining, for each gRNA target site potential, an off-target value for a prospective guide RNA. The method can comprise identifying one or more gRNAs with an improved utility index.

In some cases, the method can comprise using a genome of a population of individuals to determine gRNA target site potentials. Examples of the population of individuals include a set of individuals in a range of ages (e.g., teenager, 65 years or older, etc.), a set of individuals diagnosed with the same condition (e.g., a patient population with muscular dystrophy, Parkinson's disease, etc.), a set of individuals undergoing the same disease treatment (e.g., a cohort of subjects diagnosed and/or treated for breast cancer, prostate cancer, etc.), etc. Such method can identify gRNA target site potentials for each individual, a subset of individuals from the population of individuals, and/or the whole population of individuals.

In some cases, the software and methods described herein are used to make a selection and/or recommendation of a gRNA that can be used in a CRISPR system across a patient cohort and/or in a specific patient demographic. For example, a therapeutic agent comprising a CRISPR system with an activated or deactivated endonuclease can be administered to a subject that has been selected using the methods and systems herein. A determination that a gRNA would result in a number of off-target binding exceeding a threshold would result in lack of selection of the patient for treatment or a recommendation of another treatment. A determination that a gRNA would result in a number of off-target binding less than a threshold would result in selecting the patient for treatment or recommending such a treatment to the patient.

In some instances, any of the methods and systems herein are used for identifying a gRNA that is present in one, some, or all subjects in a population or that is capable of binding to target site in one, some or all subjects in a population, preferably with a reduced off-target value. This would also cover the calculation of the off-target values for a selected gRNA across all subjects in the population.

A gRNA designed from a reference assembly can be evaluated using information derived from a clinical study as described herein or using genomic information from a plurality of individuals (e.g., at least 10, 100, 1,000, 10,000, or 100,000). For example, a clinical study can involve sequencing the genome of a set of subjects having a condition to be treated and/or normal, and determining the off-target values for a test gRNA across the genomes of the above individuals. In some cases, a gRNA designed from a single reference genome (e.g., an individual) can be evaluated for its off-target activity across one, some, or all subjects in a population. This can be done for example, for designing a new therapeutic agent using a reference genome and evaluating its possible efficiency or efficacy in a subject, set of subjects or across a population or demographic of individuals using the methods and systems herein. The gRNA can be further modified to increased stability, pK, delivery, reduced off-target value or reduced off-target affect.

In one instance, a clinical study can involve sequencing the genome of at least one subject in a set of subjects having a condition to be treated and/or normal, designing a gRNA based on the genome of the at least one subject, and determining the off-target values for the designed gRNA across one, some, or all subjects in the set of subjects.

The method for designing the one or more gRNAs for hybridizing the genomic region of the individual can utilize the aforementioned method for designing one or more gRNAs for hybridizing to a genomic region of interest. The genomic region of interest can be a gene of a genome of a species. The method can further comprise receiving the genome of the individual and/or the genome of the population of individuals (e.g., from user input via a user interface on a user device, or from a database). The method can further comprise identifying, from the genome, all possible target regions (or target loci) that comprise a protospacer (target site), a protospacer adjacent motif (PAM) that is recognized by one or more types of Cas enzymes, and the opposite strand of the protospacer (binding site). The method can further comprise isolating the identified target regions in the genomic region of interest. The isolated target regions can be the target site potentials. In an example, the genomic region of interest can be a specific site within a T-cell genome of an immune cell of the individual or the population of individuals to reduce the risk of gene insertion at incorrect or undesired locations.

The method can further comprise identifying an initial set of gRNAs that hybridize the target site potentials of the individual or the population of individuals. The method can further comprise calculating an off-target value and/or an on-target efficiency of each gRNA of the initial set of gRNAs to determine the utility index of each gRNA. In some cases, the utility index can be a therapeutic index. In some cases, the therapeutic index comprises reduction of off-target binding that can be assessed by the off-target value and/or the on-target efficiency. As such, in some cases, different threshold values of the off-target value and the open target efficiency can be used to identify the one or more gRNAs with an improved utility index. Thus, the method can further comprise editing a cell with the one or more gRNAs with the improved utility index.

In some cases, the therapeutic index comprises reduction of not only off-target binding, but also increased on-target efficiency, increased knock-out (KO) efficiency, increased knock-in (KI) efficiency, or modulation of CRISPR interference in at least one cell of the individual or the population of individuals. In an example, the one or more gRNAs can be designed to KO a gene in the genomic region of a cell of the individual or the population of individuals. In another example, the one or more gRNAs can be designed to KI a mutation in the genomic region of a cell of the individual or the population of individuals.

In some cases, the individual can be a human. In some cases, the individual can be a non-human (e.g., a mouse, rat, etc.) In some cases, the individual (or the individuals in the population of individuals) can be afflicted with a condition. The condition can be known or predicted to be related to a number of disease-associated genes, and the one or more gRNAs of the present disclosure can direct one or more CRISPR/Cas systems to the number of disease-associated genes. The number of disease-associated genes can comprise any gene or polynucleotide which is yielding transcription or translation products at an abnormal level or in an abnormal form in cells derived from a disease-affected tissues compared with tissues or cells of a non-disease control. An example can be a gene that becomes expressed at an abnormally high level. Another example can be a gene that becomes expressed at an abnormally low level, where the altered expression correlates with the occurrence and/or progression of the disease. Alternatively or in addition to, the number of disease-associated genes can comprise any gene possessing mutations.

Examples of the number of disease-associated genes include Alzheimer's disease, Parkinson's disease, multiple sclerosis, spinal muscular dystrophy, muscular dystrophy, diseases affecting myeloid cells, chronic lymphocytic leukemia, multiple myeloma, malignant tumors, melanomas, cystic fibrosis, hemophilia, sickle cell disease, and cancers of various organs including breast, intestine, prostate, central nervous system, glioblastoma, and sarcoma.

The method of determining of the gRNA target site potentials and the identifying of the one or more gRNAs can be performed by a computer. The computer can be the aforementioned computer system comprising the computable medium for performing the method for designing one or more gRNAs for hybridizing to a genomic region of interest.

Personalized Diagnostics

Another aspect of the present disclosure provides a method for assessing off-target effect of a CRISPR agent on an individual. The method comprises, using the individual's genome, determining by a computer the off-target value of the CRISPR agent by enumerating a number of mismatches to potential target sites in the individual's genome.

This can be useful, for example, in clinical trial settings, to select patients to be included or excluded from a clinical trial, or treatment. For example, a patient whose personal genome has a larger number of off-target binding sites than a threshold value (e.g., 0, 1, 2, 3, etc) is excluded from a clinical trial or from a treatment regimen, while a patient whose personal genome has a smaller or no off-target binding sites is included in the clinical trial or receives treatment.

The method for assessing off-target effect of the CRISPR agent on the individual can utilize the aforementioned computer system comprising the computer readable medium for performing the method for designing one or more gRNAs for hybridizing to a genomic region of interest. The genomic region of interest can be a gene of a genome of a species. The method can further comprise outputting a report that enumerates the number of mismatches to potential target sites in the individual's genome. In some cases, the outputting can be displayed on a screen (e.g., via a user interface on a user device such as a personal computer).

The CRISPR agent can be a therapeutic agent. The therapeutic agent can be a gRNA from the one or more gRNAs for hybridizing the gene of the genome of the species. The gRNA can direct a CRISPR/Cas complex to a target region. The therapeutic agent can have a wide variety of utility including modifying (e.g., deleting, inserting, translocating, inactivating, activating) a target region in a multiplicity of cell types. As such, the therapeutic agent can have a broad spectrum of applications including, but are not limited to, gene therapy, drug screening, disease diagnosis, and prognosis.

The number of potential target sites in the individual's genome can range from 1,000 to 3,000,000. The number of potential target sites in the individual's genome can be at least 1,000, 10,000, 100,000, 200,000, 300,000, 400,000, 500,000, 600,000, 700,000, 800,000, 900,000, 1,000,000, 2,000,000, 3,000,000, or more. The number of potential target sites in the individual's genome can be at most 3,000,000, 2,000,000, 1,000,000, 900,000, 800,000, 700,000, 600,000, 500,000, 400,000, 300,000, 200,000, 100,000, 10,000, 1,000, or less.

High Efficiency and Precision Methods for Editing

An aspect of the present disclosure provides a method for editing a cell or a population of cells, comprising: contacting a cell or population of cells with the one or more sets of gRNAs, in combination with a nuclease and optionally a donor polynucleotide, to produce a population of modified cells. The population of modified cells can comprise at least one edit in at least one genomic region of interest. The one or more sets of gRNA can be designed by any of the methods described herein. The at least one edit can result in a knock-out of a gene in the genomic region of interest or a knock-in of a point mutation, an allele, a tag, or an exogenous exon into the genome at the genomic region of interest. Another aspect of the present disclosure provides a method for screening a cell or a population of modified cells comprising at least one edit in at least one genomic region of interest produced by at least one set of gRNAs. The editing efficiency of one or more sets of gRNA comprising at least two gRNAs can be higher than an individual editing efficiency of each of the at least two gRNAs.

In some embodiments, the method for editing a plurality of genomic regions of interest in a population of cells, comprises: contacting the population of cells with: (i) a plurality of sets of gRNA targeting a plurality of genomic regions of interest and (ii) a nuclease; wherein after the contacting at least 50% of the cells in the population of cells comprise an edited genotype different from a wild-type genotype at each of the genomic regions of interest. In some embodiments, a method for editing a plurality of genomic regions of interest in a population of cells, comprises contacting each of a subset of the population of cells with: (i) a set of gRNAs from a plurality of sets of gRNAs, where each set of gRNAs in the plurality of sets of gRNAs targets a different genomic region of interest from the plurality of genomic regions of interest and (ii) a nuclease. In some embodiments, after the contacting at least 80% of the cells in at least 50% of the subsets of the population of cells comprise an edited genotype different from a wild-type genotype at the genomic region of interest. In some embodiments, after the contacting at least 70% of the cells in each of the subsets of the population of cells comprise an edited genotype different from a wild-type genotype at the genomic region of interest. Each set of gRNA can comprise three gRNAs. In some cases, at least 50%, 60%, 60%, 70%, 80%, 90%, or 95% of the sets of gRNAs comprises at least three gRNAs. Each gRNA in a set of gRNA can comprise an inter-guide spacing of at least 30 bases. Each gRNA in a set of gRNAs can be hybridizable to a target site in the genomic region of interest that is at least 30 bases from the target site of all other gRNA from the set of gRNAs.

The method can comprise designing one or more sets of guide RNAs (gRNAs) for hybridizing to a genomic region of interest, as described herein. The population of modified cells can comprise at least one cell. The at least one cell can be a mammalian cell, a fish cell, an insect cell, a plant cell, or a microorganism. The microorganism can be a bacterium. The at least one cell can be a cell in a cell line as described herein. The at least one cell can be a tumor cell. The at least one cell can be derived from an individual.

The method can comprise contacting a cell or population of cells with the one or more sets of gRNAs and a nuclease, to produce a modified cell or a population of modified cells. The method can further comprise contacting the cell or population of cells with a donor polynucleotide. The contacting can comprise transfecting the one or more sets of gRNAs, the nuclease or a polynucleotide encoding the nuclease, or the combination thereof into the cell or population of cells. In some embodiments, the each gRNA in the one or more sets of gRNAs is complexed with a Cas protein prior to the transfecting, to produce a Cas-gRNA complex, also referred to herein as CRISPR/Cas complex or CRISPR/Cas system. In some embodiments, the method further comprises transfecting at least one donor polynucleotide into the cell or population of cells. The transfecting can be a nonviral transfection or viral transfection. The nonviral transfection can be electroporation, lipofection, or microinjection. The viral transfection can comprise the use of a viral vector. The viral vector can be a retroviral vector, an adenoviral vector, an adeno associated virus (AAV) vector, an alphavirus vector, a vaccinia virus vector, a herpes simplex virus (HSV) vector, a lentivirus vector, or a retrovirus vector. The viral vector can be a replication-competent viral vector or a replication-incompetent viral vector.

The genomic region of interest can be a gene. The gene can be a gene in a pathway of interest. The method can comprise targeting a plurality of genomic regions of interest. The plurality of genomic regions of interest can comprise a plurality of genes in a pathway of interest. The plurality of genomic regions of interest can comprise a plurality of genes in a plurality of pathways of interest. The pathway of interest can be a metabolic pathway, a signal transduction pathway, or a gene-regulation pathway. The pathway of interest can be a pathway involved in a disease. The disease can be a cancer. The pathway of interest can be a pathway involved in production of a molecule of interest. The molecule of interest can be a molecule with pharmacological activity. The genomic region of interest can be a non-coding region of the genome. The non-coding region can be a regulatory element. The regulatory element can be a cis-regulatory element or a trans-regulatory element. The cis-regulatory element can be a promoter, an enhancer, or a silencer.

In some embodiments, the method comprises contacting a set of gRNAs targeting a genomic region of interest with a subset of the population of modified cells. In some embodiments, the method comprises contacting each of a plurality of sets of gRNAs targeting a genomic region of interest with each of a plurality of subsets of the population of modified cells. In one example, a plurality of subsets of the population of modified cells can be placed in each well of a multi-well plate. The multi-well plate can be a 4-well plate, a 6-well plate, a 12-well plate, a 24-well plate, a 48-well plate, a 96-well plate, or a 384-well plate. The subset of the population of modified cells can comprise at least $10^2$, at least $10^3$, at least $10^4$, at least $10^5$, or at least $10^6$ cells. Each well of the multi-well plate can further comprise a set of gRNA targeting the genomic region of interest. Each set of gRNAs in each well of the multi-well plate can target different genomic regions of interest. The plurality of sets of gRNAs can target at least 5, at least 10, at least 20, at least 50, or at least 100 different genomic regions of interest. In some embodiments, the contacting occurs in each well of the multi-well plate.

In some embodiments, the method comprises contacting the population of modified cells or subset of the population of modified cells with a stimulus. The stimulus can be an additional agent. The additional agent can be a therapeutic agent (for example: an antibiotic, biologic, or a small molecule drug) or an agent to induce a disease state in the modified cell.

In some embodiments, the method comprises detecting a phenotype of the population of modified cells or subset of the population of modified cells. The phenotype can be cell viability. The phenotype can be an editing efficiency of the set of gRNAs. The phenotype can be an amount of a molecule of interest produced by the population of modified cells or subset of the population of modified cells. The molecule of interest can be a protein or a transcript encoding a protein. In some embodiments, the method comprises detecting a tag of the population of modified cells or subset of the population of modified cells.

Validating a gRNA

The other aspect of the present disclosure provides a method for validating a prospective gRNA. The method can comprise determining a number of off-target hits for the prospective gRNA in a genome or part of the genome. The method can comprise, using the number of off-target hits, calculating an off-target value for the prospective gRNA. The method can comprise predicting activity of the prospective gRNA using the off-target value.

The method for validating the prospective gRNA can utilize the aforementioned method for designing one or more gRNAs for hybridizing to a genomic region of interest. The genomic region of interest can be a gene of a genome of a species. Alternatively or in addition to, the method for validating the prospective gRNA can further utilize the aforementioned computer system comprising the computer readable medium for performing (1) the method for designing one or more gRNAs for hybridizing to a genomic region of interest, (2) the method for identifying a set of gRNAs that target a genomic region of interest, and (3) the method for selecting at least one gRNA for hybridizing to a genomic region of interest.

Figure 6:
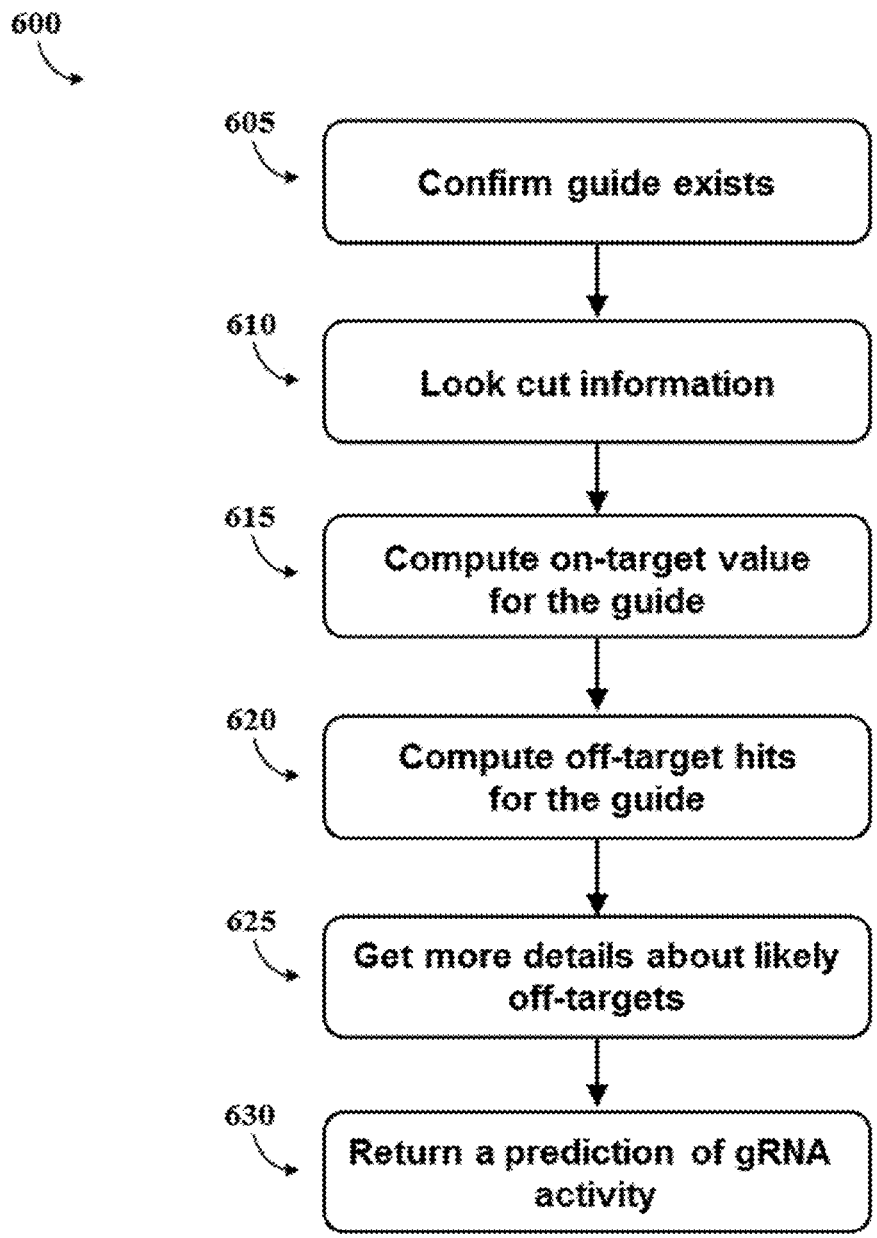
FIG. 6 shows an example of a flowchart of a method of validating one or more guides for hybridizing to a gene of a genome of a species.

FIG. 6 shows an example of a flowchart 600 of a method of validating one or more guides (e.g., gRNAs) for hybridizing to a gene of a genome of a species. The method comprises: (a) confirming that the guide exists (e.g., confirming that a complimentary sequence of the gRNA provided by a user exists in the genome of the species) 605; (b) look cut information (e.g., confirm that the complementary sequence of the gRNA in the genome is next to a protospacer adjacent motif (PAM) site) 610; (c) compute on-target value for the gRNA (e.g., calculate an azimuth score for the gRNA) 615; (d) compute off-target hits for each guide 620; (e) get more details about likely off-targets (e.g., enumerating the number of mismatches for each of the gRNAs as compared to a plurality of possible Cas target regions across the genome) 625; and (f) return a prediction of the gRNA activity 630. In some cases, the order of the steps (c) and (d-e) can be interchangeable.

User Interface

The other additional aspect of the present disclosure provides a computer system. The computer system can comprise a user interface system for selecting of a species of interest and a gene of interest from the species of interest. The computer system can comprise a design module integrated with the user interface for identifying one or more small guide RNA (gRNA) sequences for the gene of interest. The computer system can comprise an output system for displaying selected small gRNAs or gRNAs comprising the small gRNAs. Each small gRNA can be about 20 bases or nucleotides of each gRNA. The computer system can comprise an activation unit for initiating synthesis by an RNA synthesizer of the one or more small gRNAs.

The design module of the computer system can perform the aforementioned method for validating the prospective gRNA can utilize the aforementioned method for designing one or more gRNAs for hybridizing to a genomic region of interest.

The user interface system can include a selection of 100 to 500,000 different reference genomes. The user interface system can include a selection of at least 100, 1,000, 10,000, 100,000, 500,000, or more different reference genomes. The user interface system can include a selection of at most 500,000, 100,000, 10,000, 1,000, 100, or less different reference genomes. The different reference genomes can be stored in the cloud (e.g., one or more databases in Amazon Web Services Could). The design module of the computer system can have accesses to the reference genomes in the cloud.

The design module of the computer system can have accesses to between 10,000 to 120,000 reference genomes. The design module of the computer system can have accesses to at least 10,000, 20,000, 30,000, 40,000, 50,000, 60,000, 70,000, 80,000, 90,000, 100,000, 110,000, 120,000, or more reference genomes. The design module of the computer system can have accesses to at most 120,000, 110,000, 100,000, 90,000, 80,000, 70,000, 60,000, 50,000, 40,000, 30,000, 20,000, 10,000, or less reference genomes.

The user interface of the computer system can further comprise a genomic data receiving module for obtaining input of an individual's genome. The genomic data receiving module can obtain the individuals genome or part of the user's genome from a server (e.g., a personal genomic service's server) or from a file uploaded by a user.

Figure 7A:
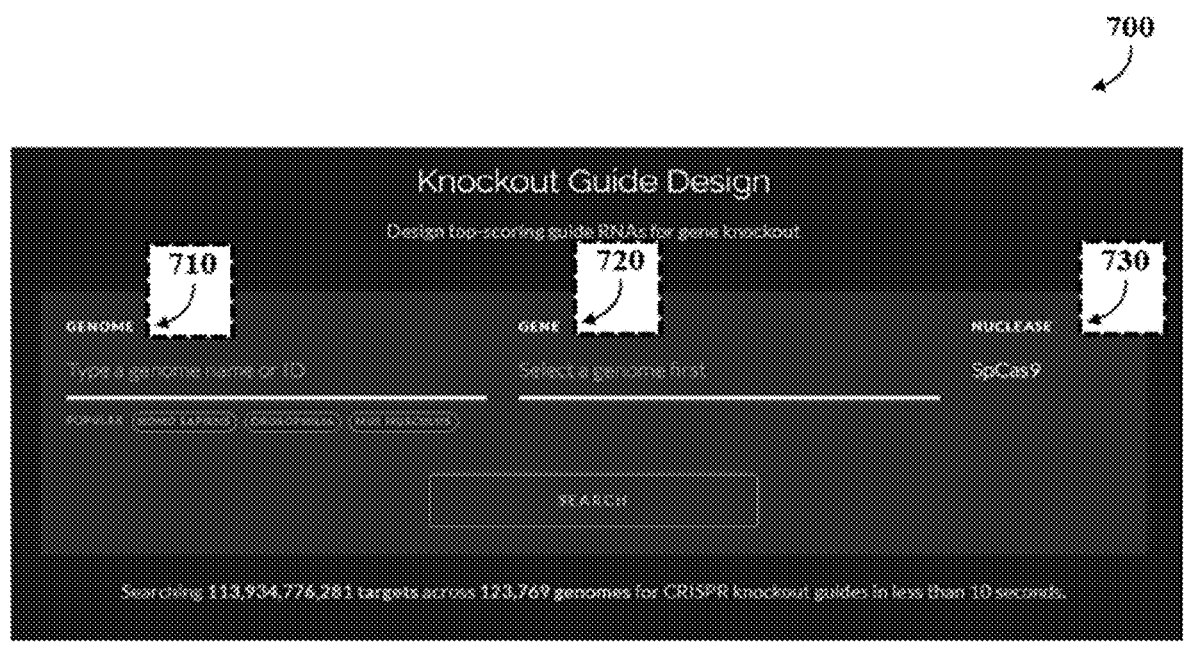
FIGS. 7A-7D illustrate examples of a window of a graphical user interface (GUI) for selecting a genome and a gene of interest to request designing of one or more guides for hybridizing the gene of the genome.
Figure 7B:
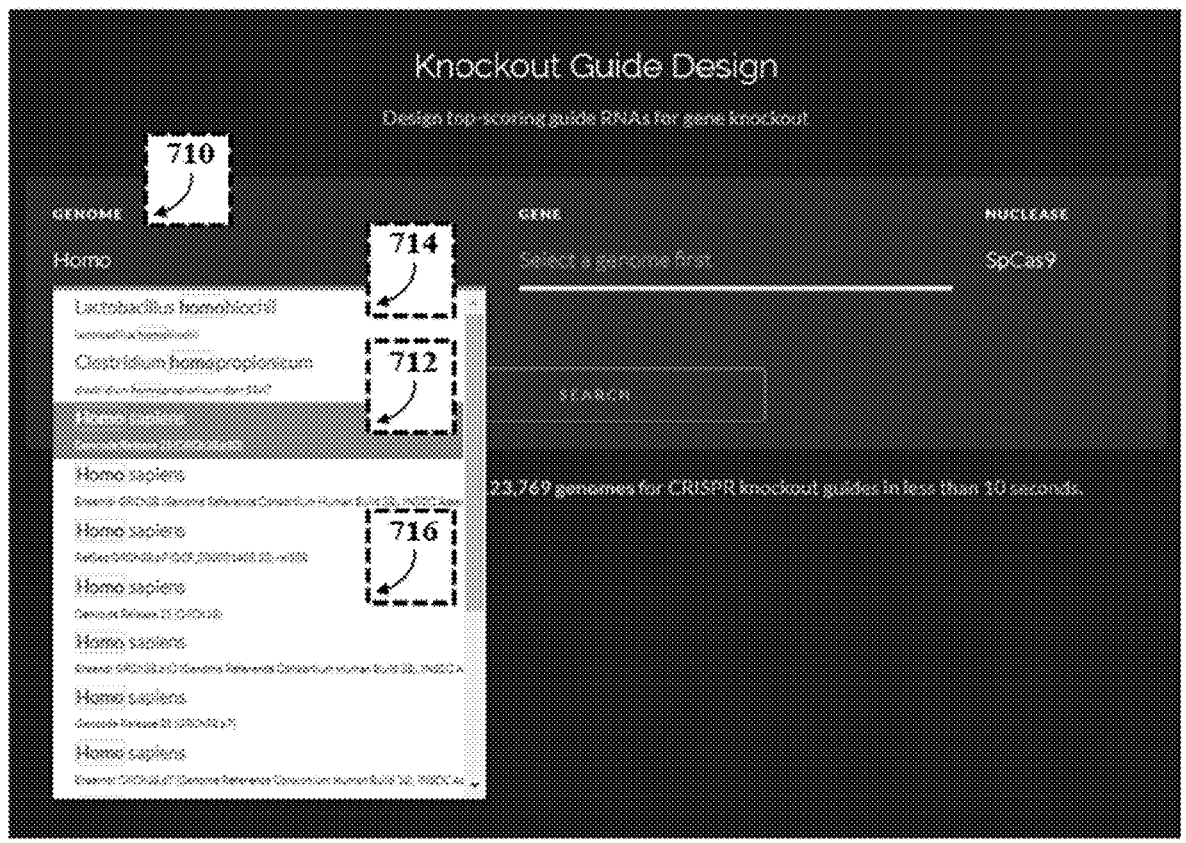
Figure 7C:
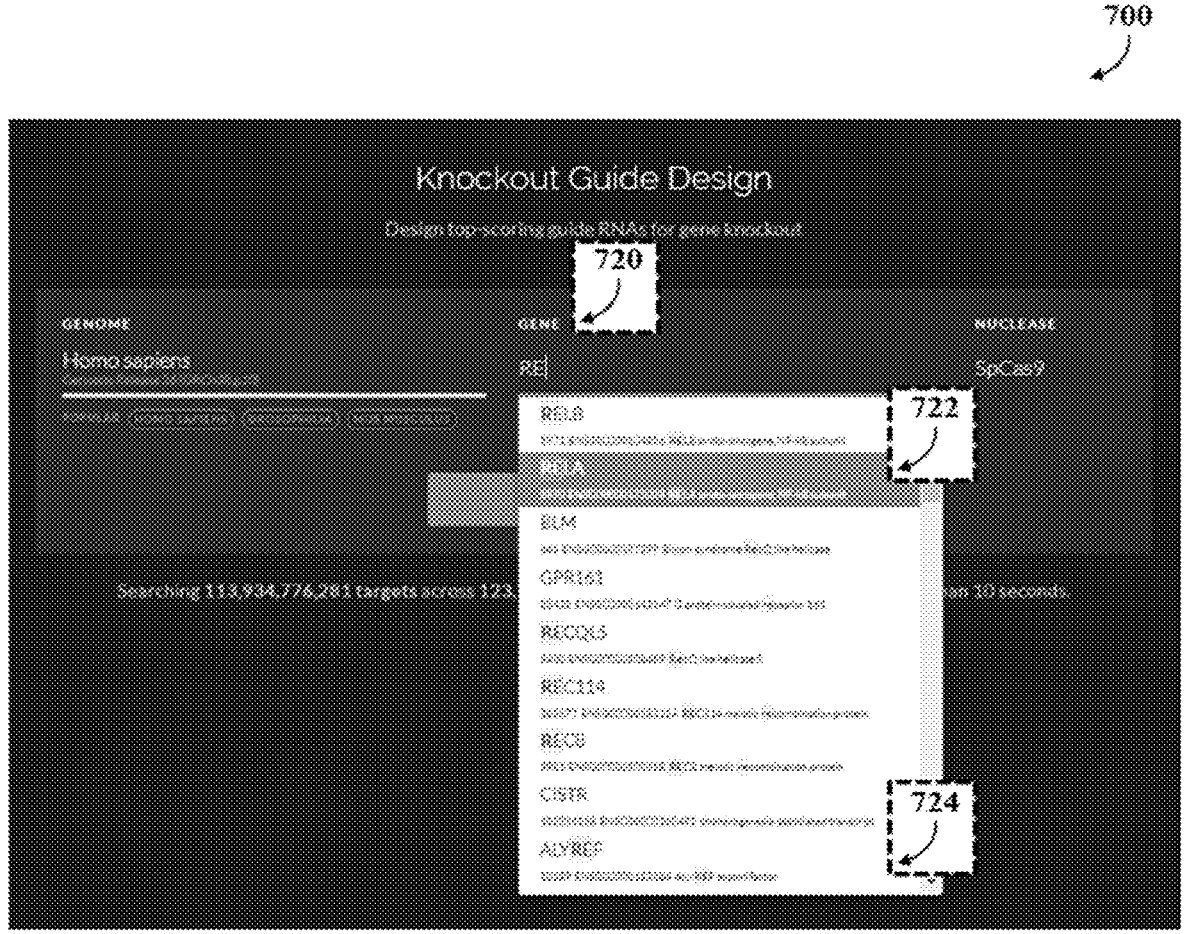
Figure 7D:
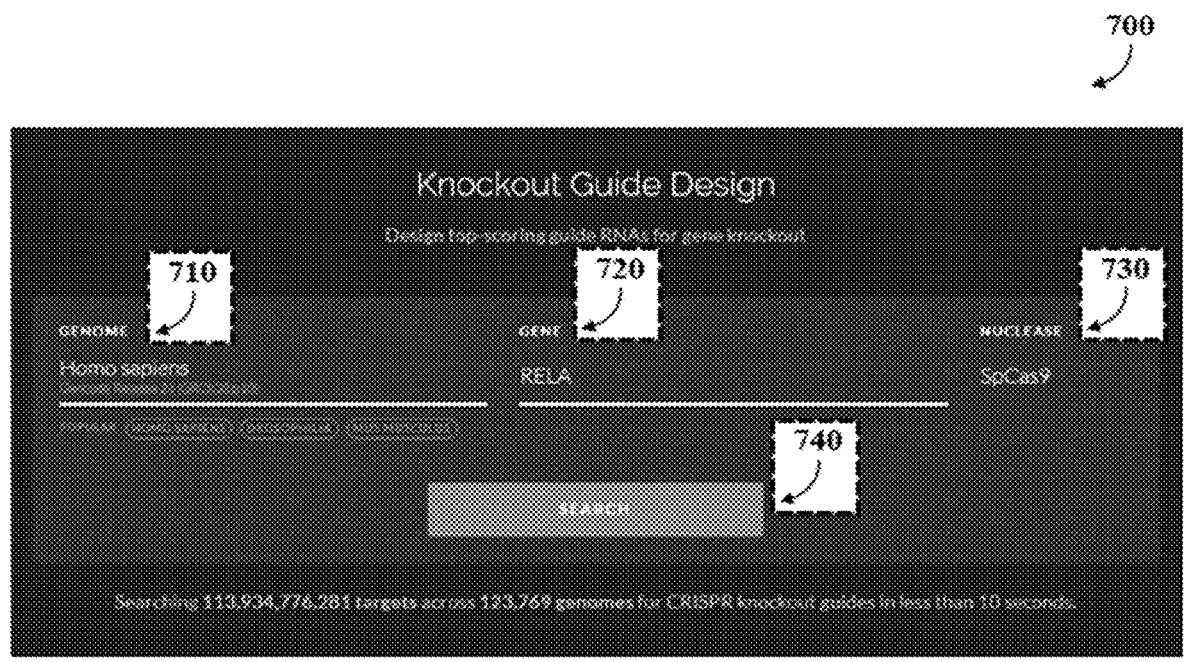

FIG. 7A-D illustrate examples of a window of a graphical user interface (GUI) for selecting a gene of a genome of a species of interest to request designing of one or more gRNAs for hybridizing the gene. The one or more gRNAs can be designed to direct a CRISPR/Cas system for knockout of the gene of interest. FIG. 7A shows the window of the GUI 700 for Knockout Guide Design that allows the user to type in the name or the identifier number of the genome 710 and the gene 720 of interest. In this GUI, the nuclease of use 730 is pre-selected to be *Streptococcus pyogenes* Cas9 (SpCas9). In some cases, the user can select a Cas enzyme of interest. FIG. 7B shows a window the GUI for Knockout Guide Design 700. When the user types in a portion of the binomial nomenclature of the genome of interest (e.g., "Homo"), the software of the GUI 700 can suggest to the user a list of available genomes that comprise the word "Homo" in the genus (e.g., *Homo sapiens*, 712) or in the species (*Lactobacillus homohiochii*, 714). The software of the GUI 700 can also suggest different types of the same genome (e.g., *Homo sapiens* genome from "Genecode Release 26" 712 and *Homo sapiens* genome from "Genecode Release 21" 716). The user can then select the correct binomial nomenclature of interest. Alternatively or in addition to, the user can type in the binomial nomenclature of interest in full. FIG. 7C shows a window of the GUI for Knockout Guide Design 700. When the user types in a portion of the abbreviation and/or full name of the gene of interest (e.g., "RE"), the software of the GUI 700 can suggest to the user a list of available genes that comprise the typed input (e.g., "RELA" 722 or "ALYREF" 724). The user can then select the correct gene of interest. Alternatively or in addition to, the user can type in the name of the gene of interest in full. FIG. 7D shows a window of the GUI for Knockout Guide Design 700. Once the genome 710, the gene 720, and the nuclease 730 are selected, the user can click the search button 740 to direct the software of the GUI to initiate the method for designing one or more gRNAs for hybridizing the gene of the genome of the species of interest.

Figure 8:
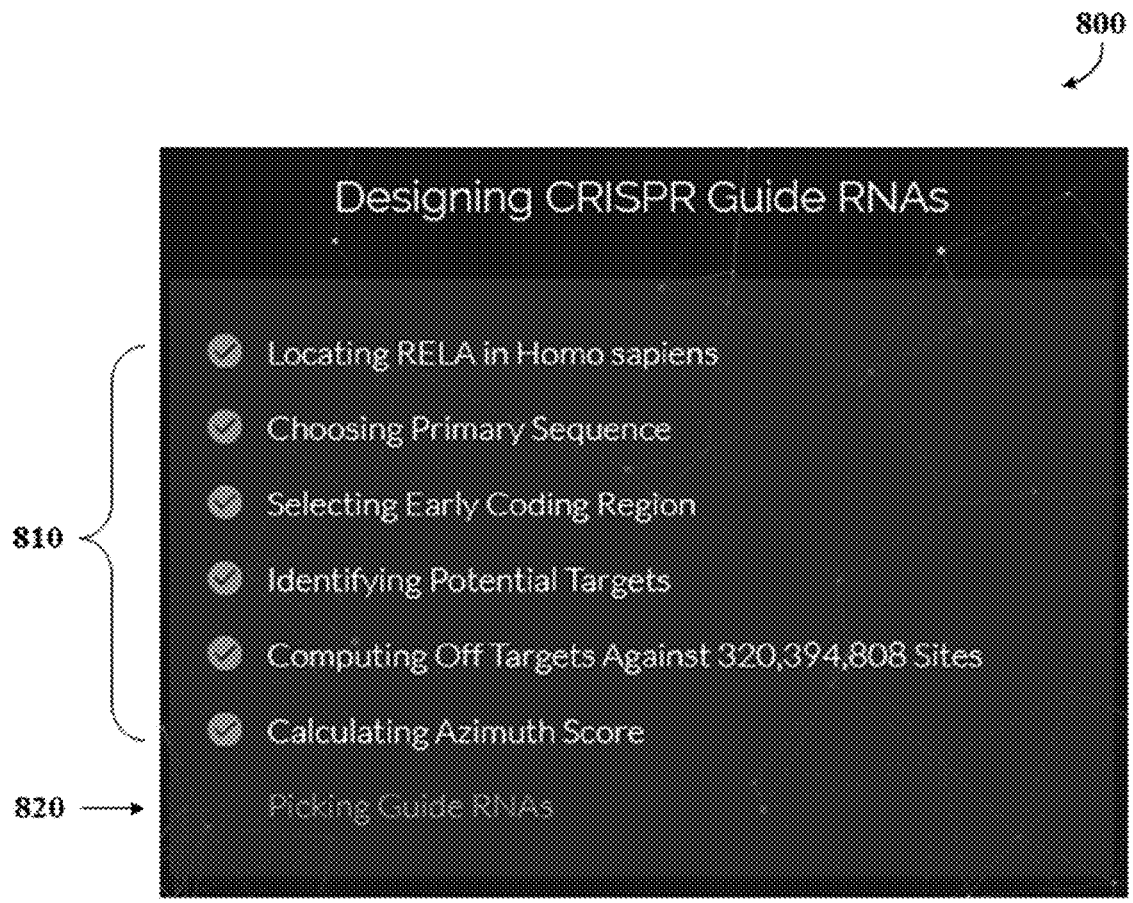
FIG. 8 illustrates an example of a window of the GUI for displaying a progress of designing one or more guides for hybridizing the gene of the genome of interest.

FIG. 8 illustrates an example of a window 800 of the GUI for displaying a progress of designing one or more gRNAs for hybridizing the gene of the genome of interest. The window 800 shows a list of steps of the method for designing the one or more gRNAs. The window can show the progress by marking the steps that have been employed 810 and leaving the remaining steps unmarked 820.

FIG. 9A-D illustrate examples of a window of the GUI for displaying one or more gRNAs that are designed to hybridize the gene of the genome of interest. FIG. 9A shows a window 900 of the GUI. The window 900 provides a summary 910 of the results of designing the one or more gRNAs (e.g., a number of Cas target sites in the gene of interest, a number of top ranked gRNAs that can be used for the gene knock-out, etc.). The window 900 provides hybridizing polynucleotide sequences of the top ranked gRNAs 920. The window 900 also provides a schematic of a selected coding region 930 of the gene (e.g., exon 3 of the RELA gene) that was used to generate the one or more gRNAs, as well as the hybridizing locations 940 of the top ranked gRNAs 920 within the selected region 930 of the gene. FIG. 9B shows the window 900 of the GUI. When the user selects a gRNA 922 from the top ranked gRNAs 920, the GUI highlights the respective hybridizing location 942 of the selected gRNA 922 in the selected coding region 930 of the gene. Furthermore, as shown in FIG. 9C, the window 900 also shows details 944 about the selected gRNA 922, including the target polynucleotide sequence, the Cas cutsite (cleave site) within the genome of the species, the selected coding region position, the on-target value, and the off-target value. FIG. 9D shows a window 905 of the GUI. The window 905 displays additional gRNAs from the one or more of gRNAs that are designed to hybridize the gene of the genome of interest. The user can be able to select at least one from the additional gRNAs for further analysis and/or purchase.

Figure 10A:
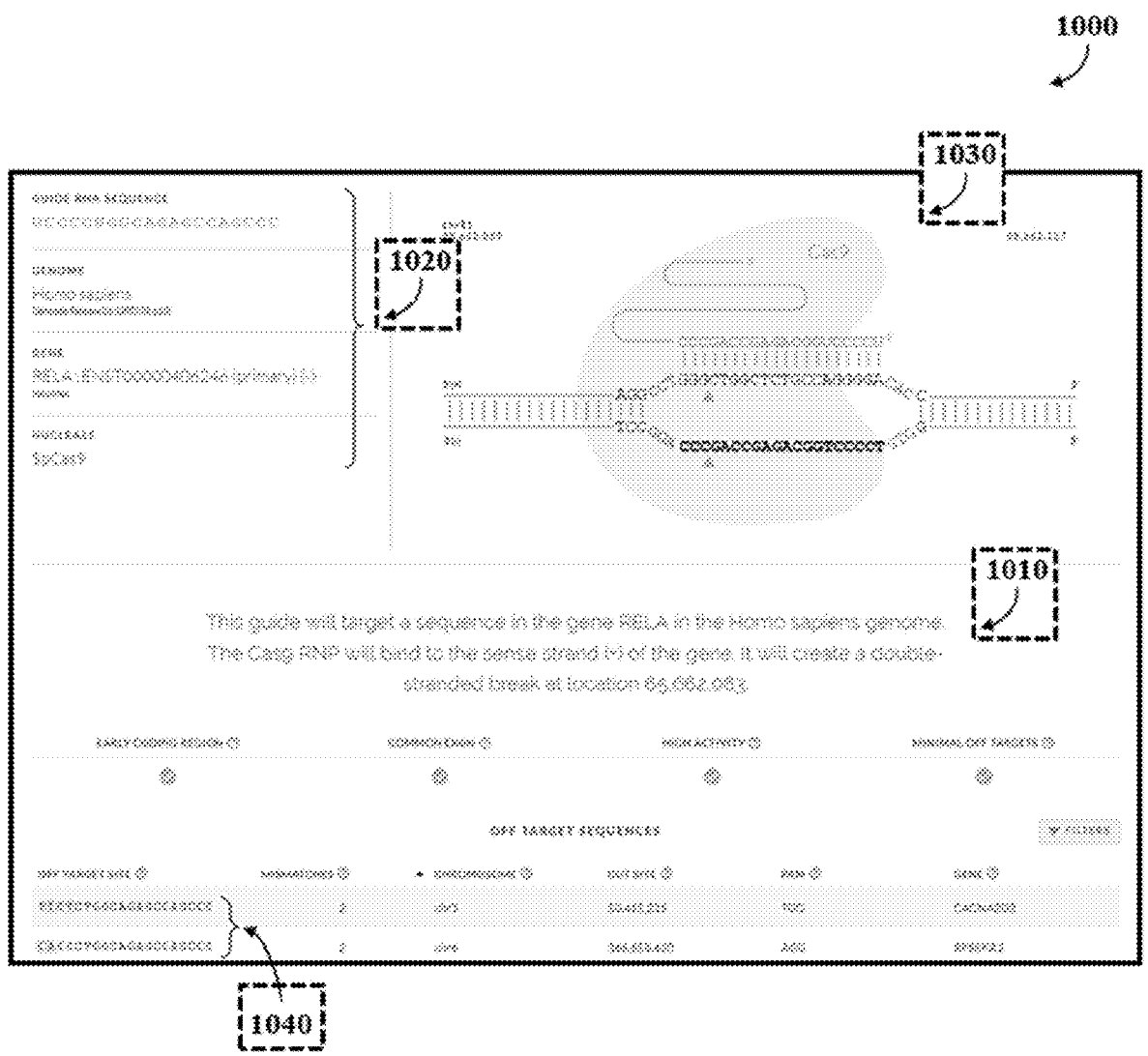
Figures 10B, 10C, 10D:
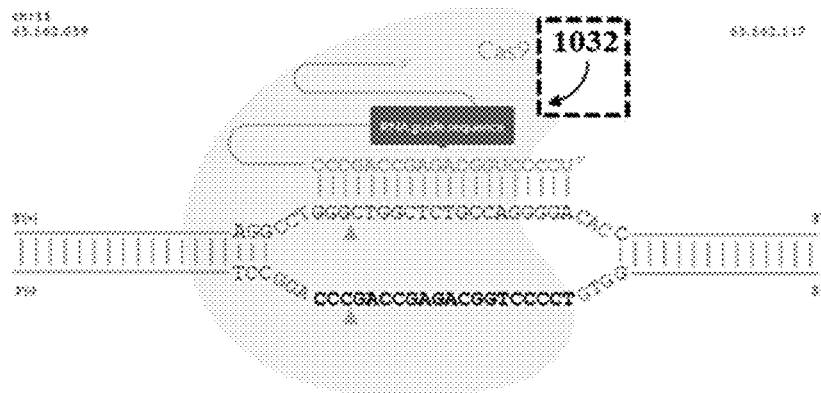
Figure 10E:
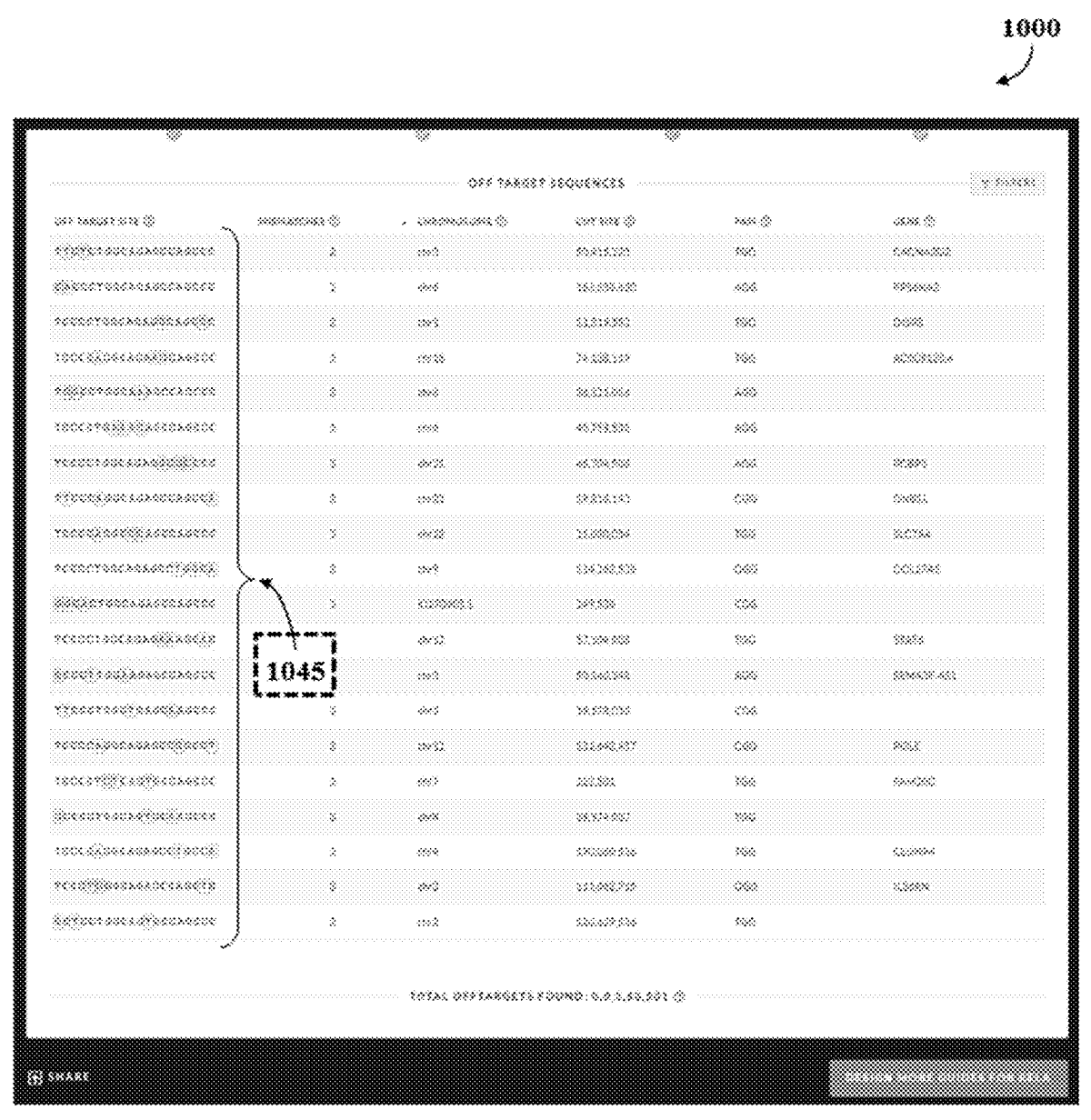

FIG. 10A-E illustrate examples of a window of the GUI for displaying detailed information about a gRNA designed to hybridize the gene of the genome of interest. When the user selects a designed gRNA (e.g., the gRNA 922 in FIG. 9C), the user is directed to a new GUI window 1000, as shown in FIG. 10A. The window 1000 provides a summary 1010 of the performance the selected gRNA (e.g., the target gene of the gRNA, the location of the cut site within the genome, etc.). The window 1000 also shows other details 1020 including the selected gRNA sequence, genome, gene, and nuclease selected for the analysis. Furthermore, the window 1000 shows a schematic 1030 of the Cas-gRNA complex that drawn to interact with the target region of the gene of interest. The window 1000 also shows examples of off-target sites 1040 of the selected gRNA with accompanying information including a number of mismatches between the selected gRNA and each of the off-target site, the position of the off-target site within the genome, and the name of the gene comprising the off-target site (a list of additional off-target sites 1045 of the selected gRNA shown in FIG. 10E). When the user chooses different portions of the schematic 1030, the GUI can inform the user which part of the schematic 1030 is displaying the RNA guide sequence (FIG. 10B, 1032), the protospacer adjacent motif (PAM) site in the target site (FIG. 10C, 1034), and the target site sequence (FIG. 10D, 1036).

Figure 11A:
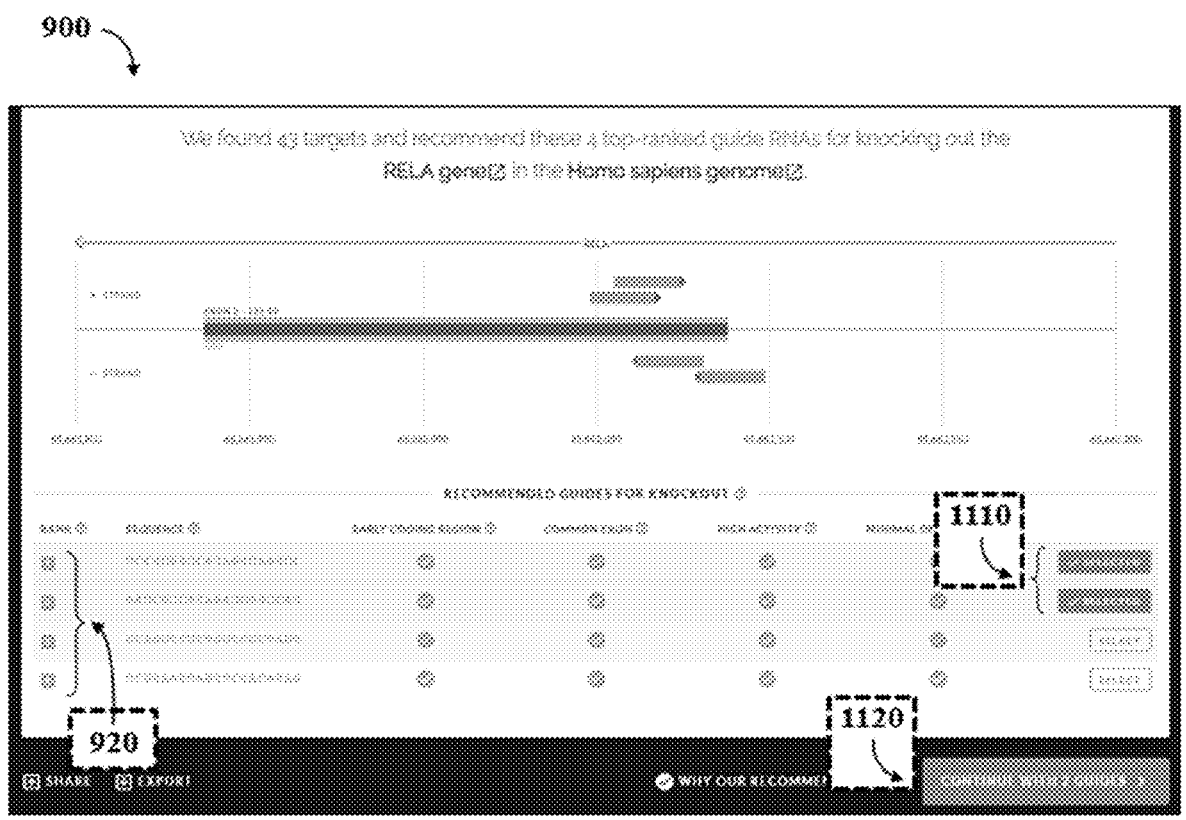
FIGS. 11A-11B illustrate examples of a window of the GUI for selecting and purchasing a subset of the one or more guides that are designed to hybridize the gene of the genome of interest.
Figure 11B:
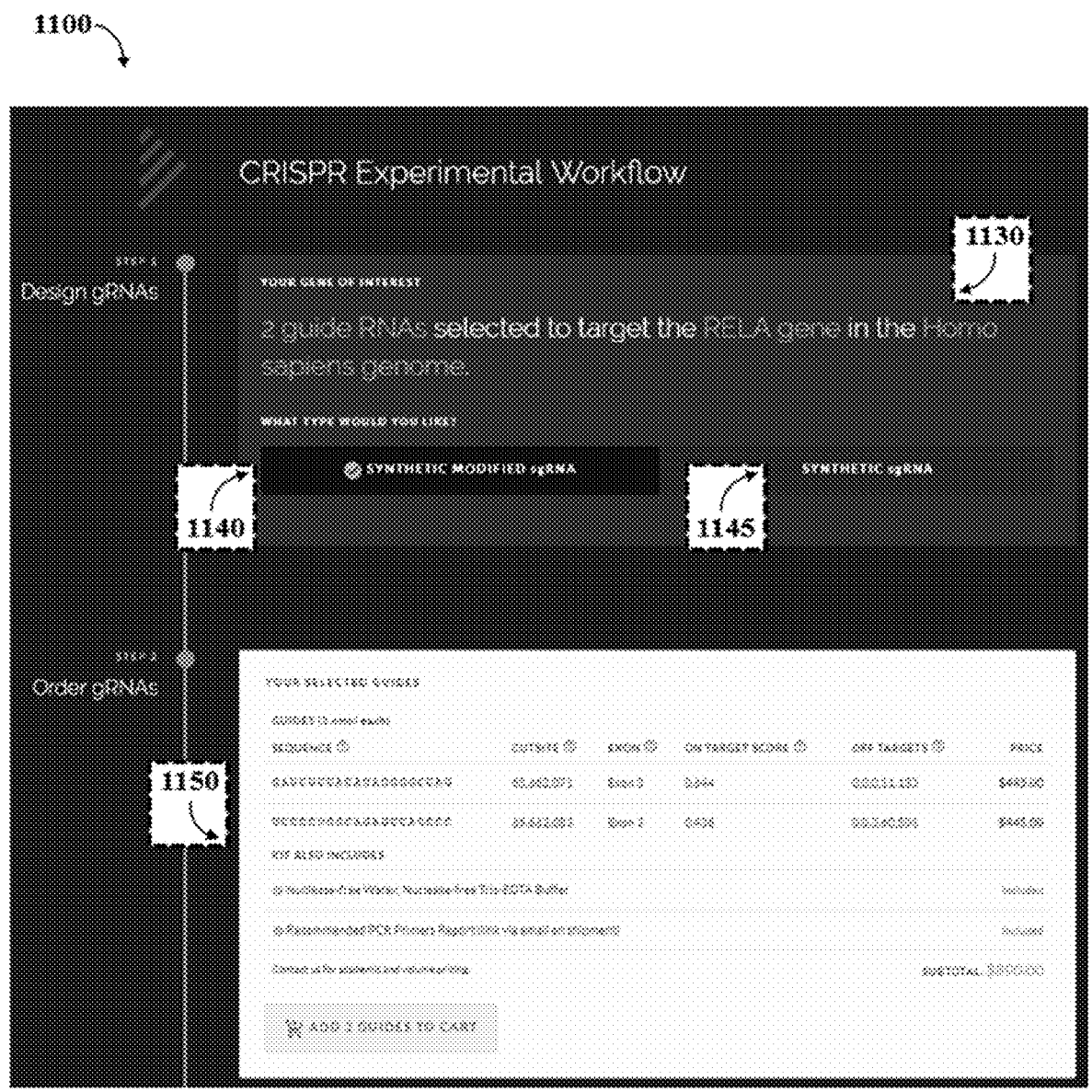

FIG. 11A-B illustrate examples of windows of the GUI for selecting and purchasing a subset one of the one or more gRNAs that are designed to hybridize the gene of the genome of interest. FIG. 11A shows the window 900 of the GUI. The user can select a subset of gRNAs 1110 from the top ranked gRNAs 920 and proceed 1120 to purchase synthesized molecules of the subset of gRNAs 1110. FIG. 11B shows the window 1100 that is displayed to the user once the user proceeds 1120 to purchase the synthesized molecules of the subset of gRNAs 1110. The window 1100 displays a summary 1130 of the selected gRNAs (e.g., the number of selected gRNAs and their intended target gene and genome). The window 1100 also requests the user to choose between modified gRNA 1140 or unmodified gRNA 1145 for synthesis. In addition, the window 1100 displays a final summary 1150 of the gRNAs that are selected for synthesis. The user can proceed for payment of the purchase.

Figure 12A:
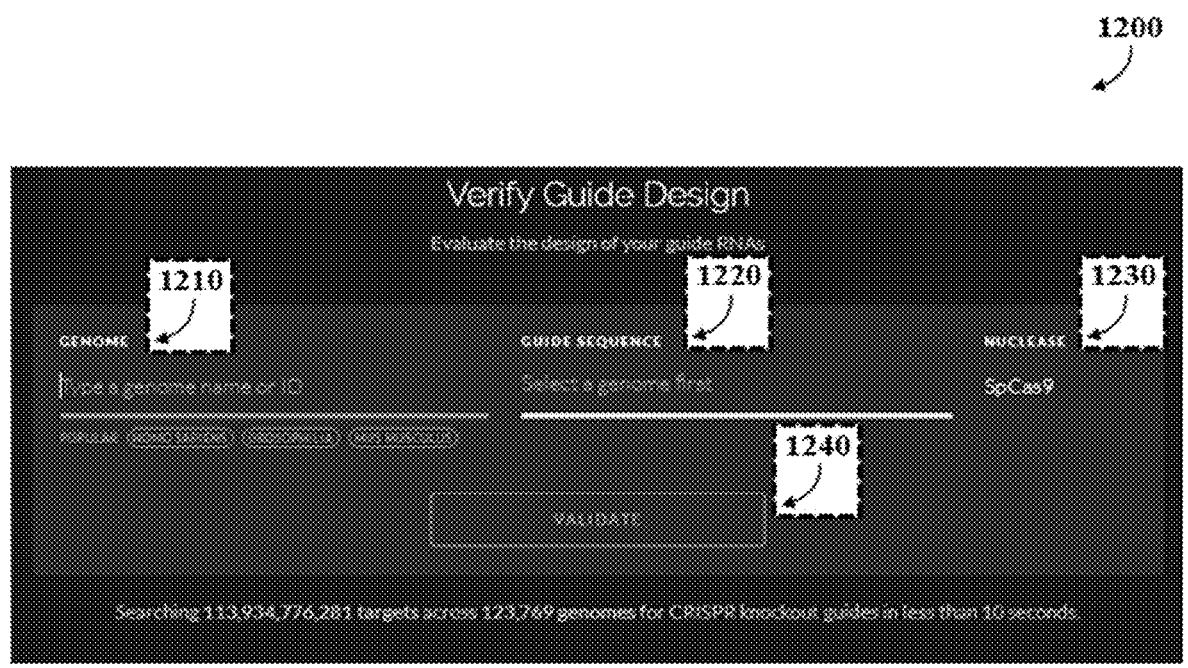
FIGS. 12A-12B illustrate examples of a window the GUI for selecting a genome of a species of interest and inputting a previously generated guide sequence to request validation of the guide performance.
Figure 12B:
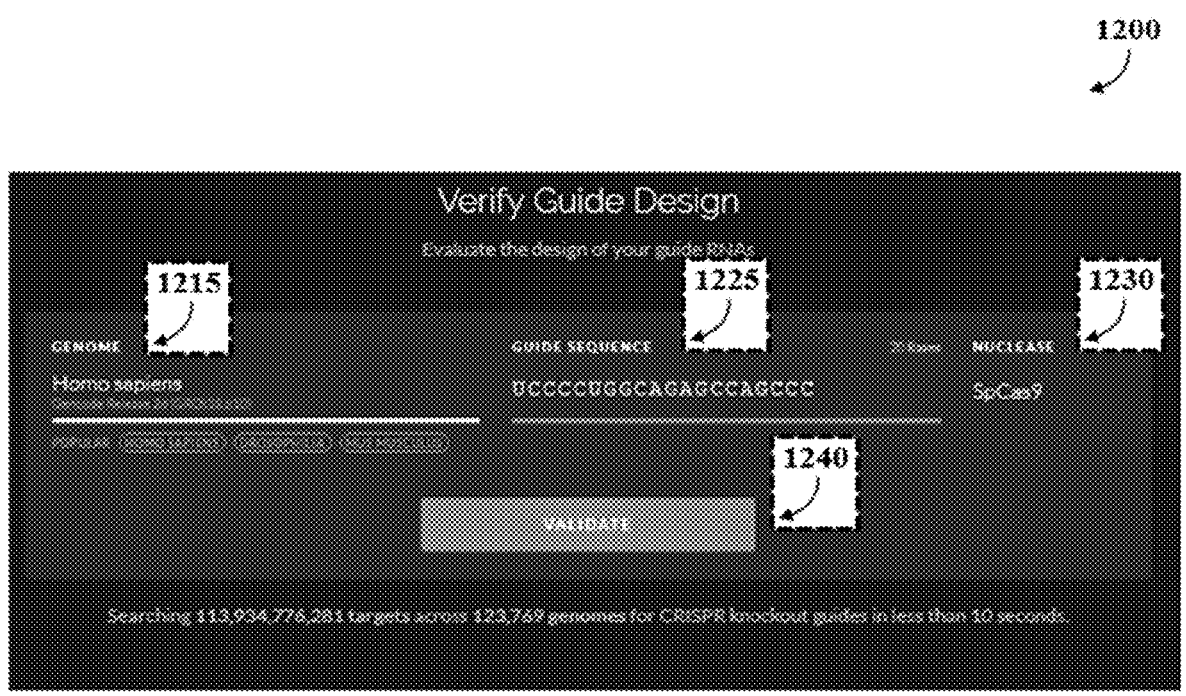

FIG. 12A-B illustrate examples of a window of a GUI for selecting a genome of a species of interest and inputting a previously generated gRNA sequence to request validation of the guide performance. The gRNA can have been previously designed to direct a CRISPR/Cas system for gene editing. FIG. 12A shows the window of the GUI 1200 for gRNA validation. The GUI allows the user to type in the name or the identifier number of the genome 1210 and the sequence of the previously determined gRNA 1220. In this GUI, the nuclease of use 1230 is pre-selected to be *Streptococcus pyogenes* Cas9 (SpCas9). In some cases, the user can select a Cas enzyme of interest. As shown in FIG. 12B, Once the genome 1215, gRNA sequence 1225, and nuclease 1230 are determined, the user can proceed 1240 to validate the gRNA sequence.

Figure 13A:
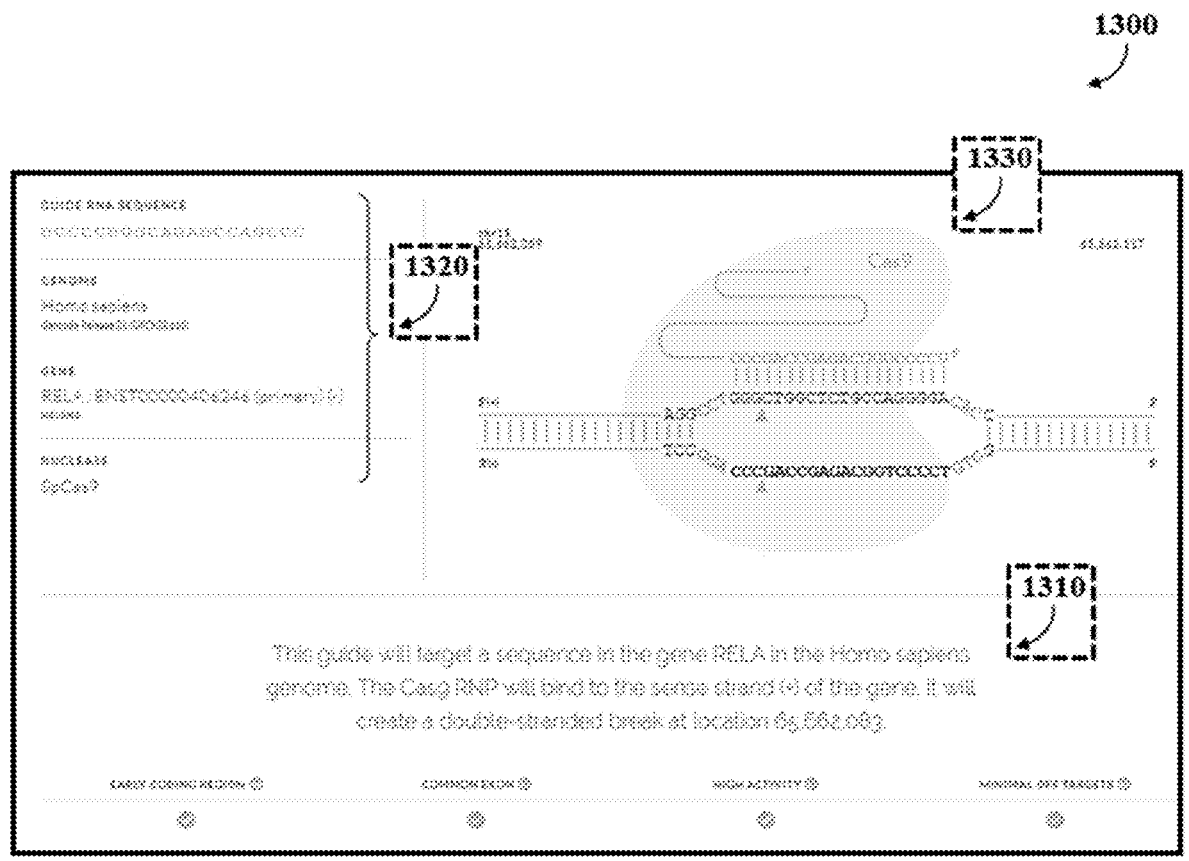
Figure 13B:
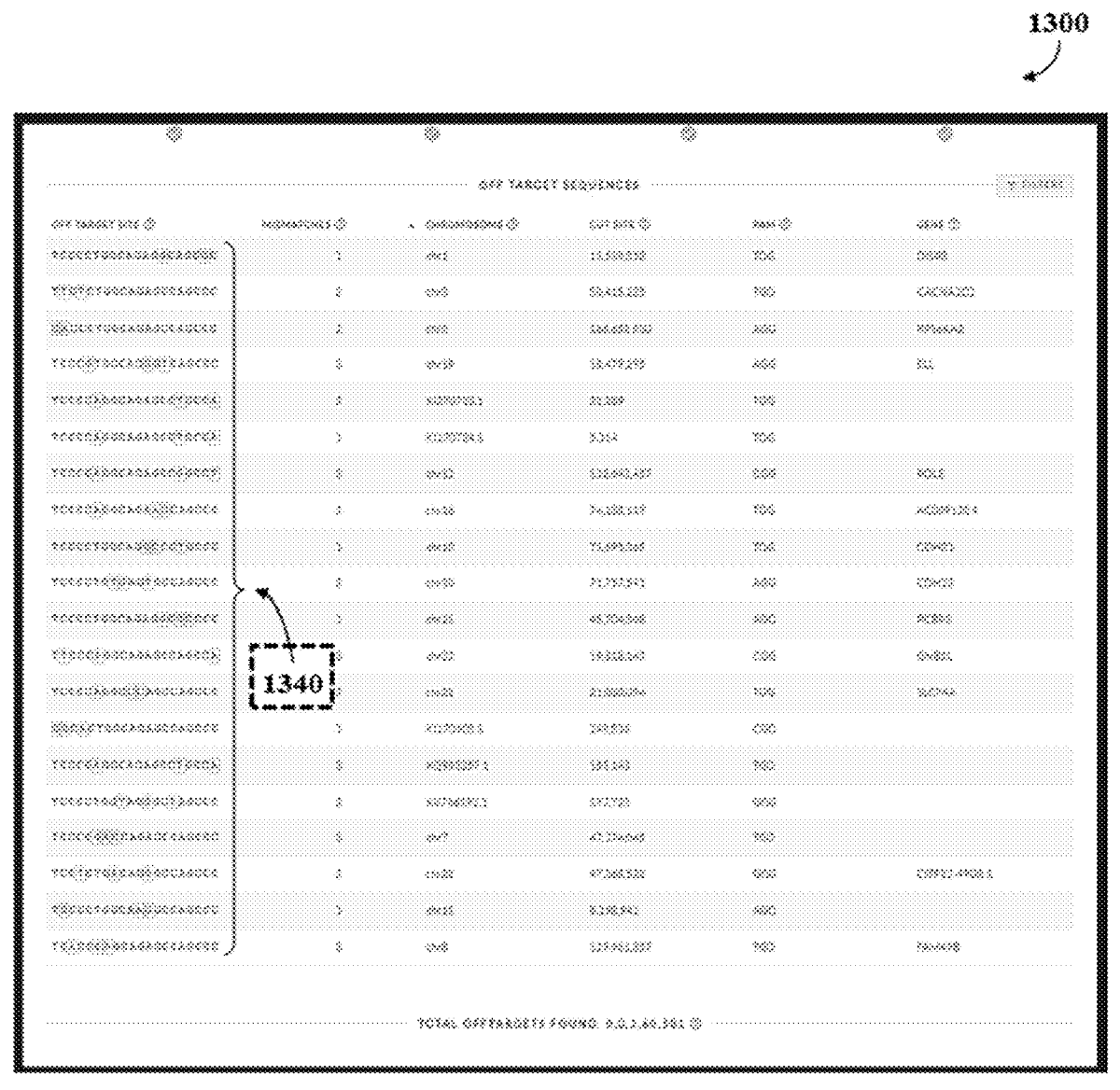

FIG. 13A-B illustrate examples of a window of the GUI for displaying detailed information about validation of a gRNA that is designed to hybridize the gene of the genome of interest. When the user requests a validation of a predetermined gRNA (e.g., the gRNA sequence 1225 in FIG. 12B), the user is directed to a new GUI window 1300, as shown in FIG. 13A. The window 1300 provides a summary 1310 of the performance the predetermined gRNA (e.g., the predicted target gene of the gRNA, the location of the cut site within the genome, etc.). The window 1300 also shows other details 1320 including the predetermined gRNA sequence, genome, and nuclease selected for the analysis. Furthermore, the window 1300 shows a schematic 1330 of the Cas-gRNA complex that drawn to interact with the target region of the predicted target gene. The window 1300 also shows examples of off-target sites 1340 of the predetermined gRNA with accompanying information including a number of mismatches between the predetermined gRNA and each of the off-target site, the position of the off-target site within the genome, and the name of the gene comprising the off-target site, as shown in FIG. 13B.

System

The other different aspect of the present disclosure provides a system comprising: (1) an interface that provides a user with access to more than 10,000 reference genomes; (2) a software for selection of one or more guide RNAs (gRNAs) for a gene in any one of the more than 50,000 reference genomes; and (3) an output system that displays selected guide RNAs.

The system can utilize the aforementioned computer system comprising the computer readable medium for performing the method for designing one or more gRNAs for hybridizing to a genomic region of interest.

The system can comprise from 20,000 to 120,000 reference genomes. The system can comprise at least 20,000, 20,000, 30,000, 40,000, 50,000, 60,000, 70,000, 80,000, 90,000, 100,000, 110,000, 120,000, or more reference genomes. The system can comprise at most 120,000, 110,000, 100,000, 90,000, 80,000, 70,000, 60,000, 50,000, 40,000, 30,000, 20,000, or less reference genomes.

The system can comprise a machine (e.g., a synthesizer) that synthesizes polynucleotides. The software can be in communication with the machine. Alternatively or in addition to, the system can be in communication with an external machine that synthesizes polynucleotides. In some cases, the system can further comprise a script that activates and initiates synthesis of the gRNAs. The synthesis of the gRNAs can be based on the user's selection of one or more gRNAs.

The present disclosure further provides a method for designing a guide RNA (gRNA). The method for designing the gRNA can comprise identifying a primary transcript of a gene. The method for designing the gRNA can comprise identifying a common exon between the primary transcript and a plurality of alternative transcripts. The method for designing the gRNA can comprise identifying a nuclease target site within the common exon. The method for designing the gRNA can comprise calculating a number of off-target binding sites for the nuclease target site against a reference genome sequence, thereby yielding a calculated number of nuclease off-target binding sites. The method for designing the gRNA can comprise calculating an on-target efficiency score, thereby yielding a calculated on-target efficiency score. The method for designing the gRNA can comprise outputting at least one gRNA sequence wherein the gRNA comprises a sequence for which the calculated on-target efficiency is above a threshold and the calculated number of nuclease off-target binding sites is zero.

In some cases, the method for designing the gRNA can comprise directing a synthesis of a nucleic acid that has partial complementarity to the target site. The partial complementarity between the gRNA and the target site can comprise a mismatch of 1, 2, 3, 4, 5, 6, 7, 8, 9, 10, or more than 10 nucleotides.

The present disclosure further provides a system for processing a biopolymer synthesis request from a user over a network. The system can comprise a communications interface that is configured to communicate with a digital computer of the user over the network. The system can comprise a reference genome database that stores one or more reference genomes. The system can comprise a computer comprising one or more computer processors operatively coupled to the communications interface and the database. The one or more computer processors can be individually or collectively programmed to: (a) receive from the communications interface over the network, the biopolymer synthesis request from the digital computer of the user, which biopolymer synthesis request comprises target genomic information; (b) process the target genomic information against the one or more reference genomes from the database to identify a target sequence corresponding to the target genomic information; (c) execute an algorithm to generate a first set of guide ribonucleic acid (gRNA) sequences that are at least partially complementary to the target sequence, and calculate an off-target complementarity score for each of the gRNA sequences in the first set of gRNA sequences; (d) output a second set of gRNA sequences for display on a graphical user interface of the digital computer of the user, where each of the second set of gRNA sequences has a calculated off-target complementarity score below a threshold; and (e) receive from the digital computer of the user a selection of a given gRNA sequence from the second set of gRNA sequences.

In some cases, the one or more computer processors can be individually or collectively programmed to direct the given gRNA sequence in a queue for synthesizing the gRNA sequence. In some cases, at least one genome in the reference genome database can be a personalized genome of an individual. In some cases, at least one genome in the reference genome database can a set of personalized genomes of a population afflicted with a condition. In some cases, the reference genome can be a *Homo sapiens* reference genome.

In some cases, the one or more computer processors can be individually or collectively programmed to output a predicted genomic sequence. The predicted genomic sequence can represent a predicted output of editing the target genomic information with one or more gRNA's from the second set of gRNA sequences. The predicted genomic sequence can comprise a genomic deletion. The predicted genomic sequence comprises a genomic insertion.

In some cases, calculating the off-target complementarity score comprises calculating an Azimuth score. In some cases, the second set of gRNA sequences can display at least two gRNAs above a certain threshold.

In some cases, the reference genome database can comprise at least 50 thousand reference genomes. In some cases, the reference genome database can comprise at least 120 thousand reference genomes.

The present disclosure further provides a method for processing a biopolymer synthesis request from a user over a network. The method can comprise: (a) receiving the biopolymer synthesis request from a digital computer of the user over the network, which biopolymer synthesis request comprises target genomic information; (b) processing the target genomic information against one or more reference genomes from a reference genome database to identify a target sequence corresponding to the target genomic information; (c) using one or more computer processors to execute an algorithm to (i) generate a first set of guide ribonucleic acid (gRNA) sequences that are at least partially complementary to the target sequence, and (ii) calculate an off-target complementarity score for each of the gRNA sequences in the first set of gRNA sequences for each of the gRNA sequences; (d) outputting a second set of gRNA sequences for display on a graphical user interface of the digital computer of the user, where each of the second set of gRNA sequences has a calculated off-target complementarity score below a threshold; and (e) receiving from the digital computer of the user a request for a synthesis of a given gRNA sequence from the second set of gRNA sequences.

In some cases, a computer program (e.g., a computer readable medium) can be configured for instructing a computer to perform the method of processing a biopolymer synthesis request from a user over a network.

In some cases, one or more computer processors receiving the request for the synthesis can be individually or collectively programmed to direct the synthesis of the given gRNA sequence from the second set of gRNA sequences in a synthesizer. In some cases, at least one genome in the reference genome database can be a personalized genome of an individual. In some cases, at least two genomes in the reference genome database can be personalized genomes of a population afflicted with a condition. In some cases, the reference genome can be a *Homo sapiens* reference genome.

In some cases, the method can further comprise outputting a predicted genomic sequence. The predicted genomic sequence can represent a predicted output of editing the target genomic information with one or more gRNAs from the second set of gRNA sequences. In some cases, the predicted genomic sequence can comprise a genomic deletion. In some cases, the predicted genomic sequence can comprise a genomic insertion. In some cases, the calculating can calculate an Azimuth score. In some cases, the second set of gRNA sequences can display at least two gRNAs above a certain threshold. In some cases, the reference genome database can comprise at least 50 thousand reference genomes. In some cases, the reference genome database can comprise at least 120 thousand reference genomes.

The present disclosure further provides a non-transitory computer-readable medium comprising machine executable code that, upon execution by one or more computer processors, implements a method for processing a biopolymer synthesis request from a user over a network. The method can comprise receiving the biopolymer synthesis request from a digital computer of the user over the network, which biopolymer synthesis request comprises target genomic information. The method can comprise processing the target genomic information against one or more reference genomes from a reference genome database to identify a target sequence corresponding to the target genomic information. The method can comprise executing an algorithm to generate a first set of guide ribonucleic acid (gRNA) sequences that are at least partially complementary to the target sequence, and calculate an off-target complementarity score for each of the gRNA sequences in the first set of gRNA sequences. The method can comprise outputting a second set of gRNA sequences for display on a graphical user interface of the digital computer of the user, where each of the second set of gRNA sequences has a calculated off-target complementarity score below a threshold. The method can comprise receiving from the digital computer of the user a selection of a given gRNA sequence from the second set of gRNA sequences Computer Systems The present disclosure provides computer systems that are programmed to implement methods of the disclosure. Computer systems of the present disclosure can be used to design one or more guide RNAs for hybridizing to a genomic region of interest. The genomic region of interest can be a gene of a genome of a species. Information from any of the computer systems described herein can provide a report to a remote computer.

Figure 14:
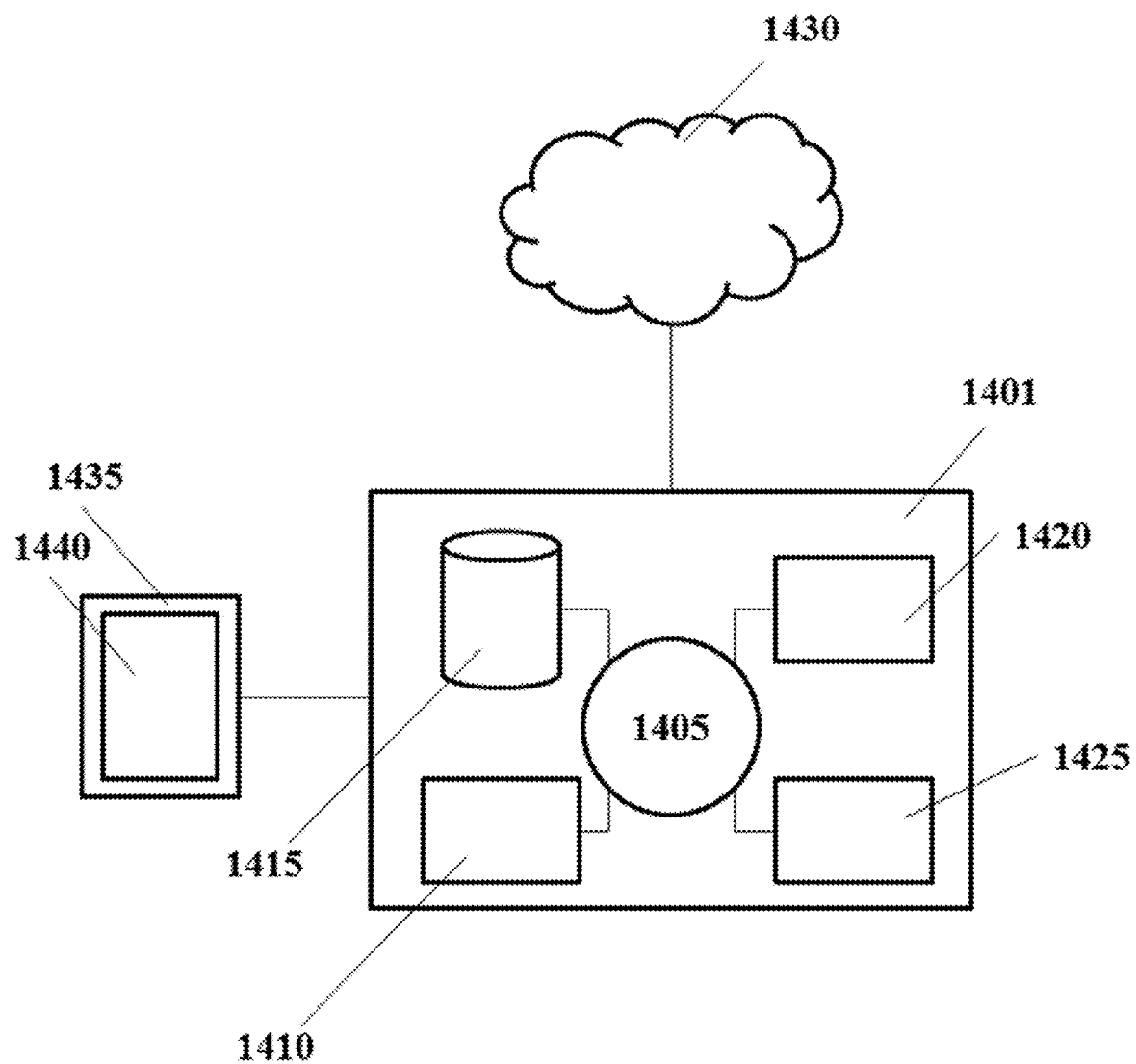
FIG. 14 shows a computer system that can be programmed or otherwise configured to implement methods provided herein.

FIG. 14 shows a computer system 1401 that is programmed or otherwise configured to communicate with and regulate various aspects of a computer system of the present disclosure.

The computer system 1401 can regulate various aspects of the present disclosure, such as, for example, designing one or more guide RNAs for hybridizing to a gene of a genome of a species, or calculating an off-target value by enumerating a number of mismatches to potential guide RNA hybridizing sites in the genome of interest. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which can enable devices coupled to the computer system 1401 to behave as a client or a server.

The CPU 1405 can execute a sequence of machine-readable instructions, which can be embodied in a program or software. The instructions can be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, can take many forms, including but not limited to, a tangible storage medium, a carrier wave medium or physical transmission medium. Non-volatile storage media include, for example, optical or magnetic disks, such as any of the storage devices in any computer(s) or the like, such as can be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

The computer system 1401 can include or be in communication with an electronic display 1435 that comprises a user interface (UI) 1440 for providing the use, for example, the ability to select a species of interest and gene of interest from the species of interest. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, design one or more gRNAs for hybridizing to a genomic region of interest of a species, and activate and initiate synthesis of at least one of the one or more gRNAs.

EXAMPLES

Figure 15:
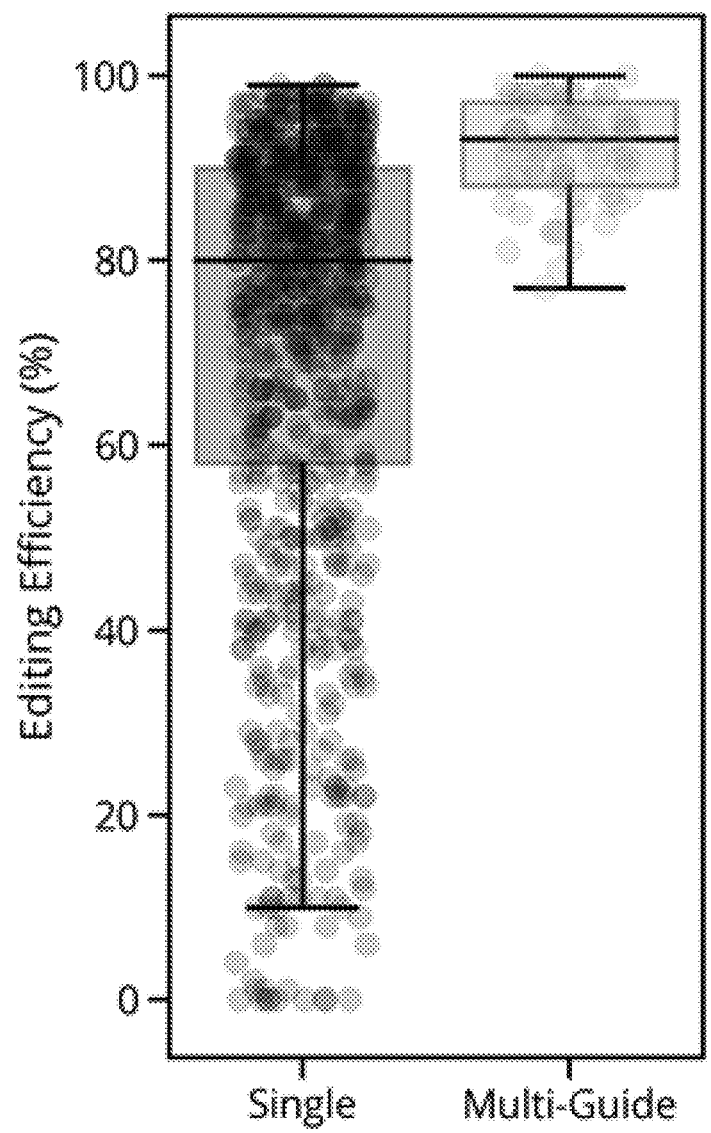
FIG. 15 illustrates editing efficiency of single guide RNA vs. multiple guide RNA. For single guide RNA, each data point represents the percent editing efficiency, or KO Score, of one transfected sgRNA. For multi-guide, each data point represents the KO Score for three co-transfected sgRNAs.

Example 1: Use of Multiple Guide RNAs Achieves Higher Editing Efficiency than Use of a Single Guide RNAs A total of 228 guide RNAs were designed to hybridize 76 genes, with three guide RNAs designed per gene. Each set of three guide RNAs was designed such that the inter-guide spacing was at least 30 bp. Guide RNAs were introduced into HEK293 and MCF7 cells seeded at 35,000 cells per well on a 96 well plate. Guide RNAs used in single guide editing were transfected at 4.5 μmol, while guide RNAs for multi-guide RNA use were transfected at 2.25 μmol each. All guide RNAs were transfected as ribonucleoproteins (RNPs) through nucleofection. Prior to transfection, 0.5 μmol of Cas9 was complexed with the RNPs. At 2 days post-transfection the resulting genotype of the cells was interrogated via Sanger sequencing, and the overall editing efficiency was analyzed using Inference of CRISPR Edits (ICE). The percent editing efficiency was used to indicate a percentage of cells comprising a non-wild type genotype at the location at which the gRNAs were designed to edit. Editing efficiency was assessed for the use of a single gRNA per gene as well as a set of three gRNA per gene (FIG. 15). Boxplots behind the datapoints indicate the median, 25/75$^{th}$ percentiles and 5195$^{th}$ percentiles. These results indicated that use of three gRNAs with the specified inter-guide spacing achieved a higher editing efficiency than the use of a single gRNA that hybridizes to a target gene (p<1E−15, Mann-Whitney U test).

Figure 16:
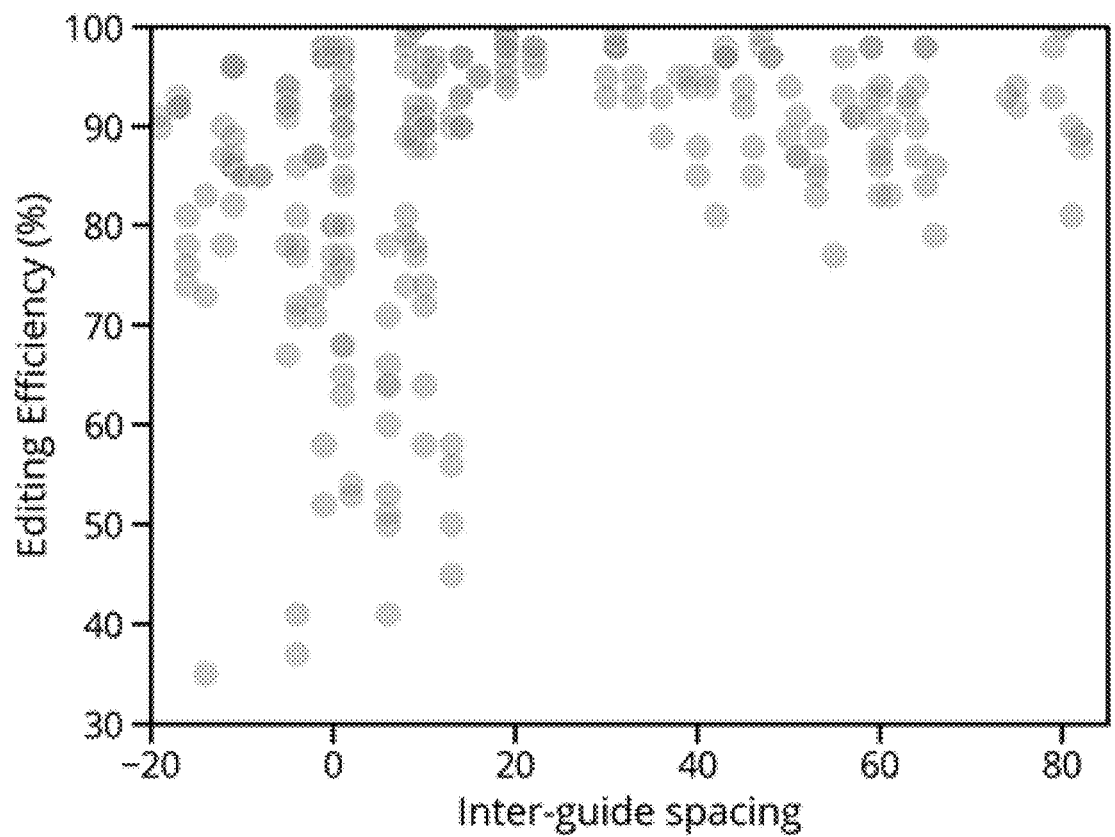
FIG. 16 illustrates percent editing efficiency relative to spacing of guide RNAs in a multi-gRNA set.

Editing outcomes using multi-guide sgRNAs were further analyzed for the effect of guide spacing. 537 gRNAs were designed to hybridize 179 genes, with three gRNAs designed per gene. These gRNAs were designed with inter-guide spacing between −20 bp (i.e. completely overlapping) to 80 bp. Guide RNAs for multi-guide were transfected at 2.25 μmol each. All gRNAs were transfected as ribonucleoproteins (RNPs) through nucleofection. Prior to transfection, 0.5 μmol Cas9 was complexed with the RNPs. At 2 days post-transfection the resulting genotype of the cells was interrogated via Sanger sequencing, and the overall editing efficiency was analyzed. As the inter-guide spacing (i.e. the end-to-start distance between guides) increased above 30 base pairs (bp), the overall editing efficiency improved such that efficiencies less than 75% were not observed (FIG. 16).

Example 2: Combinations of Multiple Guide RNA Kits

Figure 17:
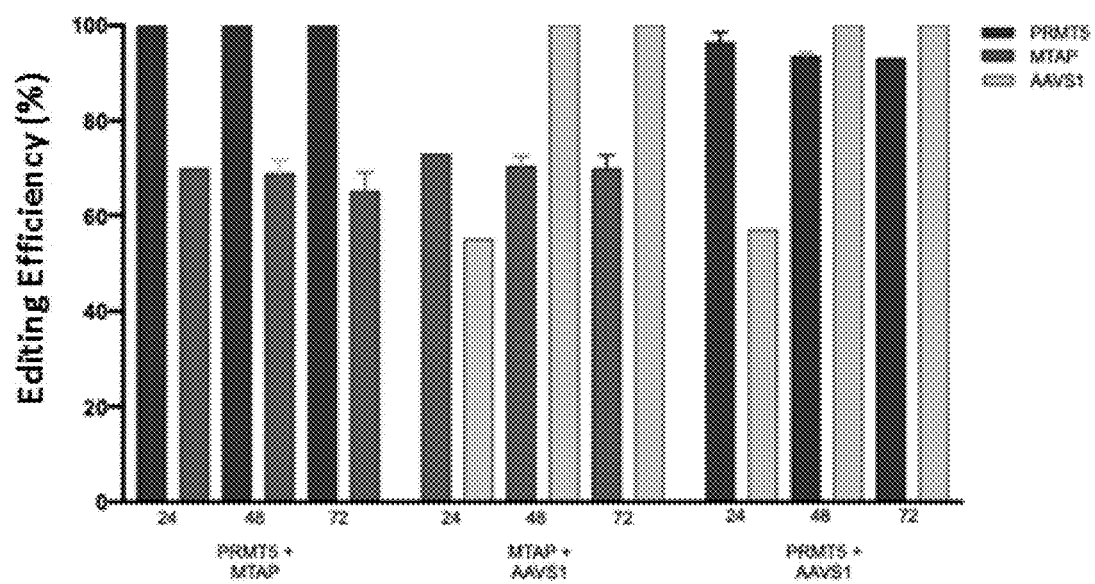
FIG. 17 illustrates percent editing efficiency of double knockouts using multiple gRNAs for each pair of genes targeted.

Nine sgRNAs were designed, three sgRNAs to target each of three target regions within a human genome: two genes, protein arginine methyltransferase 5 (PRMT5) and methyl-thioadenosine phosphorylase (MTAP), as well as a site within adeno-associated virus integration site 1 (AAVS1). In each set of sgRNAs, the inter-guide spacing was at least 30 bp. Editing efficiency for each gene in each pairwise combination was determined via Sanger sequencing (FIG. 17).

5000 Hep3B cells were seeded per well in a 96-well plate. Using Nucleofector™ technology (Lonza), these cells were transfected with multiple RNPs targeting the pairs, and cell titers were assayed at 24, 48, and 72 post transfection. These results indicate that one can create edits at multiple genomic loci simultaneously in a single transfection.

Figure 18A:
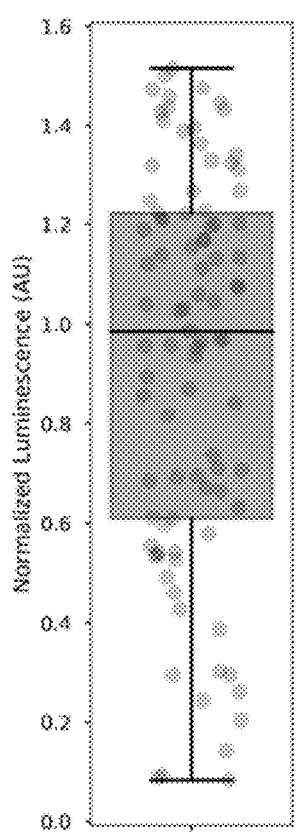
FIGS. 18A-18B illustrate screening of arrayed libraries using a multi-guide knock-out design.
Figure 18B:
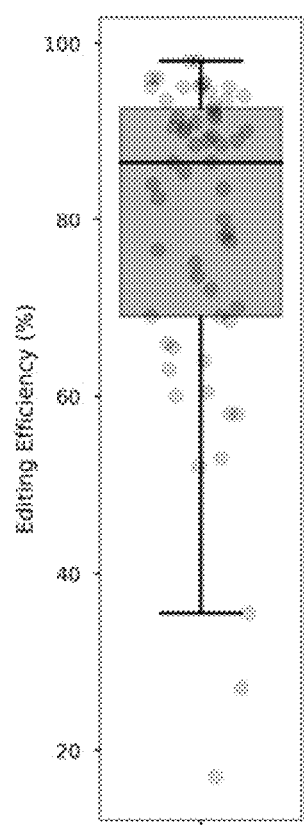

Example 3: Arrayed Library Screening 35,000 U2OS cells were seeded per well in 92 wells of a 96 well plate. Each of the 92 wells further contained a set of 2 or 3 sgRNAs targeting a gene with inter-guide spacing of at least 30 bp, for a total of 92 different genes targeted by the screening assay, and a Cas9 endonuclease. Cells were transfected using Nucleofector™ technology (Lonza). Cell viability was subsequently assessed using a CellTiter-Glo® Luminescent Cell Viability Assay at 6 days post-transfection (FIG. 18A). Additionally, these cells were genotyped with Sanger sequencing at 2 days post-transfection, followed by analysis using Inference of CRISPR Edits (ICE) to determine editing efficiency (FIG. 18B). The ability to assess the resulting genotype of the same population of cells can be an advantage of arrayed screening approaches over pooled screening approaches.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A method for editing a gene within a genomic region of interest, the method comprising:
  (a) contacting a cell comprising the gene within genomic region of interest with: a set of guide RNAs (gRNAs) comprising
    (i) a first gRNA configured to hybridize to a first site of the genomic region of interest and capable of interacting with a nuclease and generating a first double stranded break;
    (ii) a second gRNA configured to hybridize to a second site of the genomic region of interest and capable of interacting with the nuclease and generating a second double stranded break, and
    (iii) a third gRNA configured to hybridize to a third site of the genomic region of interest and capable of interacting with the nuclease and generating a third double stranded break, wherein the first gRNA, second gRNA, and third gRNA are different and each hybridize to a site that is at least 15 base pairs and at most 2000 base pairs apart from each other; and
  (b) introducing the set of gRNA and the nuclease into the cell to generate an edit that modifies the gene; wherein an editing efficiency of the set of gRNA is higher than an individual editing efficiency of each of the gRNAs.

2. The method of claim 1, wherein the first gRNA, the second gRNA, and the third gRNA are configured to hybridize to the gene.

3. The method of claim 2, wherein the first gRNA, the second gRNA, and the third gRNA are configured to hybridize an exon of the gene, a regulatory element, a cis-regulatory element or a trans-regulatory element.

4. The method of claim 3, wherein the regulatory element is a cis-regulatory element and selected from the group consisting of: a promoter, an enhancer, and a silencer.

5. The method of claim 1, further comprising introducing into the cell a donor polynucleotide.

6. The method of claim 5 wherein the donor polynucleotide comprises a point mutation, allele, tag or exogenous exon relative to a wild-type genotype of the cell.

7. The method of claim 1, wherein the edit is a knock-out of the gene, an insertion or a deletion relative to wild-type.

8. The method of claim 7, wherein the edit is an insertion and improves a function of the gene.

9. The method of claim 1, wherein each of the first, second and third gRNA is hybridizable to a target site that is at least 30 bases apart from the target site of the other gRNA from the set of gRNAs.

10. The method of claim 1, further comprising introducing a plurality of sets of gRNA targeting a plurality of genomic regions of interest.

11. The method of claim 1, further comprising screening the population of cells for a phenotype.

12. The method of claim 1, wherein the on-target efficiency threshold value for each guide RNA of the initial set of gRNAs is an azimuth score greater than 0.4.

13. The method of claim 1, wherein the contacting comprises transfecting the cell with the set of gRNAs as ribonucleoprotein complexes.

14. The method of claim 1, wherein the introducing comprises transfecting the cell with the set of gRNAs as ribonucleoprotein complexes.

15. The method of claim 1, wherein the nuclease is Cas9 nuclease, C2c1 nuclease, C2c3 nuclease, or Cpf1 nuclease.

16. The method of claim 1, wherein the first gRNA, the second gRNA, and the third guide RNA comprise a 5' end modification and a 3' end modification.

17. The method of claim 16, wherein the 5' end modification comprises a phosphorothioate internucleotide linkage and a 2'-O-methyl sugar modification and the 3' end modification comprises a phosphorothioate internucleotide linkage and a 2'-O-methyl sugar modification.

18. The method of claim 17, wherein the first gRNA, the second gRNA, and the third gRNA are single guide RNAs (sgRNAs), wherein the first binding site and the second binding site are separated by 15-80 base pairs, wherein the second binding site and the third binding site are separated by 15-80 base pairs, wherein the first binding site, the second binding site, and the third binding site are in an exon of a gene, wherein the exon is in a first half of the gene.

19. The method of claim 18, wherein the first gRNA is configured to hybridize to a binding-site that is 30-80 base pairs apart from a binding site hybridizable to the second gRNA and the second gRNA is configured to hybridize to a binding-site that is 30-80 base pairs apart from a binding site hybridizable to the third gRNA.

* * * * *

SEQUENCE LISTING

```
<160> NUMBER OF SEQ ID NOS: 91

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aggccugggc uggcucugcc                                                    20

<210> SEQ ID NO 2
<211> LENGTH: 20
<212> TYPE: DNA
<213> ORGANISM: Homo sapiens

<400> SEQUENCE: 2
aggcctgggc tggctctgcc                                                    20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3 ucccuggca gagccagccc                                                     20
```

<210> SEQ ID NO 4
<211> LENGTH: 20
<212> TYPE: DNA
<213> ORGANISM: Homo sapiens

<400> SEQUENCE: 4
tcccctggca gagccagccc                                              20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uaggggccag aggccugggc                                              20

<210> SEQ ID NO 6
<211> LENGTH: 20
<212> TYPE: DNA
<213> ORGANISM: Homo sapiens

<400> SEQUENCE: 6
taggggccag aggcctgggc                                              20

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cacauagggg ccagaggccu                                              20

<210> SEQ ID NO 8
<211> LENGTH: 20
<212> TYPE: DNA
<213> ORGANISM: Homo sapiens

<400> SEQUENCE: 8
cacatagggg ccagaggcct                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tggcgcagtg ctgaccttga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggcgcagtgc tgaccttgat                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgcagtgctg accttgatgg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcagtgctga ccttgatggt                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cagtgctgac cttgatggtg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgctgacctt gatggtgggg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gctgaccttg atggtggggt                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

```
cttgatggtg gggtgggtct                                              20
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
tgatggtggg gtgggtcttg                                              20
```

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
gatggtgggg tgggtcttgg                                              20
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
gtatctgtgc tcctctcgcc                                              20
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
tatctgtgct cctctcgcct                                              20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
ctcgcctggg atgctgcccg                                              20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
gggatgctgc ccgcggagcg                                              20
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcggagcgcc cctcgcactt                                            20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cggagcgccc ctcgcacttg                                            20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agcgcccctc gcacttgtag                                            20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctcgcacttg tagcggaagc                                            20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tcgcacttgt agcggaagcg                                            20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cgcacttgta gcggaagcgc                                            20

```
<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaagcgcatg ccccgctgct                                                       20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aagcgcatgc cccgctgctt                                                       20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgctgcttgg gctgctcaat                                                       20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gctgcttggg ctgctcaatg                                                       20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctgcttgggc tgctcaatga                                                       20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctgctcaatg atctccacat                                                       20
```

```
<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgctcaatga tctccacata                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gctcaatgat ctccacatag                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gatctccaca taggggccag                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ccacataggg gccagaggcc                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 catagggggcc agaggcctgg                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gaggcctggg ctggctctgc                                                    20

<210> SEQ ID NO 41
```

-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcctgggct ggctctgcca                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gcctgggctg gctctgccag                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gggctggctc tgccagggga                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggggacaccg cagccccatt                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gacaccgcag ccccattagg                                                    20

<210> SEQ ID NO 46
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uccccuggca gagccagccc                                                    20

<210> SEQ ID NO 47
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gaucuccaca uaggggccag                                                   20

<210> SEQ ID NO 48
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ccaggccucu ggccccuaug                                                   20

<210> SEQ ID NO 49
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gcucaaugau cuccacauag                                                   20

<210> SEQ ID NO 50
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gauggugggg ugggucuugg                                                   20

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gcugaccuug auggugggu                                                    20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ugcugaccuu gauggugggg                                                   20

<210> SEQ ID NO 53
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 53
cagugcugac cuugauggug                                                    20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gcagugcuga ccuugauggu                                                    20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
cgcagugcug accuugaugg                                                    20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
caagacccac cccaccauca                                                    20

<210> SEQ ID NO 57
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gacaccgcag ccccauuagg                                                    20

<210> SEQ ID NO 58
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ggggacaccg cagccccauu                                                    20

<210> SEQ ID NO 59
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 59 aaugggggcug cggugucccc                                                   20

<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uccccuggca gagccagccc                                                    20

<210> SEQ ID NO 61
<211> LENGTH: 30
<212> TYPE: DNA
<213> ORGANISM: Homo sapiens

<400> SEQUENCE: 61
aggcctgggc tggctctgcc agggacacc                                          30

<210> SEQ ID NO 62
<211> LENGTH: 30
<212> TYPE: DNA
<213> ORGANISM: Homo sapiens

<400> SEQUENCE: 62 ggtgtccct ggcagagcca gcccaggcct                                          30

<210> SEQ ID NO 63
<211> LENGTH: 20
<212> TYPE: DNA
<213> ORGANISM: Homo sapiens

<400> SEQUENCE: 63
ttctctggca gagccagccc                                                    20

<210> SEQ ID NO 64
<211> LENGTH: 20
<212> TYPE: DNA
<213> ORGANISM: Homo sapiens

<400> SEQUENCE: 64
caccctggca gagccagccc                                                    20

<210> SEQ ID NO 65
<211> LENGTH: 20
<212> TYPE: DNA
<213> ORGANISM: Homo sapiens

<400> SEQUENCE: 65 tccctggca gaggcagcgc                                                     20

<210> SEQ ID NO 66
<211> LENGTH: 20
<212> TYPE: DNA
<213> ORGANISM: Homo sapiens

<400> SEQUENCE: 66
```
tccccaggca gaagcagccc                                                    20

<210> SEQ ID NO 67
<211> LENGTH: 20
<212> TYPE: DNA
<213> ORGANISM: Homo sapiens

<400> SEQUENCE: 67
tggcctggca aagccagccc                                                    20

<210> SEQ ID NO 68
<211> LENGTH: 20
<212> TYPE: DNA
<213> ORGANISM: Homo sapiens

<400> SEQUENCE: 68
tcccctgaaa cagccagccc                                                    20

<210> SEQ ID NO 69
<211> LENGTH: 20
<212> TYPE: DNA
<213> ORGANISM: Homo sapiens

<400> SEQUENCE: 69
tcccctggca gaggcgcccc                                                    20

<210> SEQ ID NO 70
<211> LENGTH: 20
<212> TYPE: DNA
<213> ORGANISM: Homo sapiens

<400> SEQUENCE: 70
ttcccaggca gagccagcca                                                    20

<210> SEQ ID NO 71
<211> LENGTH: 20
<212> TYPE: DNA
<213> ORGANISM: Homo sapiens

<400> SEQUENCE: 71
tccccaggcc cagccagccc                                                    20

<210> SEQ ID NO 72
<211> LENGTH: 20
<212> TYPE: DNA
<213> ORGANISM: Homo sapiens

<400> SEQUENCE: 72
tcccctggca gagcctggca                                                    20

<210> SEQ ID NO 73
<211> LENGTH: 20
<212> TYPE: DNA
<213> ORGANISM: Homo sapiens

<400> SEQUENCE: 73
ggcactggca gagccagccc                                                    20

<210> SEQ ID NO 74
<211> LENGTH: 20
<212> TYPE: DNA
<213> ORGANISM: Homo sapiens

<400> SEQUENCE: 74

```
tcccctggca gagaaagcac                                              20

<210> SEQ ID NO 75
<211> LENGTH: 20
<212> TYPE: DNA
<213> ORGANISM: Homo sapiens

<400> SEQUENCE: 75
gcccttggaa gagccagccc                                              20

<210> SEQ ID NO 76
<211> LENGTH: 20
<212> TYPE: DNA
<213> ORGANISM: Homo sapiens

<400> SEQUENCE: 76
ttccctggct gagcaagccc                                              20

<210> SEQ ID NO 77
<211> LENGTH: 20
<212> TYPE: DNA
<213> ORGANISM: Homo sapiens

<400> SEQUENCE: 77
tccccaggca gagccggcct                                              20

<210> SEQ ID NO 78
<211> LENGTH: 20
<212> TYPE: DNA
<213> ORGANISM: Homo sapiens

<400> SEQUENCE: 78
tcccctctca gtgccagccc                                              20

<210> SEQ ID NO 79
<211> LENGTH: 20
<212> TYPE: DNA
<213> ORGANISM: Homo sapiens

<400> SEQUENCE: 79
gcccctggca gtgcaagccc                                              20

<210> SEQ ID NO 80
<211> LENGTH: 20
<212> TYPE: DNA
<213> ORGANISM: Homo sapiens

<400> SEQUENCE: 80
tccccaggca gagcctgcca                                              20

<210> SEQ ID NO 81
<211> LENGTH: 20
<212> TYPE: DNA
<213> ORGANISM: Homo sapiens

<400> SEQUENCE: 81
tccctgggca gagccagctc                                              20

<210> SEQ ID NO 82
<211> LENGTH: 20
<212> TYPE: DNA
<213> ORGANISM: Homo sapiens
```

<400> SEQUENCE: 82
gctcctggca gtgccagccc                                                    20

<210> SEQ ID NO 83
<211> LENGTH: 20
<212> TYPE: DNA
<213> ORGANISM: Homo sapiens

<400> SEQUENCE: 83
tcccgtggca gggtcagccc                                                    20

<210> SEQ ID NO 84
<211> LENGTH: 20
<212> TYPE: DNA
<213> ORGANISM: Homo sapiens

<400> SEQUENCE: 84
tcccctggca ggccctgccc                                                    20

<210> SEQ ID NO 85
<211> LENGTH: 20
<212> TYPE: DNA
<213> ORGANISM: Homo sapiens

<400> SEQUENCE: 85
tcccctgtga gtgccagccc                                                    20

<210> SEQ ID NO 86
<211> LENGTH: 20
<212> TYPE: DNA
<213> ORGANISM: Homo sapiens

<400> SEQUENCE: 86
tcccctggta gggctagccc                                                    20

<210> SEQ ID NO 87
<211> LENGTH: 20
<212> TYPE: DNA
<213> ORGANISM: Homo sapiens

<400> SEQUENCE: 87
tccccgacca gagccagccc                                                    20

<210> SEQ ID NO 88
<211> LENGTH: 20
<212> TYPE: DNA
<213> ORGANISM: Homo sapiens

<400> SEQUENCE: 88
tcctctgaca gggccagccc                                                    20

<210> SEQ ID NO 89
<211> LENGTH: 20
<212> TYPE: DNA
<213> ORGANISM: Homo sapiens

<400> SEQUENCE: 89
tgccctggca aggccagccc                                                    20

<210> SEQ ID NO 90
<211> LENGTH: 20
<212> TYPE: DNA
<213> ORGANISM: Homo sapiens

```
<400> SEQUENCE: 90
tcacccagca gagccagccc                                                  20

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 91

His His His His His His
1               5
```